United States Patent
Karp et al.

(10) Patent No.: US 11,046,642 B2
(45) Date of Patent: Jun. 29, 2021

(54) SYSTEMS AND METHODS FOR PRODUCING NITRILES

(71) Applicant: Alliance for Sustainable Energy, LLC, Golden, CO (US)

(72) Inventors: Eric M. Karp, Denver, CO (US); Gregg Tyler Beckham, Golden, CO (US); Derek Richard Vardon, Lakewood, CO (US); Todd R. Eaton, Denver, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 0 days.

(21) Appl. No.: 15/775,632

(22) PCT Filed: Feb. 17, 2017

(86) PCT No.: PCT/US2017/018272
§ 371 (c)(1),
(2) Date: May 11, 2018

(87) PCT Pub. No.: WO2017/143124
PCT Pub. Date: Aug. 24, 2017

(65) Prior Publication Data
US 2018/0346411 A1     Dec. 6, 2018

Related U.S. Application Data

(60) Provisional application No. 62/437,303, filed on Dec. 21, 2016, provisional application No. 62/297,187, filed on Feb. 19, 2016.

(51) Int. Cl.
| | | |
|---|---|---|
| *C07C 253/22* | (2006.01) | |
| *B01J 21/06* | (2006.01) | |
| *B01D 3/00* | (2006.01) | |
| *B01D 15/08* | (2006.01) | |

(52) U.S. Cl.
CPC ............ *C07C 253/22* (2013.01); *B01D 3/009* (2013.01); *B01D 15/08* (2013.01); *B01J 21/063* (2013.01)

(58) Field of Classification Search
None
See application file for complete search history.

(56) References Cited

U.S. PATENT DOCUMENTS

| | | |
|---|---|---|
| 3,337,610 A | 8/1967 | Bellringer et al. |
| 4,179,462 A | 12/1979 | Olivé et al. |
| 5,138,086 A | 8/1992 | Honda et al. |
| 5,210,296 A | 5/1993 | Cockrem et al. |
| 6,005,134 A | 12/1999 | Terasaka et al. |
| 6,475,759 B1 | 11/2002 | Carlson et al. |
| 2010/0048850 A1 | 2/2010 | Dubois et al. |
| 2011/0105791 A1 | 5/2011 | Kuppinger et al. |
| 2013/0313192 A1 | 11/2013 | Wang et al. |
| 2014/0045231 A1 | 2/2014 | Lynch et al. |
| 2014/0309451 A1 | 10/2014 | Tengler et al. |
| 2014/0330032 A1 | 11/2014 | Lynch et al. |
| 2014/0357880 A1 | 12/2014 | Brandhorst et al. |

FOREIGN PATENT DOCUMENTS

| | | |
|---|---|---|
| CN | 103080325 B | 8/2014 |
| EP | 1520851 A1 | 4/2005 |
| JP | 2893216 B2 | 5/1999 |
| JP | 2002284753 | * 10/2002 |
| WO | 2012033845 A1 | 3/2012 |
| WO | WO 2013/192451 A1 | 12/2013 |

OTHER PUBLICATIONS

Mitchell et al., Silica gel as a catalyst in the preparation of nitriles. Journal of the American Chemical Society, 1931, 53, 321-330.*
Machine-generated English translation of JP2002284753, published on Oct. 3, 2002.*
Extended European Search Report for European Application No. 17753876.6, dated Sep. 18, 2019, pp. 1-7.
Bedia et al., "A Kinetic Study of 2-propanol Dehydration on Carbon Acid Catalysts", Journal of Catalysis, 2010, vol. 271, pp. 33-42.
Gao et al., "Structure—activity Relationships in NH3-SCR Over Cu-SSZ-13 as Probed by Reaction Kinetics and EPR Studies", Journal of Catalysis, Apr. 2013, vol. 300, pp. 20-29.
Ghaffar et al., "Recent Trends in Lactic Acid Biotechnology: A Brief Review on Production to Purification", Journal of Radiation Research and Applied Sciences, Apr. 2014, vol. 7, No. 2, pp. 222-229.
Guerrero-Pérez et al., "New Reaction: Conversion of Glycerol into Acrylonitrile", Chemistry & Sustainability Energy & Materials (ChemSusChem), 2008, vol. 1, pp. 511-513.
Hofvendahl et al.,"Factors Affecting the Fermentative Lactic Acid Production from Renewable Resources", Enzyme and Microbial Technology, Feb. 2000, vol. 26, No. 2-4, pp. 87-107.
Itagaki et al., "A Monovacant Lacunary Silicotungstate as an Efficient Heterogeneous Catalyst for Dehydration of Primary Amides to Nitriles", ChemCatChem, Jul. 2013, vol. 5, No. 7, pp. 1725-1728.
Kostestkyy et al., "Structure-activity Relationships on Metal-oxides: Alcohol Dehydration", Catalysis Science & Technology, Nov. 2014, vol. 4, No. 11, pp. 3735-4102.

(Continued)

*Primary Examiner* — Po-Chih Chen
(74) *Attorney, Agent, or Firm* — Michael A. McIntyre

(57) ABSTRACT

An aspect of the present disclosure is a method that includes a first reacting a molecule from at least one of a carboxylic acid, an ester of a carboxylic acid, and/or an anhydride with ammonia to form a nitrile, where the first reacting is catalyzed using an acid catalyst. In some embodiments of the present disclosure, the molecule may include at least one of acetic acid, lactic acid, and/or 3-hydroxyproprionic acid (3-HPA). In some embodiments of the present disclosure, the molecule may include at least one of methyl acetate, ethyl lactate, and/or ethyl 3-hydroxypropanoate (ethyl 3-HP). In some embodiments of the present disclosure, the anhydride may be acetic anhydride.

8 Claims, 33 Drawing Sheets

(56) References Cited

OTHER PUBLICATIONS

Kumar et al., "A Continuous Process for the Recovery of Lactic Acid by Reactive Distillation", Journal of Chemical Technology & Biotechnology, 2006, vol. 81, pp. 1767-1777.
Le Nôtre et al., "Biobased Synthesis of Acrylonitrile from Glutamic Acid", Green Chemistry, 2011, vol. 13, pp. 807-809.
Lim et al. "Processing Technologies for Poly(lactic Acid)", Progress in Polymer Science, Aug. 2008, vol. 33, No. 8, pp. 820-852.
Liebig et al., "Glycerol Conversion to Acrylonitrile by Consecutive Dehydration over WO3/TiO2 and Ammoxidation Over Sb-(Fe,V)-O", Applied Catalysis B: Environmental, Mar. 2013, vol. 132-133, pp. 170-182.
Mekki-Berrada et al., "Fatty Acid Methyl Esters into Nitriles: Acid-base Properties for Enhanced Catalysts", Journal of Catalysis, 2013, vol. 306, pp. 30-37.
Orjuela, "A Novel Process for Recovery of Fermentation-derived Succinic Acid", Separation and Purification Technology, 2011, vol. 83, pp. 31-37.
Pasternak et al., "Products of Ammonolysis of Dimethyl Esters of Aliphatic Dicarboxylic Acids", Journal of Applied Chemistry USSR, 1973, vol. 47, No. 11, pp. 2590-2592.
Stevenson, "Ammonolysis", Industrial & Engineering Chemistry, Sep. 1951, vol. 43, No. 9, pp. 1920-1924.
Suvorov et al., "Ammonolysis of Esters of Hydroxybenzoic Acids on a Boron Phosphate Catalyst", Journal of Applied Chemistry USSR, Sep. 10, 1987, vol. 60, No. 3, pp. 677-679.
Vassena, "Nitration of Toluene and Nitrotoluene with Solid Acids", A Dissertation Submitted to the Swiss Federal Institute of Technology Zurich, 2000, Diss. ETH No. 13600, pp. 1-151.
International Search Report and Written Opinion for International (PCT) Application PCT/US17/18272, dated Apr. 25, 2017, pp. 1-9.

\* cited by examiner

1)

2)

3)

SYSTEMS AND METHODS FOR PRODUCING NITRILES

CROSS-REFERENCE TO RELATED APPLICATIONS

This application claims priority to U.S. Provisional Application Nos. 62/297,187 and 62/437,303, filed Feb. 19, 2016 and Dec. 21, 2016 respectively, the contents of which are incorporated herein by reference in their entirety.

CONTRACTUAL ORIGIN

The United States Government has rights in this disclosure under Contract No. DE-AC36-08GO28308 between the United States Department of Energy and the Alliance for Sustainable Energy, LLC, the Manager and Operator of the National Renewable Energy Laboratory.

BACKGROUND

Acrylonitrile (ACN) is one of the most widely used monomers in the chemical industry with applications in the synthesis of many plastics, rubbers, resins, paints, adsorbents, and for the production polyacrylonitrile (PAN) based carbon fibers (CF). As such, ACN is a valued commodity chemical with annual production of approximately 7 million metric tons. The market outlook for ACN is projected to grow by 11-18% driven by increasing interest in using CF in lightweight automotive vehicles and aircraft. Currently, industrial production of ACN is conducted with the SOHIO process, where propylene is converted to ACN via ammoxidation over a bismuth molybdate-based catalyst. First-generation catalysts for the process were developed in the 1950s and achieved yields of ACN from propylene of approximately 55%. This discovery launched the modern ACN industry and spurred decades of research studying reaction mechanisms and advancing catalyst performance to improve ACN yields. However, concerns over propylene price volatility, the environment, sustainability, and climate change have caused researchers to look for alternatives from petroleum-derived propylene to produce ACN. Much work has focused on the ammoxidation of propane, which is a cheaper substrate and has a lower carbon footprint than propylene, but propane is still derived from non-renewable sources. More recently, routes to ACN have been described from renewable feedstocks such as glycerol and glutamic acid. However, improved routes to ACN and other nitriles via bio-derived intermediates are still needed.

SUMMARY

An aspect of the present disclosure is a method that includes a first reacting a molecule from at least one of a carboxylic acid, an ester of a carboxylic acid, and/or an anhydride with ammonia to form a nitrile, where the first reacting is catalyzed using an acid catalyst. In some embodiments of the present disclosure, the molecule may include at least one of acetic acid, lactic acid, and/or 3-hydroxypropionic acid (3-HPA). In some embodiments of the present disclosure, the molecule may include at least one of methyl acetate, ethyl lactate, and/or ethyl 3-hydroxypropanoate (ethyl 3-HP). In some embodiments of the present disclosure, the anhydride may be acetic anhydride.

In some embodiments of the present disclosure, the nitrile may include

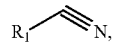

where $R_1$ may be at least one of an alkyl group, an alkenyl group, an alkynyl group, a phenyl group, a carbonyl group, an aldehyde group, a carbonate group, a carboxylic acid group, and/or an ester group. In some embodiments of the present disclosure, $R_1$ may be a vinyl group and the nitrile may be acrylonitrile (ACN). In some embodiments of the present disclosure, $R_1$ may be a methyl group and the nitrile may be acetonitrile. In some embodiments of the present disclosure, the acid catalyst may be a solid acid catalyst. In some embodiments of the present disclosure, the solid acid catalyst may include at least one of $TiO_2$ and/or $ZrO_2$. In some embodiments of the present disclosure, the molecule may be the ester of a carboxylic acid, and the method may further include, prior to the first reacting, a second reacting of the carboxylic acid with an alcohol to produce the molecule and water, where the second reacting of the carboxylic acid regenerates the alcohol.

An aspect of the present disclosure is a method including esterifying a carboxylic acid with an alcohol to produce an ester and water, and nitrilating the ester to produce a nitrile, the alcohol, and water, where the nitrilating is performed by reacting the ester with ammonia over a first acid catalyst. In some embodiments of the present disclosure, the nitrilating may be performed with both the ester and the ammonia in the gas phase. In some embodiments of the present disclosure, the esterifying may be performed by contacting the carboxylic acid and the alcohol with a mineral acid. In some embodiments of the present disclosure, the nitrilating may be performed at an ester to ammonia molar ratio between 1:1 and 10:1. In some embodiments of the present disclosure, the method may further include, after the esterifying, dehydrating a hydroxylated ester to produce an unsaturated ester, where the carboxylic acid may be hydroxylated, the ester may be the hydroxylated ester, and the nitrile may include an alkenyl group. In some embodiments of the present disclosure, the dehydrating and the nitrilating may be performed at substantially the same time.

An aspect of the present disclosure is a system that includes a nitrilation unit containing a first acid catalyst, a feed stream, an ammonia stream, and a product stream, where the feed stream includes at least one of a carboxylic acid, an ester of a carboxylic acid, and/or an anhydride, the product stream includes

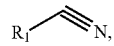

where $R_1$ is at least one of an alkyl group, an alkenyl group, an alkynyl group, a phenyl group, a carbonyl group, an aldehyde group, a carbonate group, a carboxylic acid group, and/or an ester group, and the product stream is formed by passing the feed stream over the first acid catalyst. In some embodiments of the present disclosure, the method may further include a distillation unit, a carboxylic acid stream containing the carboxylic acid, and an alcohol stream, where the carboxylic acid stream and the alcohol stream may be fed to the distillation unit, and the carboxylic acid stream and alcohol stream may react in the distillation unit to form the feed stream containing the ester of the carboxylic acid.

In some embodiments of the present disclosure, the system may further include a dewatering unit and a filtered broth stream containing water and the dicarboxylic acid, where the filtered broth stream may be fed to the dewatering unit, and the dewatering unit may remove at least a portion of the water from the filtered broth stream to form the carboxylic acid stream. In some embodiments of the present disclosure, the dewatering unit may include an adsorption column containing an adsorbent that selectively adsorbs at least a portion of the carboxylic acid. In some embodiments of the present disclosure, the adsorbent may be polybenzimidazole.

In some embodiments of the present disclosure, the system may further include a filter unit and a broth stream containing at least one of cells, debris, proteins, and the carboxylic acid, where the broth stream may be fed to the filter unit, the filter unit may remove at least one of the cells, the debris, and/or the proteins to form the filtered broth stream, and the filter unit may form a by-product stream containing at least one of the cells, the debris, and/or the proteins. In some embodiments of the present disclosure, the system may further include a fermenter, where the fermenter produces the carboxylic acid, resulting in the broth. In some embodiments of the present disclosure, the carboxylic acid may be produced by *Escherichi coli* metabolizing a sugar.

REFERENCE NUMERALS

100 . . . reaction scheme
110 . . . carboxylic acid
112 . . . dicarboxylic acid
114 . . . anhydride
120 . . . alcohol
130 . . . ester
140 . . . water
150 . . . ammonia ($NH_3$)
160 . . . nitrile
170 . . . acid catalyst
200 . . . method
210 . . . esterifying
220 . . . dehydrating
230 . . . nitrilating
300 . . . system
310 . . . fermenter
312 . . . broth
320 . . . filter
322 . . . cells and debris
324 . . . proteins
326 . . . filtered broth
330 . . . adsorption unit
332 . . . spent carbon
334 . . . decolored broth
340 . . . dewatering unit
342 . . . dewatered salts
350 . . . salt-dissolving unit
352 . . . sugars
354 . . . alcohol mixture
360 . . . salt-breaking unit
362 . . . acid
364 . . . salts
366 . . . 3-HPA/alcohol stream
370 . . . esterification reactor
372 . . . ethyl 3-HP/alcohol stream
380 . . . distillation unit
382 . . . ethyl 3-HP stream
400 . . . reactive distillation unit
410 . . . 3-HPA stream in alcohol
415 . . . alcohol stream
417 . . . ethyl acrylate stream
420 . . . nitrilation unit
422 . . . ammonia
424 . . . inert
426 . . . ACN

BRIEF DESCRIPTION OF THE DRAWINGS

Exemplary embodiments are illustrated in referenced figures of the drawings. It is intended that the embodiments and figures disclosed herein are to be considered illustrative rather than limiting.

DETAILED DESCRIPTION

It is contemplated that some embodiments as disclosed herein may prove useful in addressing problems and deficiencies in a number of technical areas related to the production of acrylonitrile (ACN) and other nitriles using raw materials derived from biomass and/or other sources. However, the embodiments described herein should not necessarily be construed as limited to addressing any of the particular problems or deficiencies discussed herein.

ACN is a prominent monomer used for the production of polymers, including the production of plastics and carbon fiber chemicals. However, it is primarily derived from nonrenewable propylene via ammoxidation, which generates hazardous by products including hydrogen cyanide. In addition the reaction is exothermic with runaway potential and often requires complex and expensive catalysts. In some embodiments of the present disclosure, carboxylic acids and/or esters may be derived from microbial fermentation and converted into renewable nitriles, although petroleum-derived sources of carboxvlic acids and/or esters may also be used as a source to produce nitriles. As used herein, the term "nitrile" refers to any organic compound having a —C≡N functional group. In some embodiments of the present disclosure a nitrile may be produced from a starting a C3-carboxylic acid such as 3-hydroxyproprionic acid (3-HPA) and/or lactic acid, by esterification of the C3-carboxylic acid with an alcohol to produce an ester, followed by dehydration and nitrilation of the esters to produce ACN. In some embodiments of the present disclosure, nitrilation to produce ACN and/or other nitriles may occur substantially in a single reaction step and/or in more than one reaction step occurring in rapid succession. In some embodiments of the present disclosure, the nitrilation may include one or more intermediate steps, for example, formation of an amide group on the ester, followed by dehydration of the amide to a nitrile group.

Figure 1A:
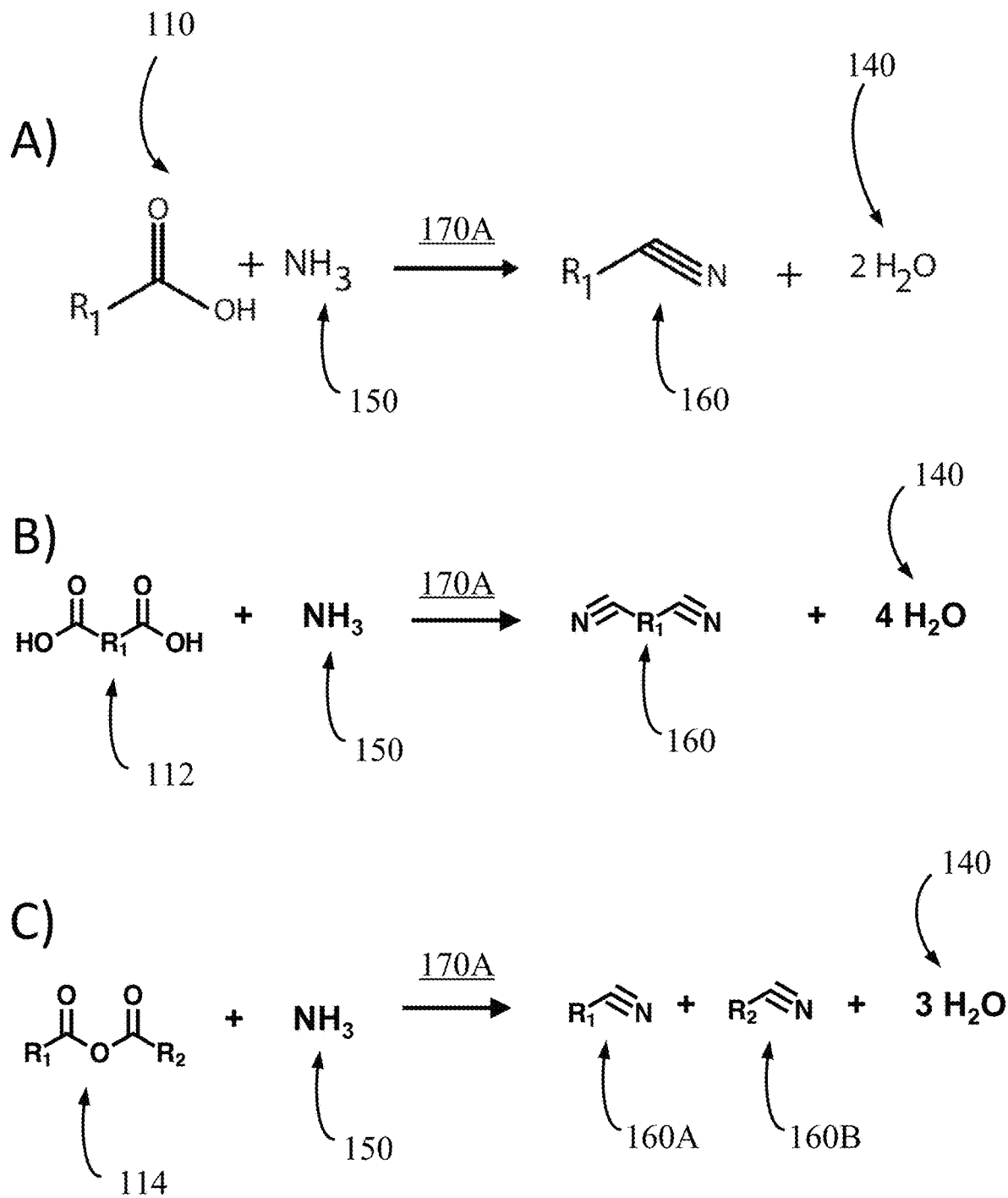
FIG. 1A illustrates reactions for the direct conversion of carboxylic acids, dicarboxylic acids, and anhydrides to nitriles, according to some embodiments of the present disclosure.

FIG. 1A illustrates three reactions for directly converting various molecules directly to nitriles by reacting the molecules with ammonia over an acid catalyst. For example, reaction A) involves reacting a carboxylic acid 110 with ammonia 150 to produce a nitrile 160 and water 140 where the reaction is catalyzed using an acid catalyst 170. Reaction B) of FIG. 1A involves reacting a dicarboxylic acid 112 with ammonia 150 to produce a nitrile 160, in this case a di-nitrile, and water 140 where the reaction is catalyzed using an acid catalyst 170. Finally, reaction C) involves reacting an anhydride 114 with ammonia 150 to produce a first nitrile 160A and a second nitrile 160B and water 140 where the reaction is catalyzed using an acid catalyst 170. Thus, some embodiments of the present disclosure relate to a single, acid catalyzed nitrilation reaction that converts at least one molecule including a carboxylic acid, a dicarboxylic acid, and/or an anhydride to at least one nitrile and water by reacting the at least one molecule with ammonia. A carboxylic acid 110 may terminate with an $R_1$ group and an anhydride 114 may terminate with an $R_1$ and/or $R_2$ group, where $R_1$ and/or $R_2$ may be a variety of organic functional groups including an alkyl group, an alkenyl group, an alkynyl group, a phenyl group, a carbonyl group, an aldehyde group, a carbonate group, a carboxylic acid group, and/or an ester group. Similarly, a dicarboxylic acid 112 may include any desirable connecting group $R_1$, including an alkane and/or an alkene, linear and/or branched. Any of the reactions (A-C) of FIG. 1A may be catalyzed by an acid catalyst 170A, for example a solid acid catalyst. Examples of solid acid catalysts include at least one of a clay mineral (e.g. montmorillonite and/or zeolites), a metal oxide (e.g. $Al_2O_3$), a metal sulfide (e.g. ZnS), a metal salt (e.g. $MgSO_4$), a mixed oxide ($SiO_2$—$Al_2O_3$), a sulfate-promoted metal oxide (e.g. $SO_4^{2-}/ZrO_2$), a mounted acid (suitable carriers like porous oxides, graphite, metal salts, treated or combined with liquid acids, for example $H_2SO_4/SiO_2$), a cation exchange resin (e.g. Amberlyst® 15), a perfluorinated polymeric sulphuric acid (e.g. Nafion™), and/or a heteropolyacid (e.g. 12-tungstophosphoric acid. $H_3[PW_{12}O_{40}]$). Thus, any suitable solid acid catalyst 170A may be used to catalyze the nitrilation reactions A), B), and/or C) illustrated in FIG. 1A.

Figure 1B:
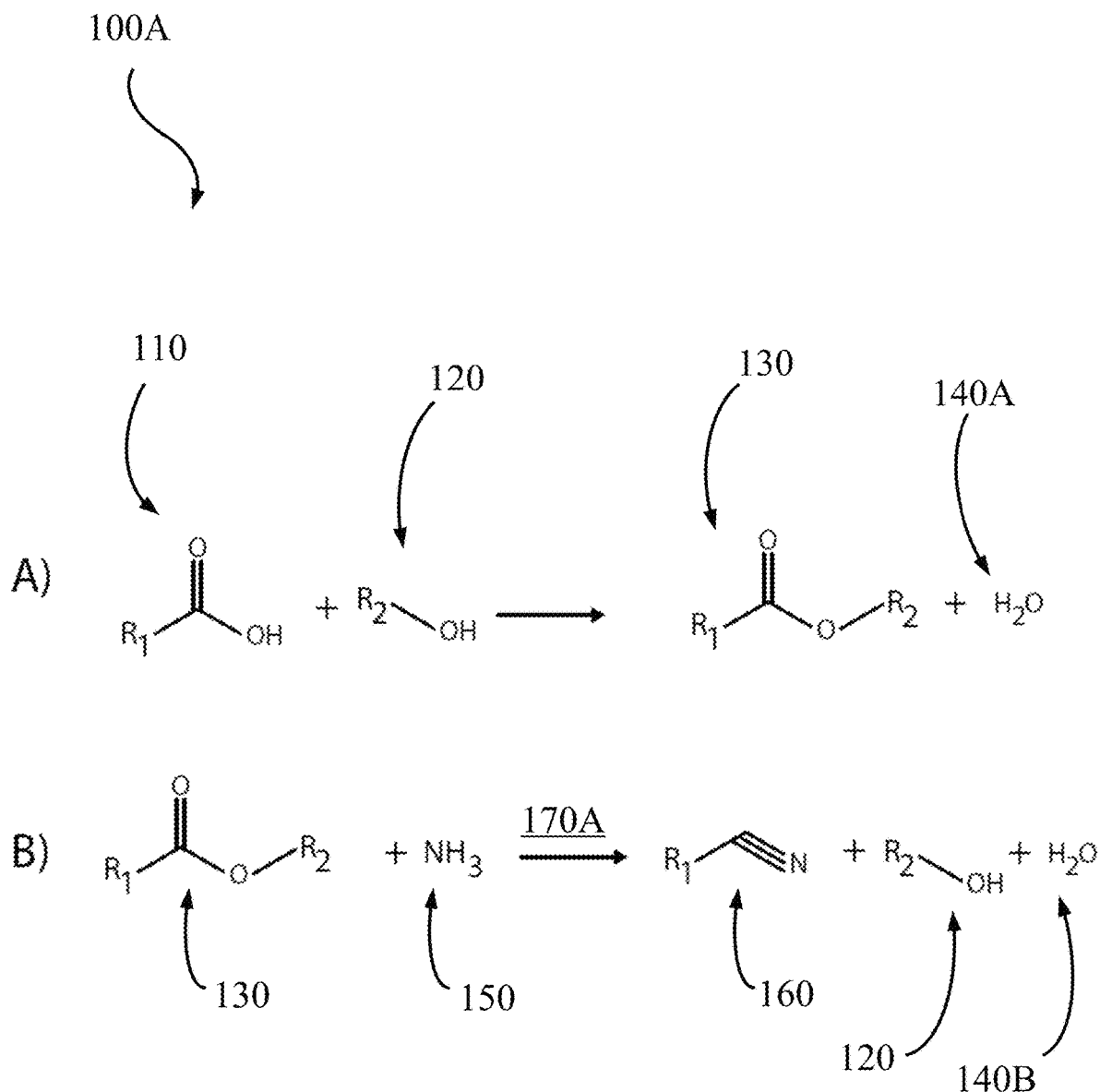
FIG. 1B illustrates a reaction scheme for converting esters and/or carboxylic acids to nitriles, according to some embodiments of the present disclosure.

However, in some situations handling of a carboxylic acid, dicarboxylic acid, and/or an anhydride may be difficult or even dangerous (e.g. potentially explosive). Thus, FIG. 1B illustrates an example of an alternative reaction scheme for producing a nitrile that may involve an intermediate step for converting a carboxylic acid and/or dicarboxylic acid to an ester, which may then be subsequently nitrilated, according to some embodiments of the present disclosure. Referring to FIG. 1B, two reactions, A) and B), are shown as part of the reaction scheme 100A, where reaction A) is an esterification reaction and reaction B) is a nitrilation reaction. The esterification reaction A) reacts a carboxylic acid 110 with an alcohol 120 to form an ester 130 and water 140A. As shown in FIG. 1B, the carboxylic acid 110 may terminate with an $R_1$ group, which may be a variety of organic functional groups including an alkyl group, an alkenyl group, an alkynyl group, a phenyl group, a carbonyl group, an aldehyde group, a carbonate group, a carboxylic acid group, and/or an ester group. The alcohol 120 may be any suitable alcohol that allows the esterification reaction to proceed including at least one of a primary alcohol, a secondary alcohol, and/or a tertiary alcohol, with examples of primary alcohols including methanol, ethanol, propanol, butanol, pentanol, hexanol, and/or octanol. Thus, the alcohol 120 may be generalized as shown in FIG. 1B to be a hydroxyl group attached to an $R_2$ group where the $R_2$ group may be any suitable organic functional group including an alkyl group, an alkenyl group, an alkynyl group, and/or a phenyl group. Thus, in some embodiments of the present disclosure $R_1$ and $R_2$ may be the same functional group, or $R_1$ and $R_2$ may be different functional groups. In general, the esterification reaction A) condenses the carboxylic acid 110 with the alcohol 120 resulting in the formation of the ester 130, now containing the $R_2$ group, and the formation of a first water molecule 140A.

Referring again to FIG. 1B, the ester 130 may then proceed to the nitrilation reaction B) to produce the nitrile 160. In the nitrilation reaction B), the ester 130 reacts with ammonia 160 such that both oxygen atoms of the ester 130 are removed to form the nitrile 160, also resulting in the regeneration of the alcohol 120 originally used in the esterification reaction A), and the formation of a second water molecule 140B. The regenerated alcohol 120 may be separated from the nitrile 160 and/or the water 140 and subsequently recycled back to the esterification reaction A). In some embodiments of the present disclosure, the reaction scheme 100A illustrated in FIG. 1B may begin with an ester 130, a carboxylic acid 110, and/or a mixture of the two to produce the nitrile 160. The nitrilation reaction B) may be performed in acidic conditions to catalyze the reaction. Thus, the nitrilation reaction B) may be catalyzed by an acid catalyst 170A, for example at least one solid acid catalyst such as at least one of a clay mineral (e.g. montmorillonite and/or zeolites), a metal oxide (e.g. $Al_2O_3$), a metal sulfide (e.g. ZnS), a metal salt (e.g. $MgSO_4$), a mixed oxide ($SiO_2$—$Al_2O_3$), a sulfate-promoted metal oxide (e.g. $SO_4^{2-}/ZrO_2$), a mounted acid (suitable carriers like porous oxides, graphite, metal salts, treated or combined with liquid acids, for example $H_2SO_4/SiO_2$), a cation exchange resin (e.g. Amberlyst® 15), a perfluorinated polymeric sulphuric acid (e.g. Nafion™), and/or a heteropolyacid (e.g. 12-tungstophosphoric acid. $H_3[PW_{12}O_{40}]$). Thus, any suitable solid acid catalyst 170A may be used to catalyze the nitrilation reaction A) illustrated in FIG. 1B.

Figure 1C:
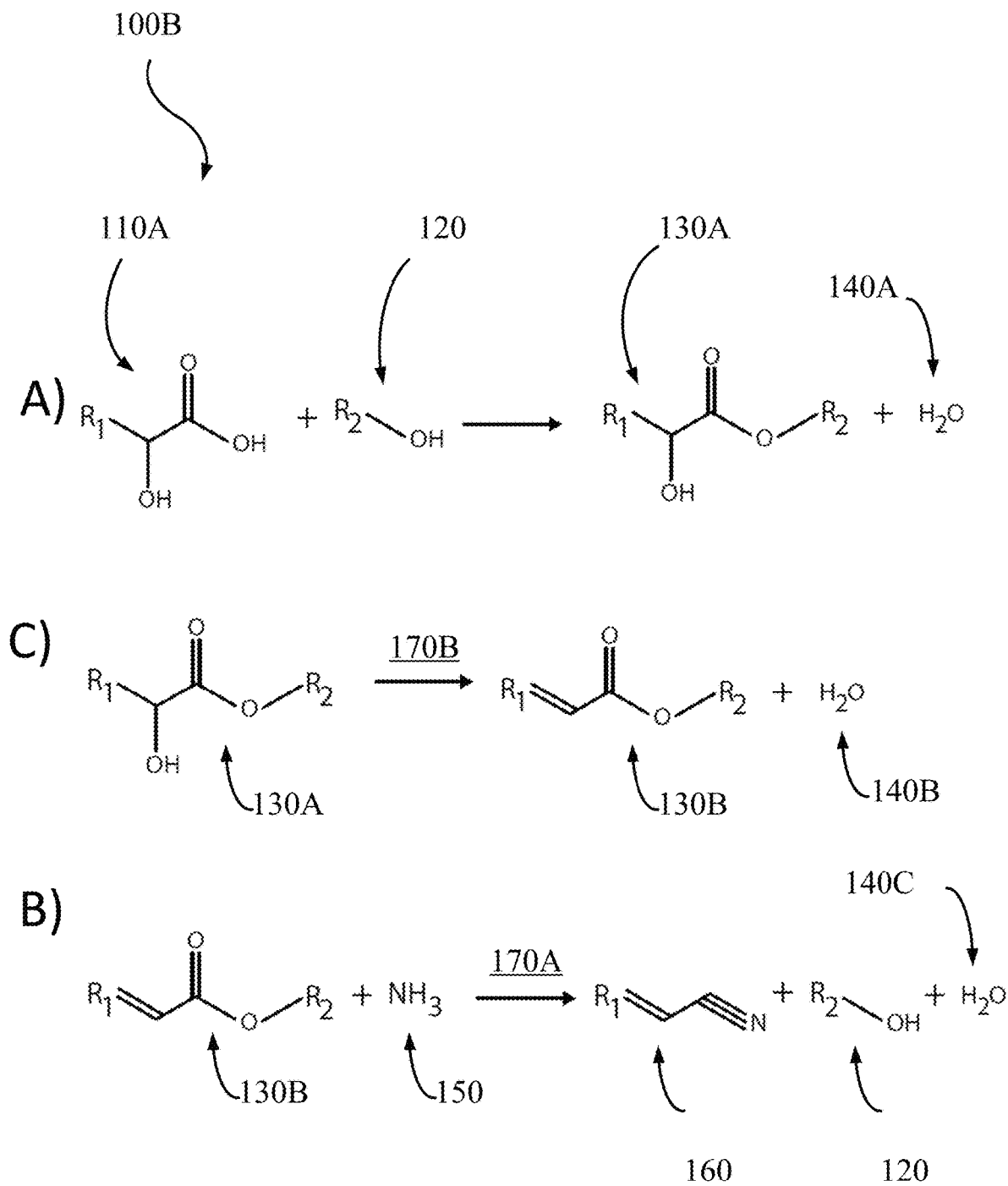
FIG. 1C illustrates a reaction scheme for converting hydroxylated carboxylic acids, hydroxylated esters, and/or unsaturated esters to nitriles, according to some embodiments of the present disclosure.

FIG. 1C illustrates a second reaction scheme 100B for producing a nitrile 160, according to some embodiments of the present disclosure. In this example, the reaction scheme 100B includes three reactions A), B), and C) where, as in FIG. 1B, reaction A) is an esterification reaction and reaction B) is a nitrilation reaction. Thus, scheme 100B, like scheme 100A, may begin with the esterification of a carboxylic acid 110, in this case a hydroxylated carboxylic acid 110A. This illustrates that the esterification reaction A) may react a functionalized carboxylic acid, e.g. a hydroxylated carboxylic acid 110A, with an alcohol 120 to form a functionalized ester, e.g. a hydroxylated ester 130A. Thus, in the example of FIG. 1C, the carboxvlic acid 110A has a hydroxyl group at the second carbon atom (C2), where the first carbon atom (C1) refers to the carboxylic acid group's carbon atom. In addition, the hydroxylated carboxylic acid 110A may terminate with an $R_1$ group that includes the third carbon atom (C3) of the hydroxylated carboxvlic acid 110A. As described above, the $R_1$ group may be a variety of organic functional groups including an alkyl group, an alkenyl group, an alkynyl group, a phenyl group, a carbonyl group, an aldehyde group, a carbonate group, a carboxylic acid group, and/or an ester group. The alcohol 120 may be any alcohol suitable that allows the esterification reaction to proceed including at least one of a primary alcohol, a secondary alcohol, and/or a tertiary alcohol. The esterification reaction A) may condense the hydroxylated carboxylic acid 110 with the alcohol 120 resulting in the formation of the hydroxylated ester 130A, now containing the $R_2$ group, and also resulting in the formation of a first water molecule 140A.

The hydroxylated ester 130A may then proceed to the dehydration reaction C), in which the hydroxyl group at the C2 position is removed to form a carbon-carbon double-bond between the C2 and C3 carbon atoms, resulting in the formation of an unsaturated ester 130B (e.g. an acrylate ester), and also resulting in the formation of a second water molecule 140B. The dehydration reaction C) illustrates that various esters may be processed to form other intermediate esters that may be subsequently converted to nitriles. According to some embodiments of the present disclosure, the dehydration reaction C) may be performed in acidic conditions to catalyze the reaction. Thus, an acid catalyst 170B may be provided to the dehydration reaction C), where the acid catalyst may be in a liquid form and/or a solid form. In some embodiments of the present disclosure, the acid catalyst 170B may be a liquid acid catalyst including any suitable organic acid and/or inorganic acid, with examples include hydrochloric acid, sulfuric acid, and/or phosphoric acid. In some embodiments of the present disclosure, the acid catalyst 170B used in the dehydration reaction C) may be a solid acid catalyst with examples including a clay, a zeolite, a metal oxide, a phosphated metal oxide, a metal sulfide, a mounted acid, a perfluorinated polymeric sulfuric acid (e.g. sulfated zirconia, sulfated niobia, etc.), an amphoteric oxide (e.g. $CeZrO_2$, $MgAlO_2$, doped oxides, etc.), a heteropolyacid, and/or any other suitable solid acid catalyst.

Referring again to FIG. 1C, the acrylate ester 130B may then rapidly proceed and/or substantially simultaneously proceed through the nitrilation reaction B) in which the acrylate ester 130B reacts with ammonia 150 to form the nitrile 160 having an alkenyl group (the carbon-carbon double bond), and also resulting in the regeneration of the alcohol 120 originally used in the esterification reaction A), and the formation of a third water molecule 140C. As described above, the nitrilation reaction B) may be performed in acidic conditions to catalyze the reaction, e.g. using an acid catalyst 170A. Therefore, the nitrilation reaction B) may be catalyzed using the same acid catalyst that is used to catalyze the dehydration reaction C) described above. Alternatively, or in addition to, at least a portion of the nitrilation reaction B) may be accomplished using a different acid catalyst than the acid catalyst 170B used in the dehydration reaction C). The regenerated alcohol 120 may be separated from the nitrile 160 and/or the water 140 and subsequently recycled to the esterification reaction A). In some embodiments of the present disclosure, the reaction scheme 100B of FIG. 1C may begin with a hydroxylated ester 130A such that only the dehydration reaction C) and the nitrilation reaction B) occur in a single reactor bed to produce the nitrile 160. In some embodiments of the present disclosure, reaction scheme 100B may begin with an acrylate ester 130B such that only the nitrilation reaction B) is needed to produce the nitrile 160. In some embodiments of the present disclosure, the reaction scheme 100B may begin with the dehydration of a hydroxylated carboxylic acid 110A such that the hydroxyl group is removed to form a carbon-carbon double bond and water, resulting in an unsaturated carboxylic acid (not shown). The unsaturated carboxylic acid may then be esterified to produce an acrylate ester 130B, followed by nitrilation of the acrylate ester 130B to produce the final nitrile 160 product. Thus, in some embodiments of the present disclosure, not all of the reactions shown in FIG. 1C need occur to produce a nitrile, the reactions need not necessarily be performed in the exact sequential order shown in reaction scheme 100B, and/or the reactions may occur substantially simultaneously and/or in rapid succession in single reactor bed.

Figure 2:
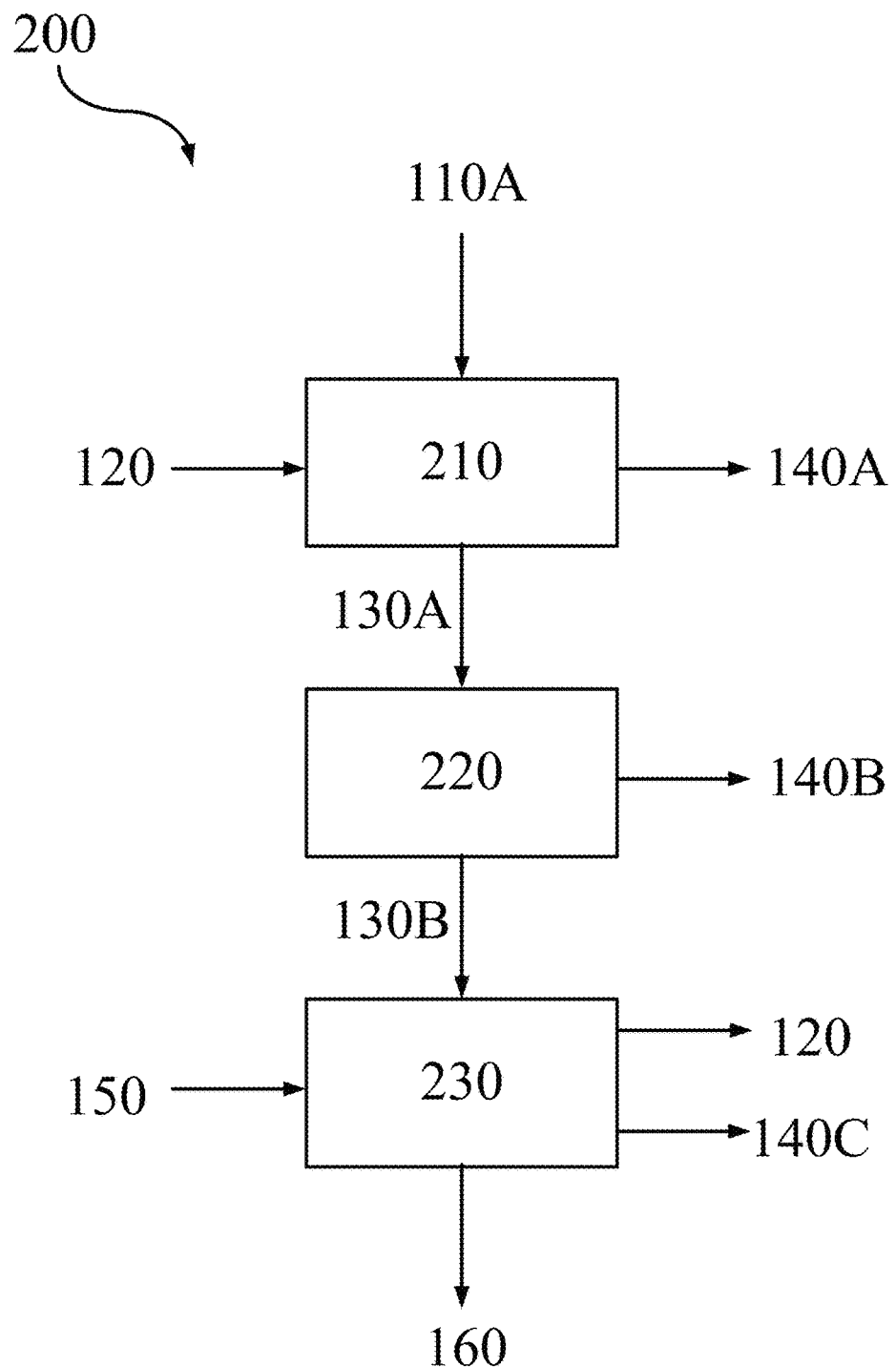
FIG. 2 illustrates a method for converting esters and/or carboxylic acids to nitriles, according to some embodiments of the present disclosure.

FIG. 2 illustrates a method 200 for converting a carboxylic acid 110, in this example a hydroxylated carboxylic acid 110A, to a nitrile 160 as shown in FIG. 1C and according to the chemistry described above. The hydroxylated carboxylic acid 110A may be derived from biomass, for example, from a fermentation process (not shown) and/or a thermal degradation process (not shown) (e.g. gasification and/or pyrolysis) that utilize a lignocellulosic-containing feed material such as agricultural waste, residential waste, etc. These types of lignocellulosic degradation processes typically yield a mixture of molecules and require at least one separation unit operation to yield specific target molecules with examples of separation unit operations including distillation, liquid-liquid extraction, adsorption and/or any other suitable unit operation known to those skilled in the art. Thus, a separation process (not shown) may yield in sufficient quantity and purity a targeted carboxylic acid, in this example a hydroxylated carboxylic acid 110A (or other starting molecule; e.g. an ester) that may be reacted according to the reaction schemes (100A and/or 100B) described above. In some embodiments of the present disclosure, the method 200 for producing the "target" nitrile 160 may begin by esterifying 210 the hydroxylated carboxylic acid 110A with an alcohol 120 in a first reactor, in this example by esterifying 210 a hydroxylated carboxylic acid 110A. The esterification, regardless of whether or not the carboxylic acid 110 is functionalized, may be accomplished in a CSTR using a mineral acid (e.g. sulfuric acid) as an esterification catalyst (not shown). Typical reaction conditions may include a solution of 50 wt % alcohol, or between 30 wt % and 80 wt % alcohol, or between 46 wt % and 48 wt % alcohol, between 30 wt % and 80 wt %, hydroxylated acid, between 1 wt % and 10 wt % mineral acid, performed in a CSTR with a residence time of ~3 hr, or between 1 hr and 10 hr, at a temperature of 90° C., or between 50° C. and 150° C. The product stream of the CSTR may be fed to the middle of a distillation column (not shown) where a ternary azeotrope containing water, acrylate ester or ester, and alcohol may be recovered in the overhead of the column. Reactive distillation methods may also be employed using acid catalysts, including solid acid catalysts (e.g. Amberlyst® 15) where the solid acid and alcohol solution may be heated in the bottom (e.g. high temperature and high pressure zone) of a distillation column such that the resultant vapors are passed upwards through the lower temperature and pressure zones of the distillation column containing the solid acid catalyst. The resultant ester product may then then be recovered in the column overhead (e.g. lowest temperature and lowest pressure zone of the distillation column). As esterification reactions are equilibrium reactions, the water 140A produced may be removed as the carboxylic acid 110 is esterified, also potentially by distillation and/or reactive distillation, for example by the use of drying salts, molecular sieves, the use of an entrainer, and/or through phase separation esterification reactions with long chain hydrophobic alcohols.

Referring again to FIG. 2, for the example of a hydroxylated ester 130A resulting from the esterifying 210 of a hydroxylated carboxylic acid 110A, the hydroxylated ester 130A may be fed to a second reactor for dehydrating 220 the hydroxylated ester 130A to form an acrylate ester 130B. In some embodiments of the present disclosure, the dehydrating 220 may be accomplished in the same reactor as the esterifying 210. As described above, dehydrating 220 the hydroxylated ester 130A may be accomplished by contacting the hydroxylated ester 130A with an acid catalyst (not shown). In some embodiments of the present disclosure, dehydrating 220 the hydroxylated ester 130A may be accomplished by feeding the hydroxylated ester 130A to a packed-bed reactor containing an inert packing of glass beads or a solid acid catalyst such as metal oxides (e.g. titania, zirconia, niobia, alumina, etc.) held at a temperature between 100° C. and 350° C. with a contact time between 0.1 seconds and 4 seconds, and a WHSV (weight hourly space velocity) between 0.1 $hr^{-1}$ and 1 $hr^{-1}$. In some embodiments of the present disclosure, dehydrating 220 the hydroxylated ester 130A to form the acrylate ester 130B may be accomplished by feeding the hydroxylated ester 130A to a stirred-tank reactor containing at least one of a solid acid catalyst and/or a liquid acid catalyst for either batch and/or continuous modes of operation as described above. Thus, these reactions may be completed in at least one of a liquid phase and/or a gas phase, and may be performed in a reactive distillation column.

The acrylate ester 140B resulting from dehydrating 220 the hydroxylated ester 130B may then simultaneously and/or successively proceed to a nitrilating 230 step achieved by contacting the acrylate ester 130B and ammonia 150. In some cases, as described above, the same acid catalyst (not shown) used for dehydrating 220 the hydroxylated ester 130A may used for the nitrilating 230 to form the target nitrile 160. Thus, nitrilating 230 the acrylate ester 130B may be accomplished in the same reactor used for dehydrating 220 the hydroxylated ester 130A as described above. The nitrilating 230 may be accomplished with the reactants in at least one of the gas phase and/or the liquid phase. In some embodiments of the present disclosure, nitrilating 230 the acrylate ester 130B to form the nitrile 160 may be accomplished by providing a packed-bed reactor having a first zone for dehydrating 220 the hydroxylated ester 130A to produce the acrylate ester 130B, followed by a second zone in the packed-bed reactor for nitrilating 230 the acrylate ester 130B to produce the nitrile 160. The first zone and the second zone may have different operating conditions, for example, the dehydrating 230 may be accomplished at a first temperature and the nitrilation 230 may be performed at a second temperature that is higher than the first temperature, for example with the first temperature between 100° C. and 300° C., and the second temperature between 250° C. and 400° C. In some embodiments of the present disclosure, the same packed bed and/or CSTR reactor and/or acid catalyst may be used to complete both the dehydrating 220 of the hydroxylated ester 130A and the nitrilating 230 of the acrylate ester 130B. In some embodiments of the present disclosure, a first reactor may be used for dehydrating 220 the hydroxylated ester 130A, and a second reactor may be used for nitrilating 230 the acrylate ester 130B resulting in the production of the nitrile 150.

In some embodiments of the present disclosure, C3 carboxylic acids (e.g. lactic acid, 3-hydroxyproprionic acid (3-HPA), acrylic acid) may be reacted with varying chain-length alcohols (e.g. methanol, ethanol, propanol, butanol, pentanol, hexanol, and/or octanol) via at least one esterification reaction to produce esters, in some examples hydroxylated esters and/or unsaturated esters (e.g. acrylate esters). In some embodiments of the present disclosure, the alcohols may also be used as an extraction solvent to simultaneously remove carboxylic acids from a fermentation broth, and/or to process neat carboxylic acids already recovered from fermentation. As described above, the resultant esterified C3 molecules may be reacted with ammonia gas to form a nitrile, in this case ACN. As described above, potential catalysts for dehydration and/or nitrilation include liquid acids and/or solid acids such as acidic resins, acid oxides, amphoteric oxides, metal phosphatides, and/or zeolites.

Lactic acid may be produced at the industrial scale via the fermentation of sugars with engineered and wild type microorganisms. Titers may reach approximately 100 g/L at productivities of about 1 g/L/hr to about 3 g/L/hr. Additionally, low pH fermentations with engineered microorganisms may be employed (pH≤4), which greatly aids in achieving economical separation of the acid from the broth. The main use for lactic acid is in the production of poly(lactic acid) (PLA). However, the ester derivatives of these acids may also be economically separated from the fermentation broth at yields of >95% via esterification utilizing methods such as reactive distillation and/or phase separation combined with esterification of a hydrophobic alcohol, and/or through other esterification methods. The resultant lactate ester may then be hydrolyzed back to produce the free acid. However, the process described herein uses directly the ester derivatives of lactic acid and/or 3-HPA as substrates for the nitrilation reaction to produce ACN with the simultaneous recovery of the alcohol for recycle back to the esterification/separation unit operation.

Similar to lactic acid, the production of 3-HPA from the fermentation of sugars may be achieved at the industrial scale. Titers may reach approximately 50 g/L at productivities greater than about 0.5 g/L/hr. 3-HPA is more difficult than lactic acid to separate from fermentation broth due to the tendency of 3-HPA to self-esterify at higher concentrations (greater than about 30 wt %). However, the ester derivatives of 3-HPA are stable and may be readily separated with high yields and purities through the same methods described above for lactic acid. Coupling of the nitrilation reaction to the separation of 3-HPA esters from fermentation broth may be particularly synergistic given the difficulties present in separating the free acid and the ability of this reaction to recover the alcohol for recycle back to the separation operation.

Schemes 1) and 2) below illustrate two reaction schemes for producing ACN from 3-HPA, for example bio-based 3-HPA.

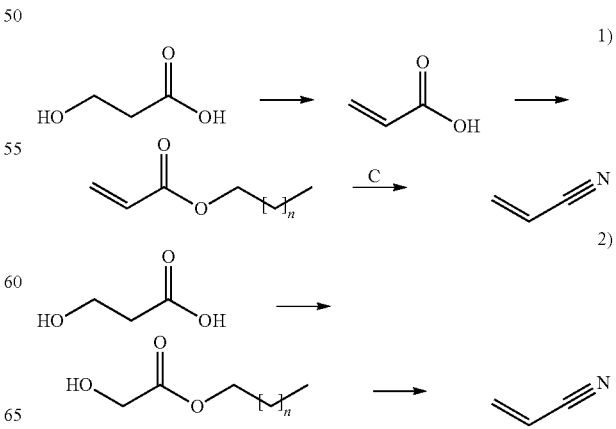

Scheme 1) illustrates a 3-step process to produce ACN beginning with the dehydration of 3-HPA to produce the double-bond containing acrylic acid and the by-product water. The acrylic acid may then proceed through the second reaction, esterification of the acrylic acid, to produce an acrylate ester. The acrylate ester may then be reacted a third step, nitrilation, to produce the targeted final product ACN. Neat acrylate ester may be volatilized at temperatures greater than about 100° C. into an inert carrier gas (nitrogen, argon, etc.) and passed over a solid acid catalyst with contact times between 0.1 seconds and about 10 seconds, WHSVs between 1 and 10, GHSVs (gas hourly space velocity) between 1000 and 10,000, at reactor temperatures between 250° C. and 400° C. The reactions may be performed at atmospheric pressure and/or at slightly elevated pressures up to about 4 atmospheres (pressures in absolute units). Suitable solid acid catalysts, as described above, include zeolites, amphoteric oxides, solid acid resins, and/or solid acid oxides including but not limited to alumina, titania, niobia, zirconia, etc. An increased molar ratio of ammonia to ester may improve yield and may maintain catalyst activity for longer periods of time. The reaction may be run at 1:1 ammonia to ester molar ratio, an 8:1 ammonia to ester molar ratio, or up to a 10:1 or higher ammonia to ester molar ratios. In some embodiments of the present disclosure, the solid acid catalyst may be regenerated to restore high ACN yielding activity. Regeneration of the solid acid catalyst may be performed by flowing oxygen ($O_2$) diluted in an inert carrier gas at concentrations up to about 20% w/w of oxygen over the solid acid catalyst at temperatures greater than about 400° C. for as little as 5 minutes. Air may also be used to regenerate the solid acid catalyst following the same method. Overall, Scheme 1) results in the formation of ACN, water, and an alcohol. Scheme 2) summarizes a two-step process for producing ACN, beginning with the esterification of 3-HPA to produce its ester and water, followed by the essentially simultaneous dehydration and nitrilation of the ester to produce ACN. As described above, solid acid catalysts suitable for Schemes 1 and 2 above may include clay minerals (e.g. montmorillonite and/or zeolites), metal oxides (e.g. $Al_2O_3$), metal sulfides (e.g. ZnS), metal salts (e.g. $MgSO_4$), mixed oxides ($SiO_2$—$Al_2O_3$), sulfate-promoted metal oxides and mixed oxides (e.g. $SO_4^{2-}/ZrO_2$), mounted acids (suitable carriers like porous oxides, graphite, metal salts, treated or combined with liquid acids, for example $H_2SO_4/SiO_2$), cation exchange resins (e.g. Amberlyst® 15), perfluorinated polymeric sulphuric acid (e.g. Nafion™), and/or heteropolyacids (e.g. 12-tungstophosphoric acid, $H_3[PW_{12}O_{40}]$).

Figure 3:
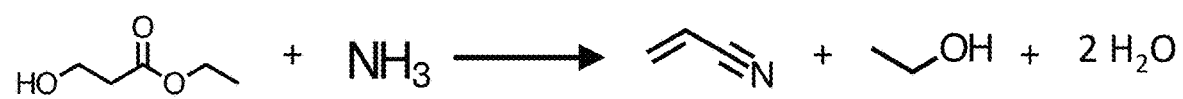
FIG. 3 illustrates a reaction scheme for producing converting ethyl 3-hydroxypropanoate (ethyl 3-HP) to ACN, according to some embodiments of the present disclosure.
Figure 3:
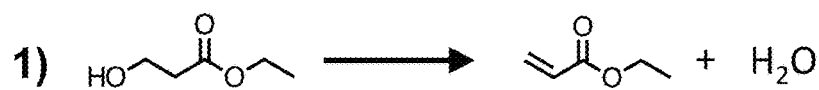
Figure 3:
Figure 3:
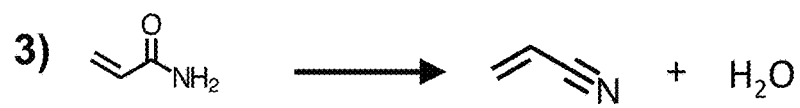

FIG. 3 illustrates another reaction scheme for producing ACN from 3-HPA, in this case beginning with the ethyl ester of 3-HPA, ethyl 3-HP, according to some embodiments of the present disclosure. The overall reaction, shown on top, proceeds through three reactions. In this example, bio-based 3-HPA (a carboxylic acid) may be separated from a fermentation broth via an esterification approach as described above, resulting in the conversion of the 3-HPA to the ethyl 3-HP and/or some other ester if another alcohol other than ethanol is used. The ethyl 3-HP may then be processed in two sequential catalytic beds where dehydration of the ethyl 3-HP may occur over a solid acid catalyst in a first catalytic bed to produce an acrylate ester and water, as shown in reaction 1) of FIG. 3. The acrylate ester and water may then be mixed with ammonia in a molar ratio of about 1:1 to about 10:1 $NH_3$:ester and passed over a second sequential catalytic bed packed with a solid acid catalyst to produce ACN, an alcohol (e.g. ethanol), and water, through reactions 2) and 3) of FIG. 3. Alternatively, the ethyl 3-HP may be volatilized into an inert carrier gas, mixed with ammonia in a molar ratio of about 1:1 to about 10:1 $NH_3$:ester and passed over a single catalytic bed packed with a solid acid catalyst to undergo the three reactions shown in FIG. 3 in a single reaction to produce ACN, the alcohol (e.g. ethanol), and water.

FIG. 3 illustrates generally that ACN may be produced by reacting a C3 ester (e.g. ethyl 3-HP) with ammonia, where an ester is defined as,

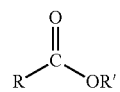

and where for the ester compound of 3-HPA shown in FIG. 3, R is an ethanol functional group, and R' is an ethyl group. Thus, any suitable ester of 3-HPA may be used in the reactions illustrated in FIG. 3 to produce ACN, for example methyl 3-hydroxypropanoate, propyl 3-hydroxypropanoate, butyl 3-hydroxypropanoate, etc. Similarly, referring to Scheme 3 below, lactic acid may also be used the starting compound to produce ACN. Similarly, the carboxylic acid group of lactic acid may also be converted to an ester, and again, the ester may be any suitable ester where R' may be for example, a methyl group, an ethyl group, a propyl group, etc. or any other suitable functional group. Solid catalysts suitable for the reactions shown in FIG. 3 may include clay minerals (e.g. montmorillonite and/or zeolites), metal oxides (e.g. $Al_2O_3$), metal sulfides (e.g. ZnS), metal salts (e.g. $MgSO_4$), mixed oxides ($SiO_2$—$Al_2O_3$), sulfate-promoted metal oxides and mixed oxides (e.g. $SO_4^{2-}/ZrO_2$), mounted acids (suitable carriers like porous oxides, graphite, metal salts, treated or combined with liquid acids, for example $H_2SO_4/SiO_2$), cation exchange resins (e.g. Amberlyst® 15), perfluorinated polymeric sulphuric acid (e.g. Nafion™), and/or heteropolyacids (e.g. 12-tungstophosphoric acid, $H_3[PW_{12}O_{40}]$).

Schemes 3 and 4 below illustrate how lactic acid may be used to produce ACN, according to some embodiments of the present disclosure. In Scheme 3, lactic acid is first dehydrated to form the resultant C3 carboxylic acid with a vinyl group, which may then be subsequently esterified to produce an unsaturated ester, which may then subsequently be nitrilated to form the ACN. In Scheme 4, the lactic acid is first esterified, then dehydrated, and finally nitrilated.

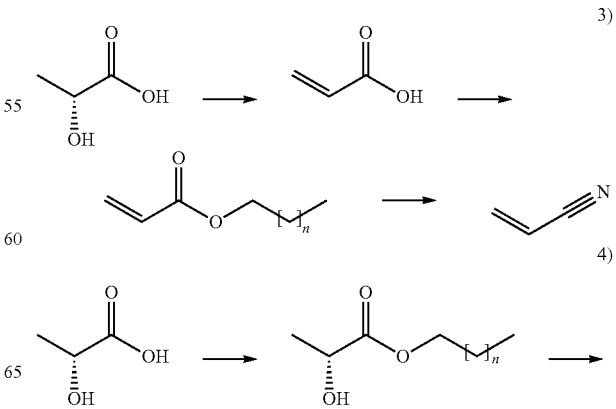

-continued

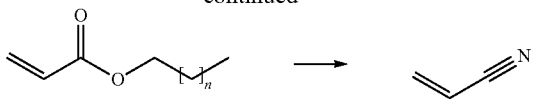

Regarding Schemes 3 and 4, the lactate ester may be processed by first passing it over a solid acid catalyst in the absence of ammonia, dehydrating the hydroxyl group at the C2 position of the lactate ester to produce the acrylate ester and water. Typical contact times may be between 0.1 sec and 10 sec. WHSVs between 1 sec and 10 sec, GHSVs between 1000 and 10,000, at reactor temperatures between 250° C. and 400° C. The produced acrylate ester and water vapors may then be mixed with ammonia in a $NH_3$:ester molar ratio between 1:1 and 10:1 and passed over a second sequential solid acid catalyst bed in the same fashion as described above to produce ACN, ethanol, and water. Alternatively, the reaction may be processed in a single catalytic bed where the lactate ester and/or acrylate ester may be volatilized and mixed with ammonia using a 1:1 to 10:1 $NH_3$:ester molar ratio and passed over a solid acid catalyst as described above to produce ACN. While the overall reaction of Schemes 3 and 4 may proceed in a single catalytic bed, without wishing to be bound by theory, at least three reactions are believed to occur: 1) esterification of the lactic acid to form an ester, 2) dehydration of the ester to form an acrylate ester, and 3) nitrilation of the acrylate ester to produce ACN, water, and an alcohol.

Figure 4:
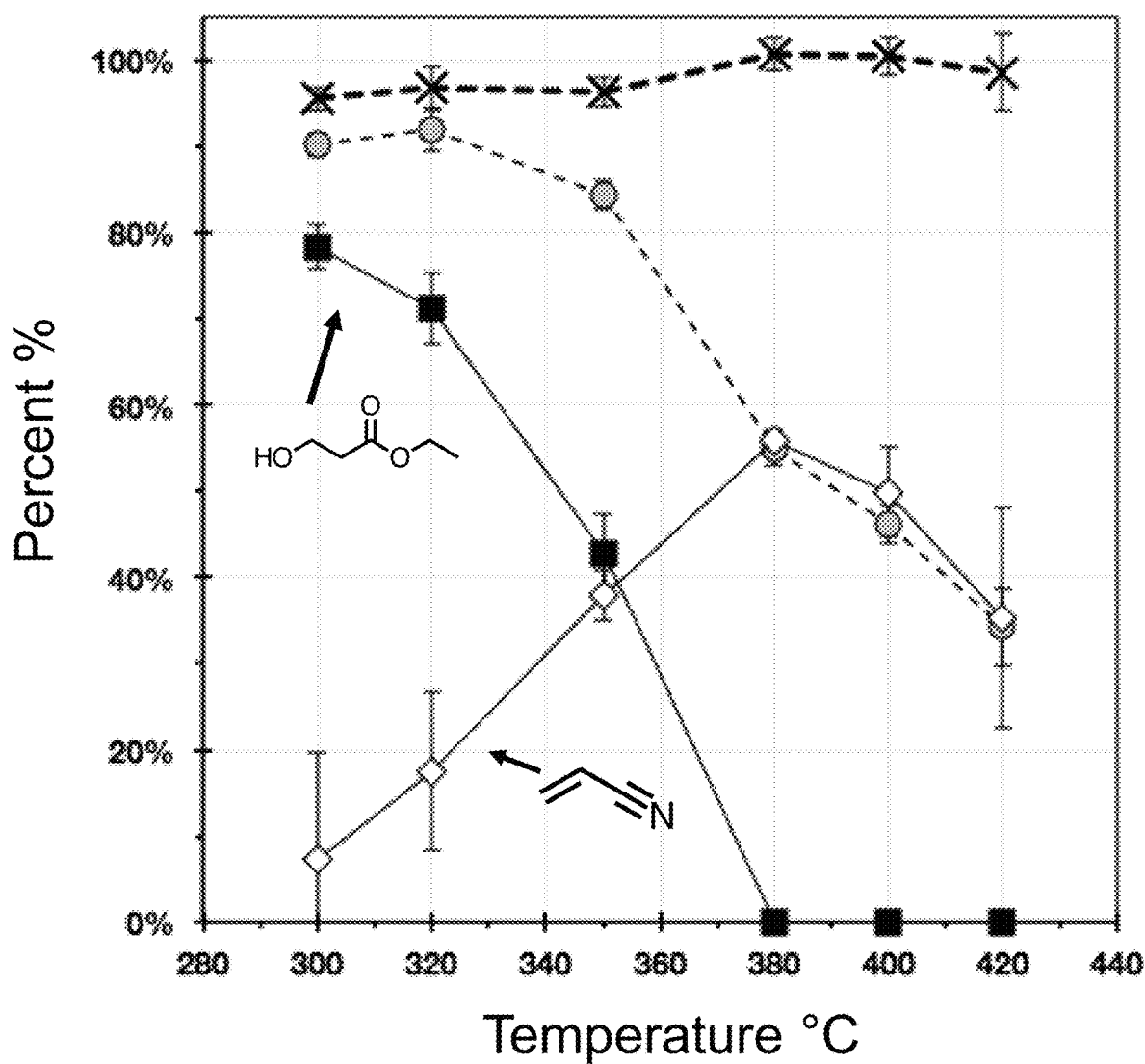
FIG. 4 illustrates experimental results obtained reacting ethyl 3-HP with ammonia at a reaction temperature of about 280° C. to approximately 450° C. over a solid zirconium oxide catalyst to produce ACN, according to some embodiments of the present disclosure.

FIG. 4 illustrates experimental results obtained reacting ethyl 3-HP with ammonia at a reaction temperatures ranging between about 280° C. to approximately 450° C., over a solid zirconium oxide catalyst ($ZrO_2$), according to the general reaction scheme shown in FIG. 3. (The data set having the x markers corresponds to conversion and the data set having circle markers corresponds to the carbon balance.) Ethyl 3-HP (>98%) was injected neat into flowing $N_2$ (400-2000 sccm) at 150° C. to produce vapors of ethyl 3-HP in $N_2$ carrier gas. The vapors were then mixed with ammonia gas with molar ratios between 1:1 and 10:1 of ammonia to ester and passed over a packed bed of 20.6 g (~17 mL) of $ZrO_2$ (particle size 35-60 mesh) at contact times between 0.1 and 1.5 sec to produce the data in FIG. 4. The exhausted products were quantified using a MKS multigas FTIR system (model 2030). Passing a range of concentrations of the vapors of each compound in nitrogen carrier gas through the FTIR system produced calibration curves for ACN, ethanol, water, ethyl 3-hydroxypropanoate ester, and ethyl acrylate.

Figure 5A:
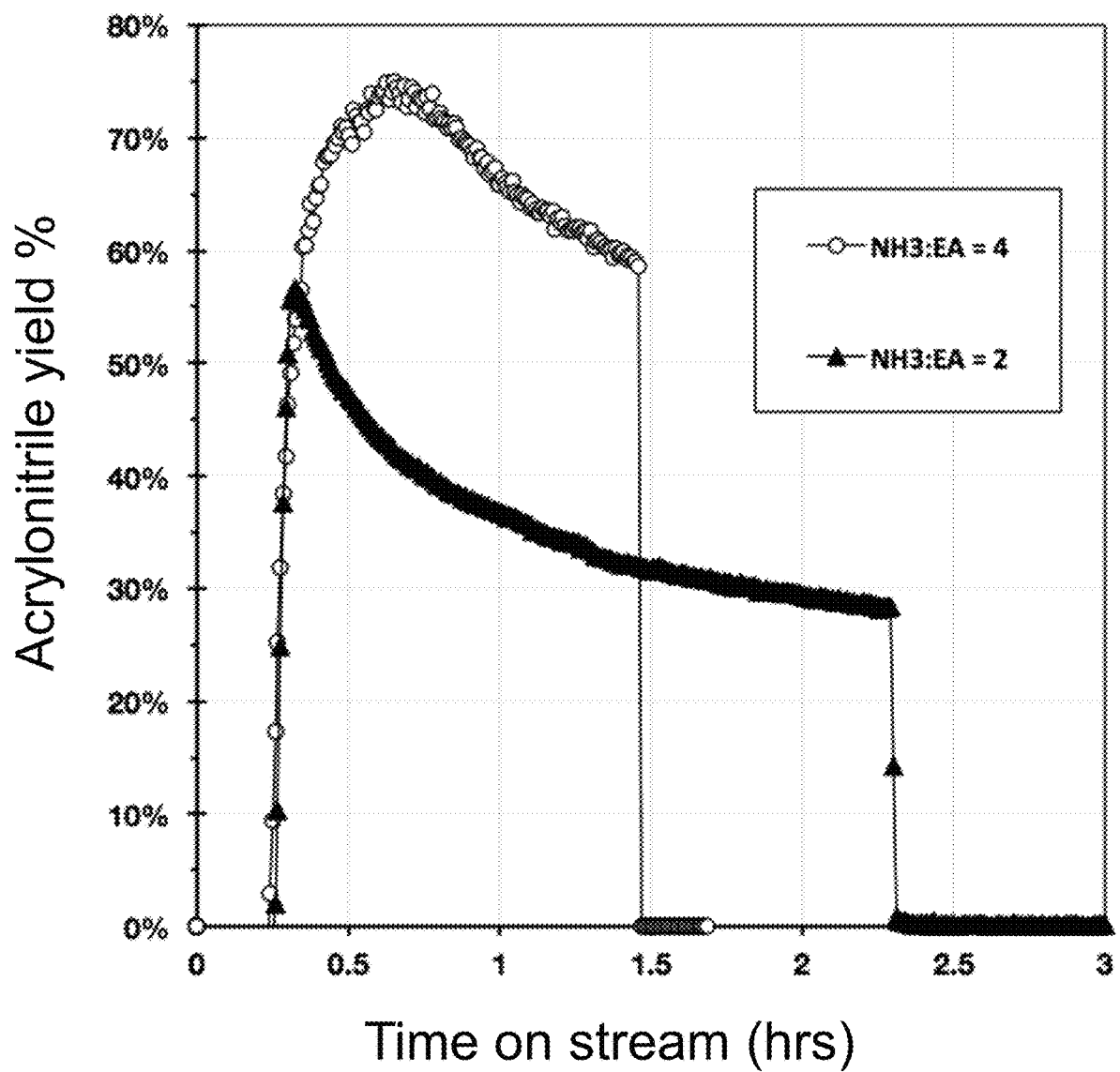
FIGS. 5A and 5B illustrate experimental results obtained reacting ethyl 3-HP with ammonia at 350° C. in contact with 13 g of $ZrO_2$ to produce ACN, according to some embodiments of the present disclosure.
Figure 5B:
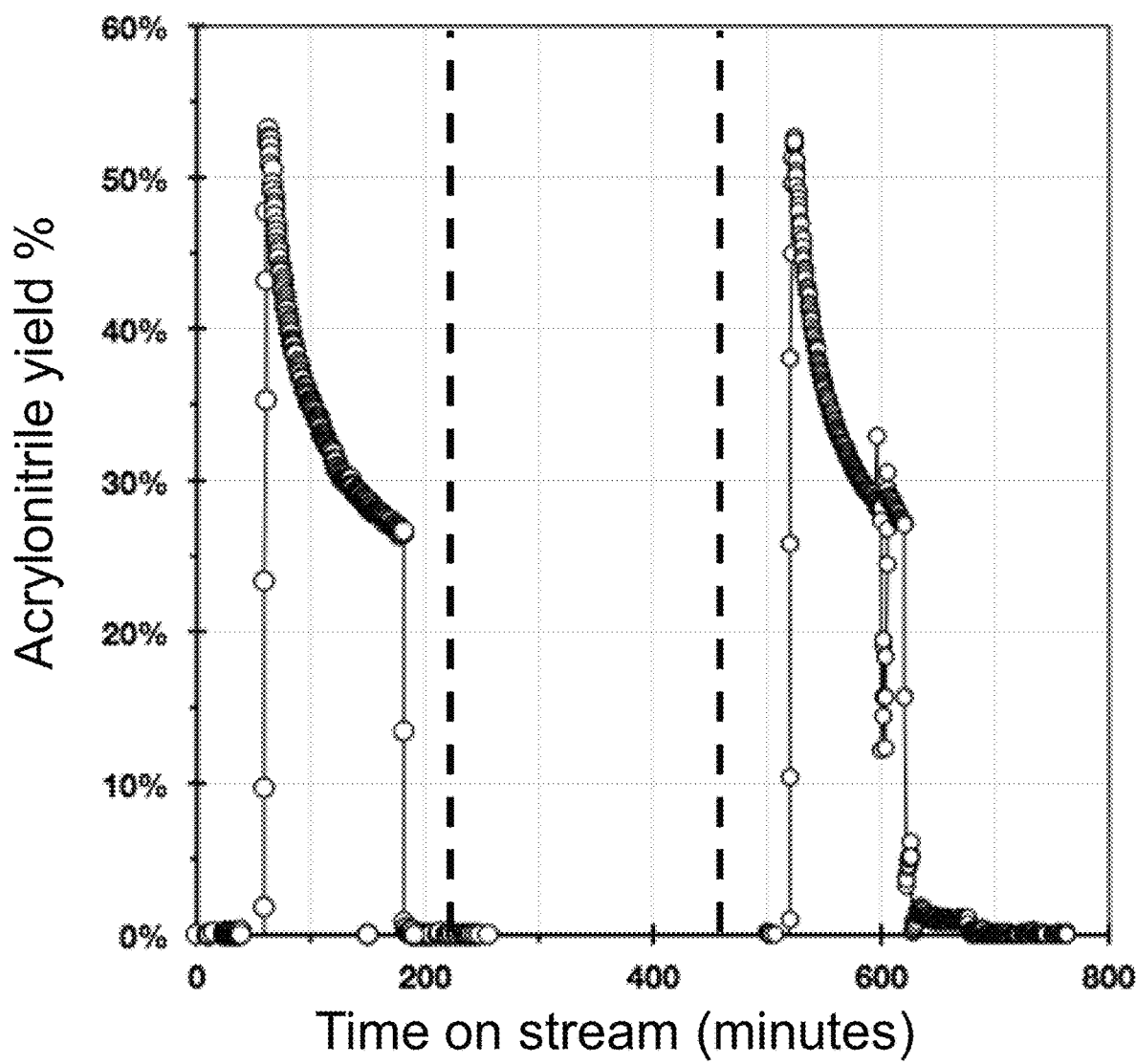

FIGS. 5A and 5B illustrate experimental results obtained reacting ethyl 3-HP with ammonia at 350° C. over 13 g of $ZrO_2$ catalyst (GHSV 6304 $hr^{-1}$). In FIG. 5A the effect of increasing the molar ratio ammonia to ester from 2:1 to 4:1 is displayed at a reactor temperature of 350° C. Here the increase in the molar ratio of ammonia to ester has a beneficial effect on the yield of ACN obtained, increasing the maximum yield from 55% to 75%. Thus, optimal reaction conditions are between 1:1 to 10:1 molar ratio of ammonia to ester. FIG. 5B illustrates successful regeneration of the catalyst, with a regeneration cycle framed between the two vertical dashed lines. On the first pass, the yield of ACN decays over time plateauing at ~25% yield of ACN. After about 1 hour of catalyst regeneration, by treatment of the $ZrO_2$ catalyst with 20 vol % oxygen in nitrogen ($N_2$), the second pass catalyst activity was recovered to a level equal to that of the first pass.

Figure 6:
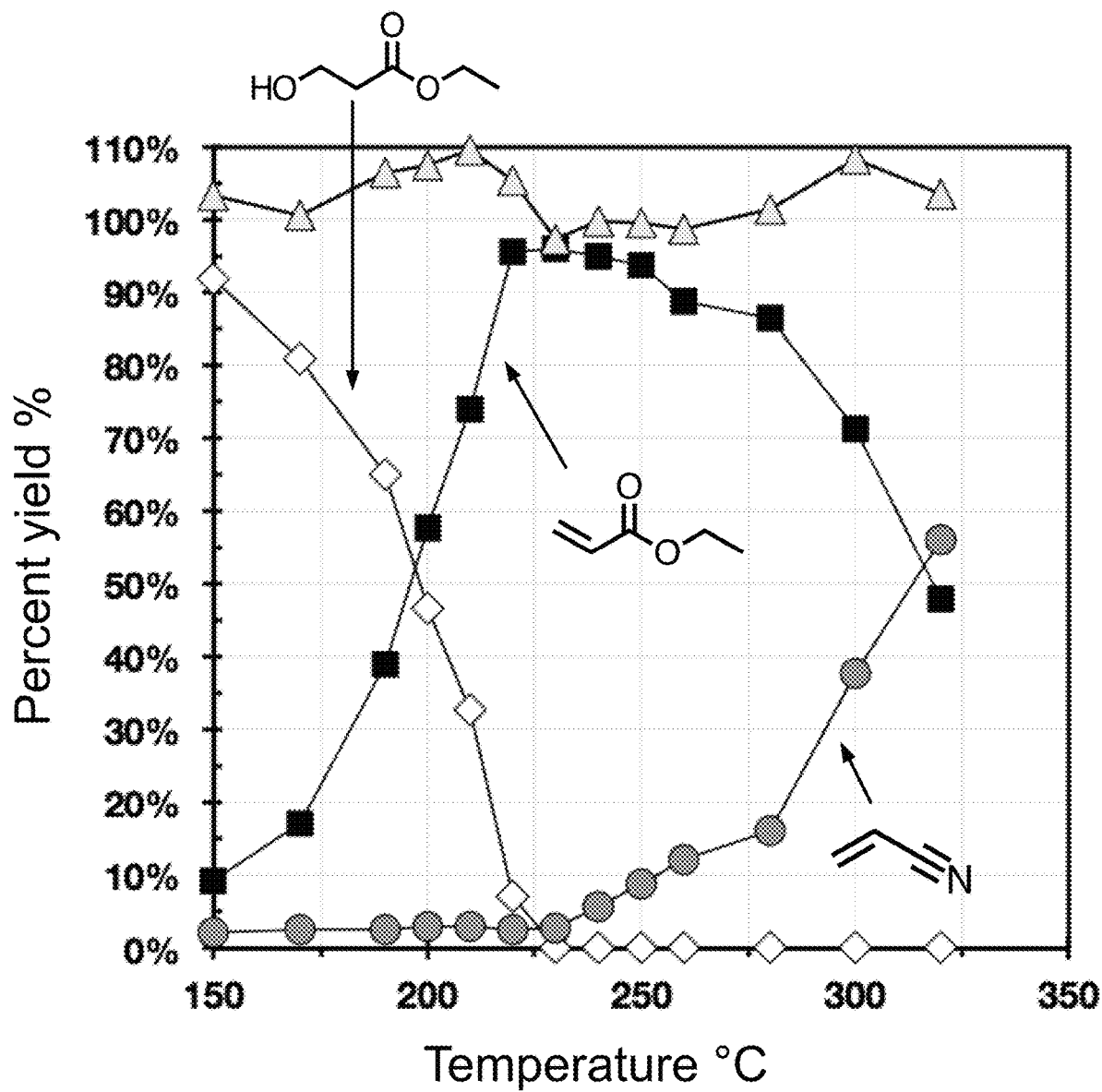
FIG. 6 illustrates steady state reaction products produced when passing ethyl 3-HP over $TiO_2$ in the presence of ammonia to produce ACN as a function of reactor bed temperature, according to some embodiments of the present disclosure.
Figure 7A:
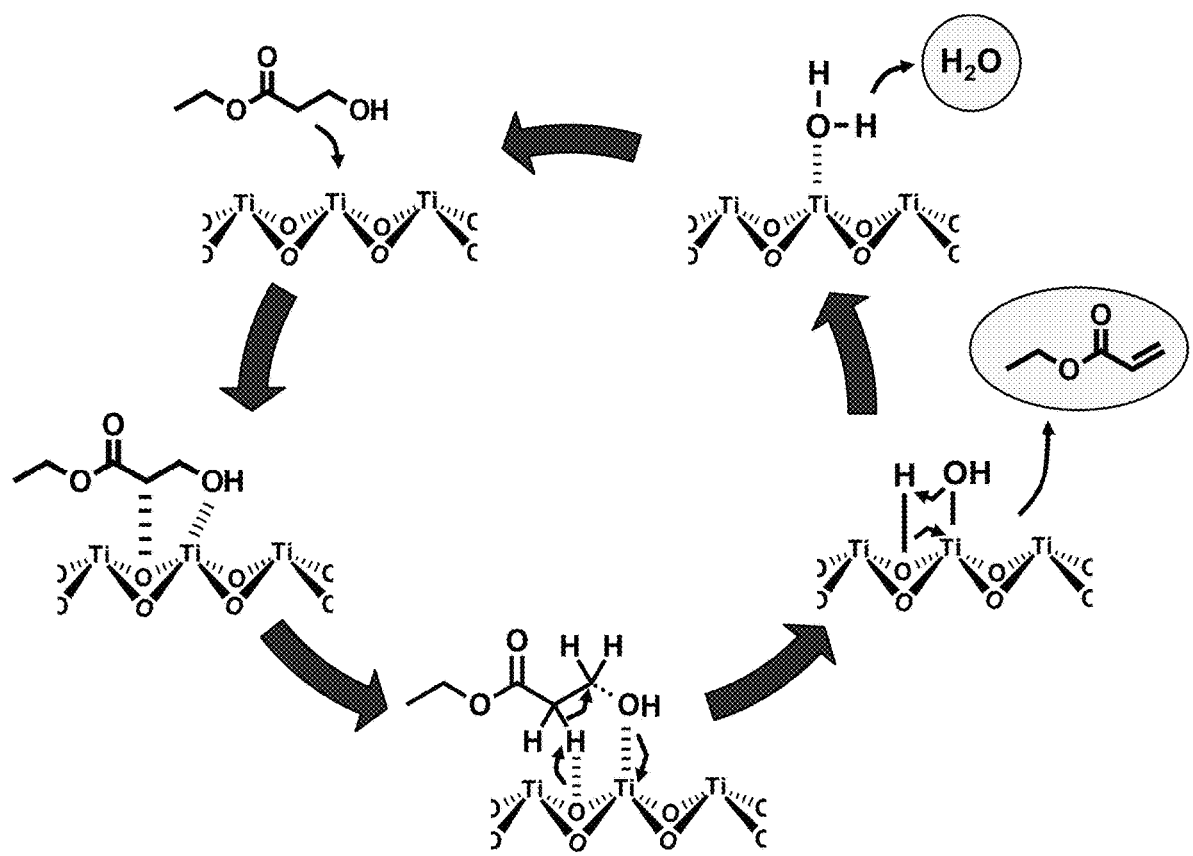
FIG. 7A illustrates a mechanism for the dehydration of ethyl 3-HP to form ethyl acrylate, according to some embodiments of the present disclosure.
Figure 7B:
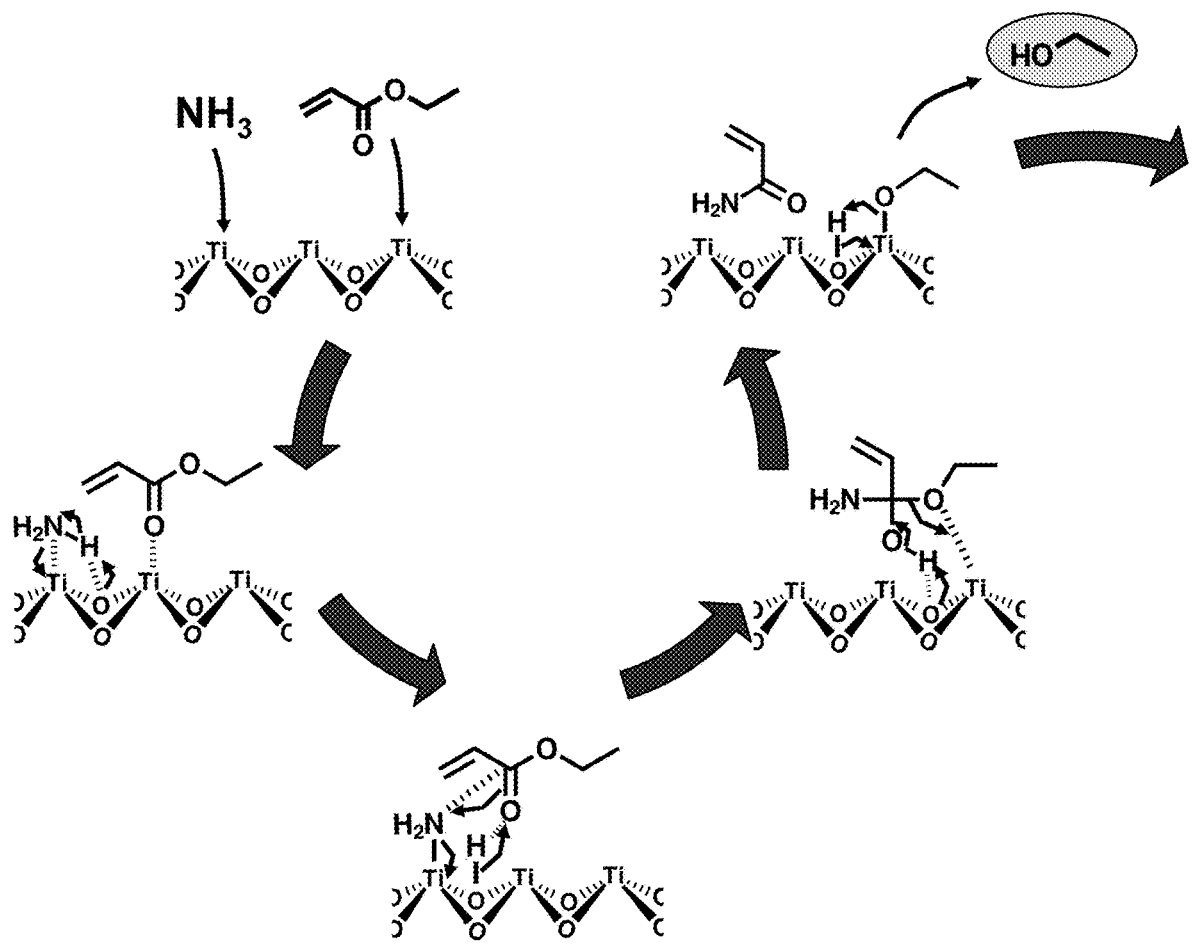
FIG. 7B illustrates a mechanism for the aminolysis of ethyl acrylate to form adsorbed acrylamide and gaseous ethanol, according to some embodiments of the present disclosure.
Figure 7C:
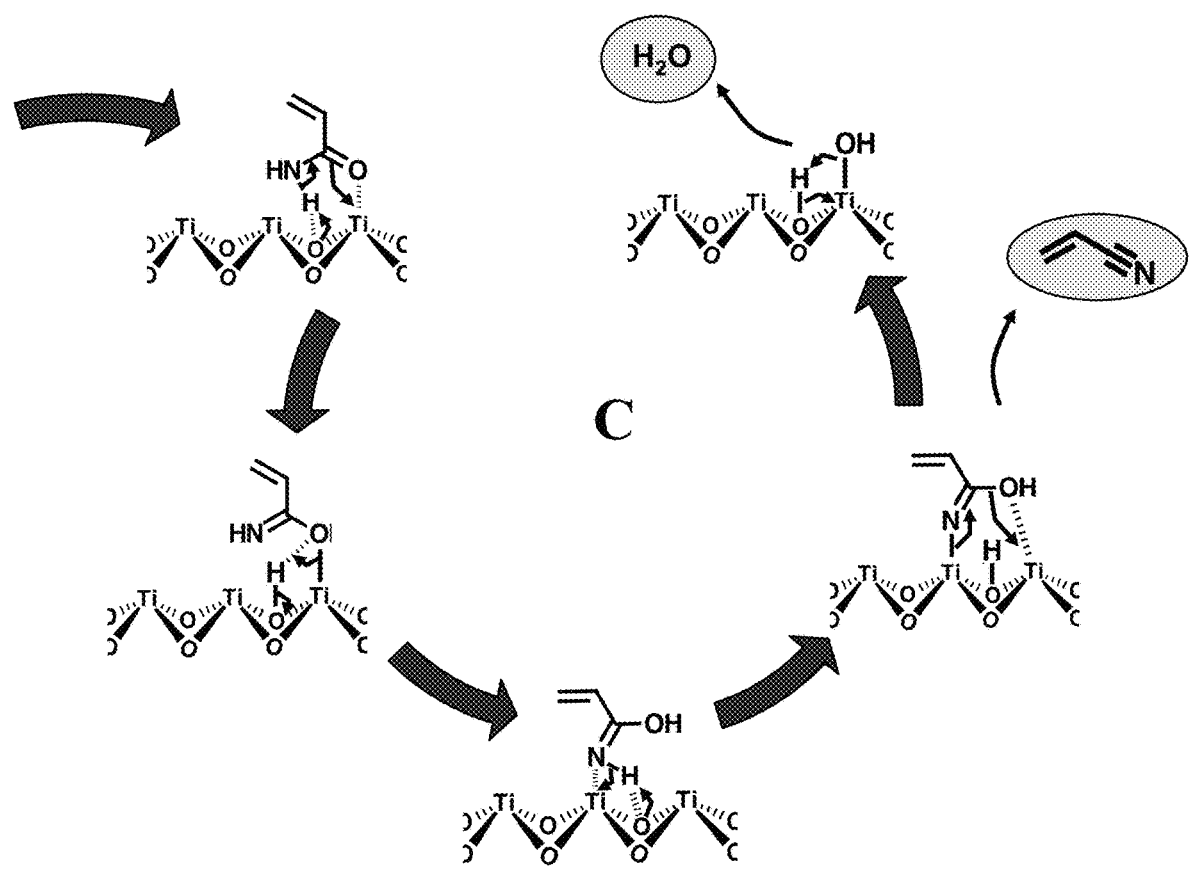
FIG. 7C illustrates a mechanism for the dehydration of adsorbed acrylamide to form gaseous ACN, according to some embodiments of the present disclosure.

FIG. 6 shows reaction products at steady state conditions for increasing reactor temperatures for ethyl 3-HP passed over a $TiO_2$ catalyst with excess ammonia (data set with triangular markers corresponds to carbon balance). The ethyl 3-HP substrate (diamond data set) was consumed in conjunction with the appearance of ethyl acrylate (solid square data set) as the reactor temperature was increased from 150° C. to 230° C. Increasing the reactor temperature further from 230° C. to 320° C. produced ACN at the expense of ethyl acrylate. Without wishing to be bound by theory, the results of FIG. 6 support the three sequential reactions summarized in FIG. 3 that lead to ACN formation, starting with ethyl 3-HP. First, the hydroxyl group on the ester undergoes dehydration to form ethyl acrylate and water, then ethyl acrylate undergoes aminolysis to form adsorbed acrylamide and ethanol, and finally adsorbed acrylamide undergoes dehydration to produce gaseous ACN and water. Referring again to FIG. 3, the primary alcohol group on ethyl 3-HP of reaction 1) (the ester derivative of 3-HPA) may readily dehydrate to form an acrylate. The —OH group dehydration likely occurs similarly to alcohol dehydration reactions through the mechanism shown in FIG. 7A. The second proposed reaction is the aminolysis of the acrylate ester to produce adsorbed acrylamide and ethanol. A mechanism for reaction 2) of FIG. 3 is shown in FIG. 7B. Given that acrylamide was not observed in the product vapors, this suggests that acrylamide remains adsorbed to the surface and rapidly dehydrates over the solid acid to yield ACN via reaction 3) of FIG. 3 through the mechanism shown in FIG. 7C.

Figure 8:
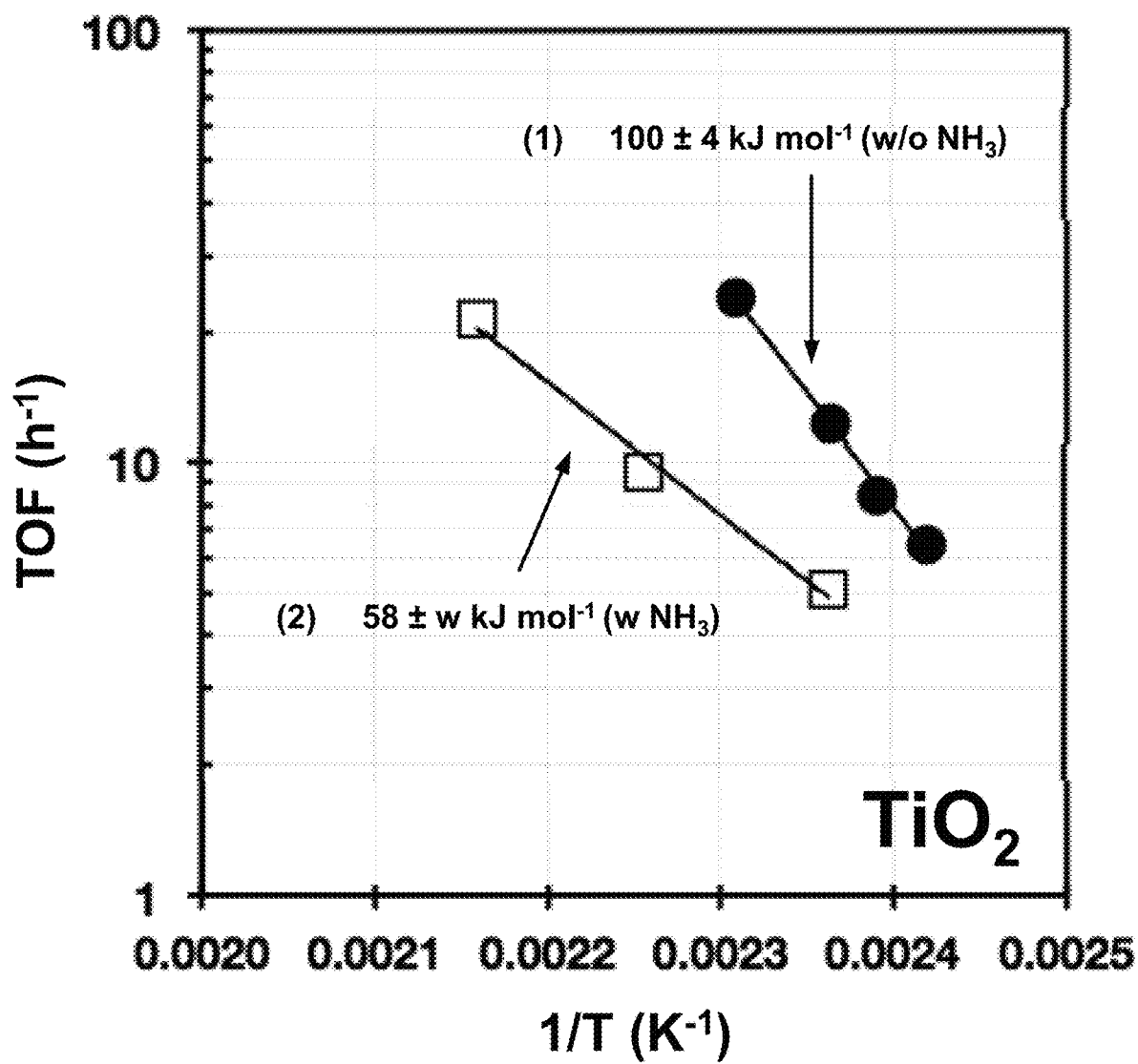
FIG. 8 illustrates an Arrhenius plot for the dehydration of the 3 position —OH group of ethyl 3-HP to form ethyl acrylate and water (reaction 1) of FIG. 3), in the presence of ammonia in the feed (empty squares, 58±2 kJ/mol), and in the absence ammonia in the feed (solid circles, 100±4 kJ/mol), according to some embodiments of the present disclosure.
Figure 9:
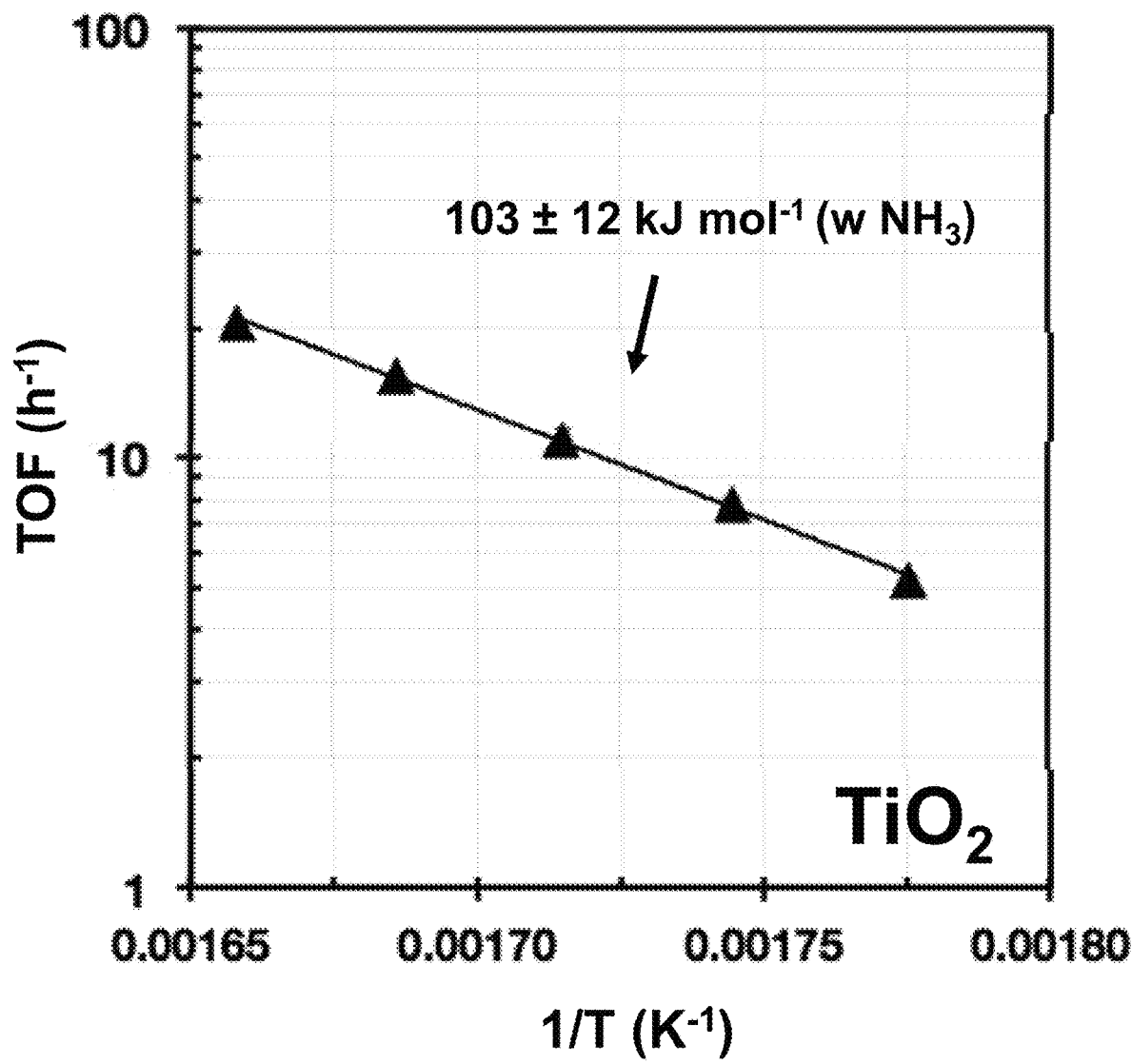
FIG. 9 illustrates an Arrhenius plot for the nitrilation of ethyl acrylate to form ethanol, water and ACN (see reactions 2) and 3) of FIG. 3), according to some embodiments of the present disclosure. This analysis yields an apparent activation energy for the reductive nitrilation of ethyl acrylate of 103±12 kJ/mol.
Figure 10:
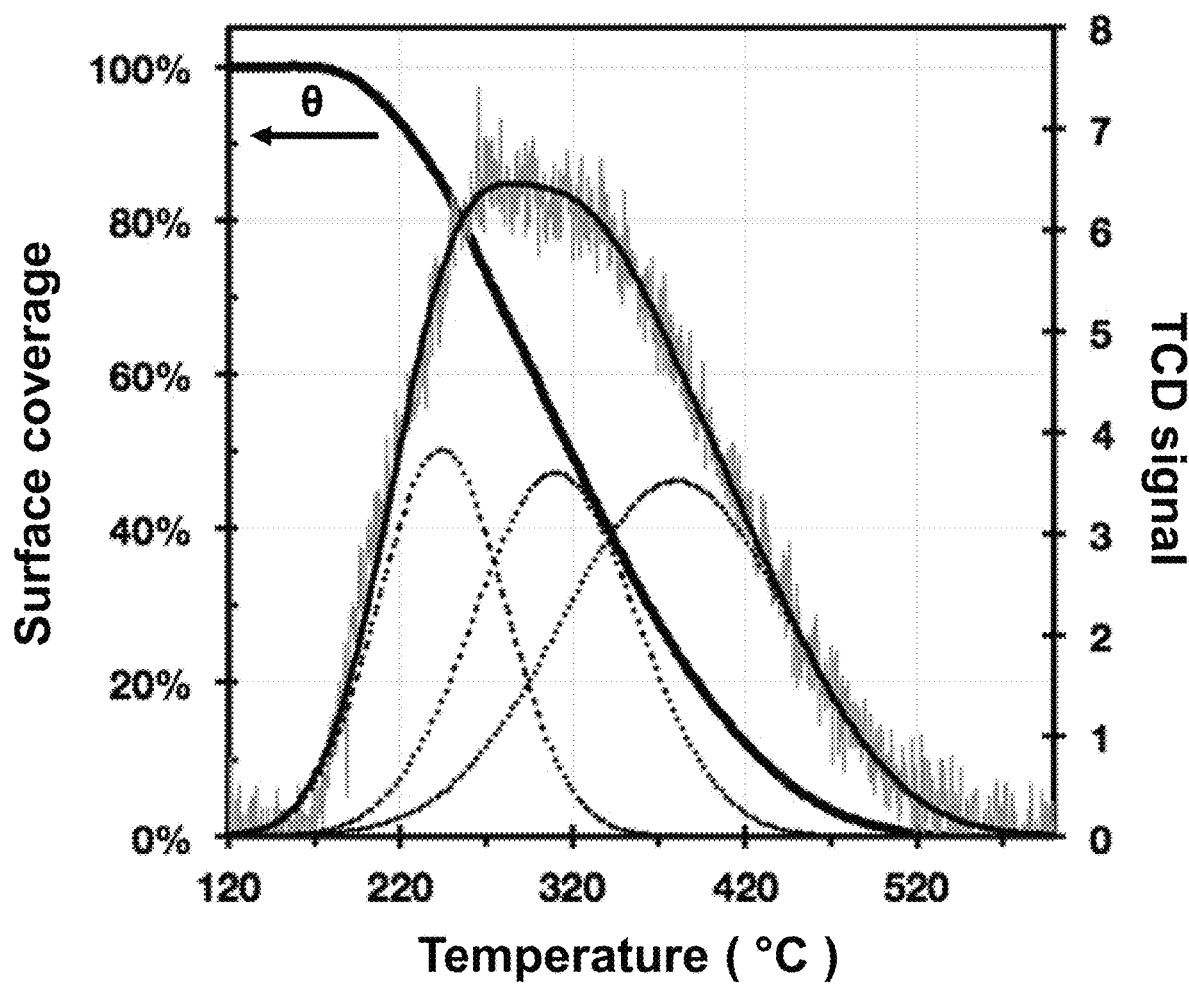
FIG. 10 illustrates ammonia temperature programmed desorption results for the desorption of ammonia from a $TiO_2$ catalyst, according to some embodiments of the present disclosure. Here three Gaussian curves were used to model the TCD trace finding a desorption energy of 95±8 kJ/mol using a first order redhead analysis.

Kinetic measurements at low conversions were performed, which demonstrated an apparent activation energy for reaction 1) of FIG. 3 of 58±2 kJ/mol in the presence of ammonia and an apparent activation energy of 100±4 kJ/mol in the absence of ammonia (see FIG. 8). Referring to FIG. 9, the activation energy of 103±12 kJ/mol found for the sum of reactions 2) and 3) of FIG. 3 is nearly identical to the activation energy of ammonia desorption from $TiO_2$, 95±8 kJ/mol, determined through a Redhead analysis of ammonia temperature programmed desorption (see FIG. 10). Without wishing to be bound by theory, the similarity in apparent activation energy of reactions 2) and 3) of FIG. 3 with the ammonia desorption energy on the $TiO_2$ catalyst suggests that the rate limiting step in the overall reaction may be site competition with ammonia for acid sites on the $TiO_2$ surface. Presumably, the "true" activation energy of reactions 2) and 3) of FIG. 3 could be measured by performing low conversion measurements at higher temperatures where site competition with ammonia is no longer limiting. However, the catalyst coked at temperatures above 330° C., precluding this measurement.

Figure 11:
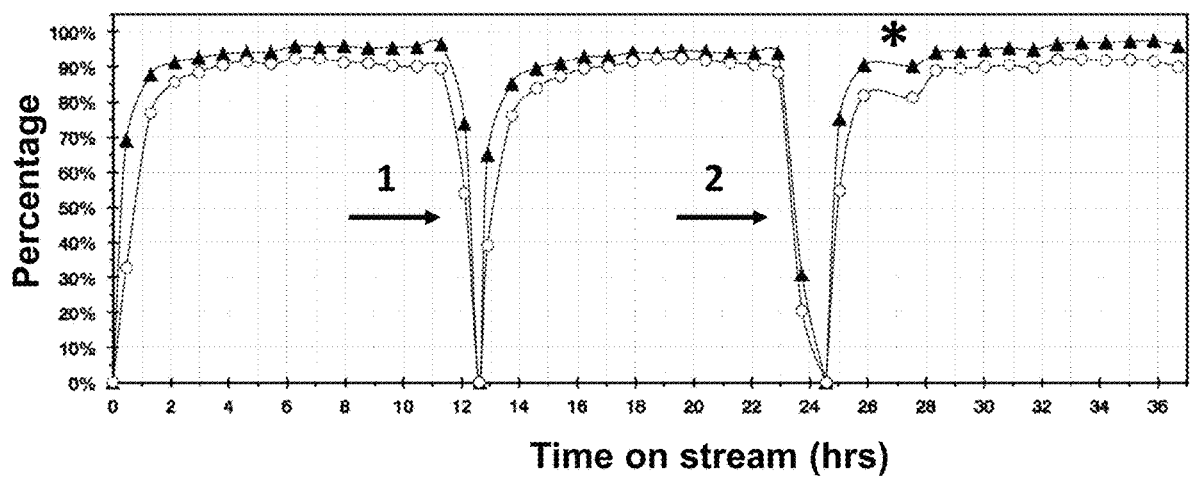
FIG. 11 illustrates catalytic conversion of ethyl 3-HP to ACN be reaction in a two-reactor (tandem) system, for both purchased and bio-derived ethyl 3-HP, according to some embodiments of the present disclosure.
Figure 12:
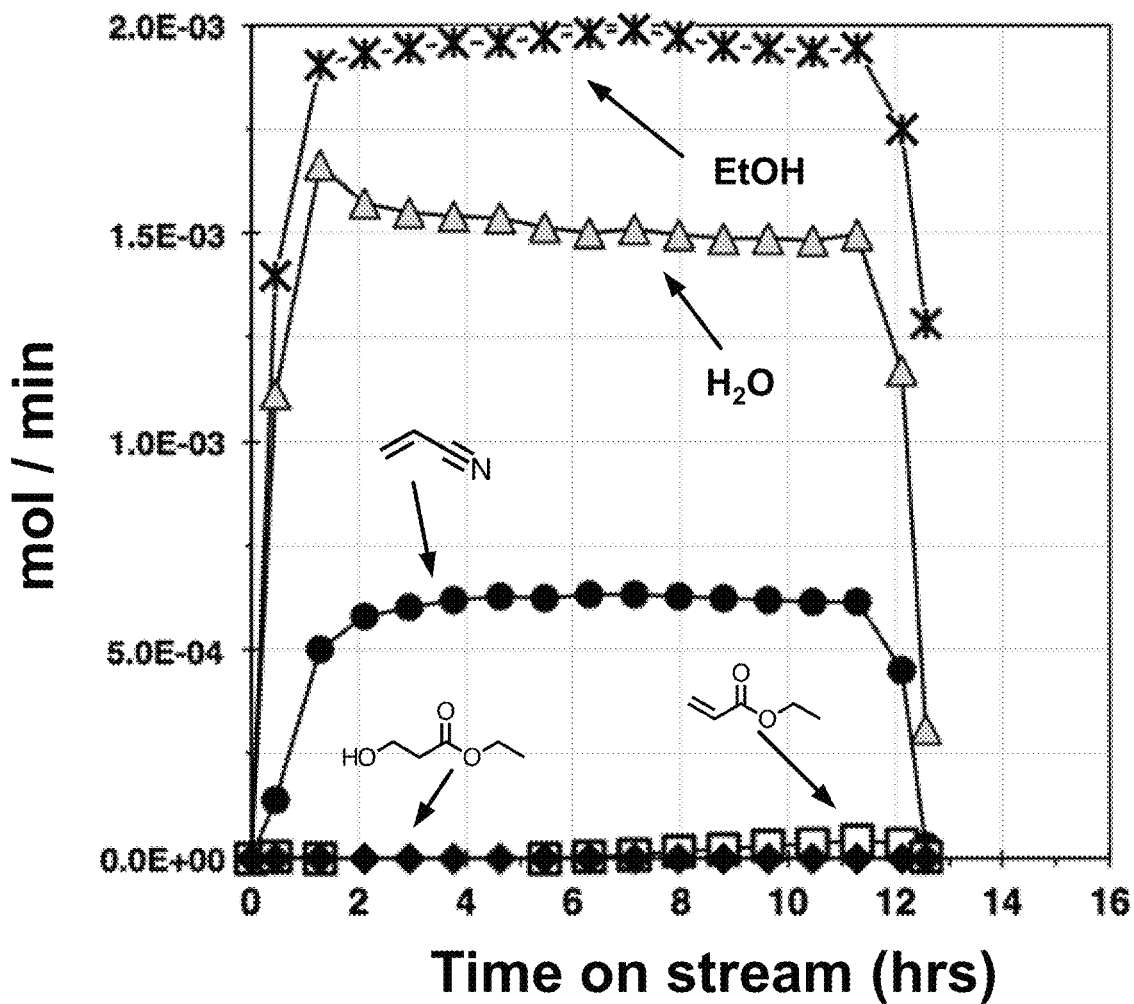
FIG. 12 illustrates a complete data set and conditions used for the first run results, before the regeneration shown in FIG. 11, according to some embodiments of the present disclosure
Figure 13:
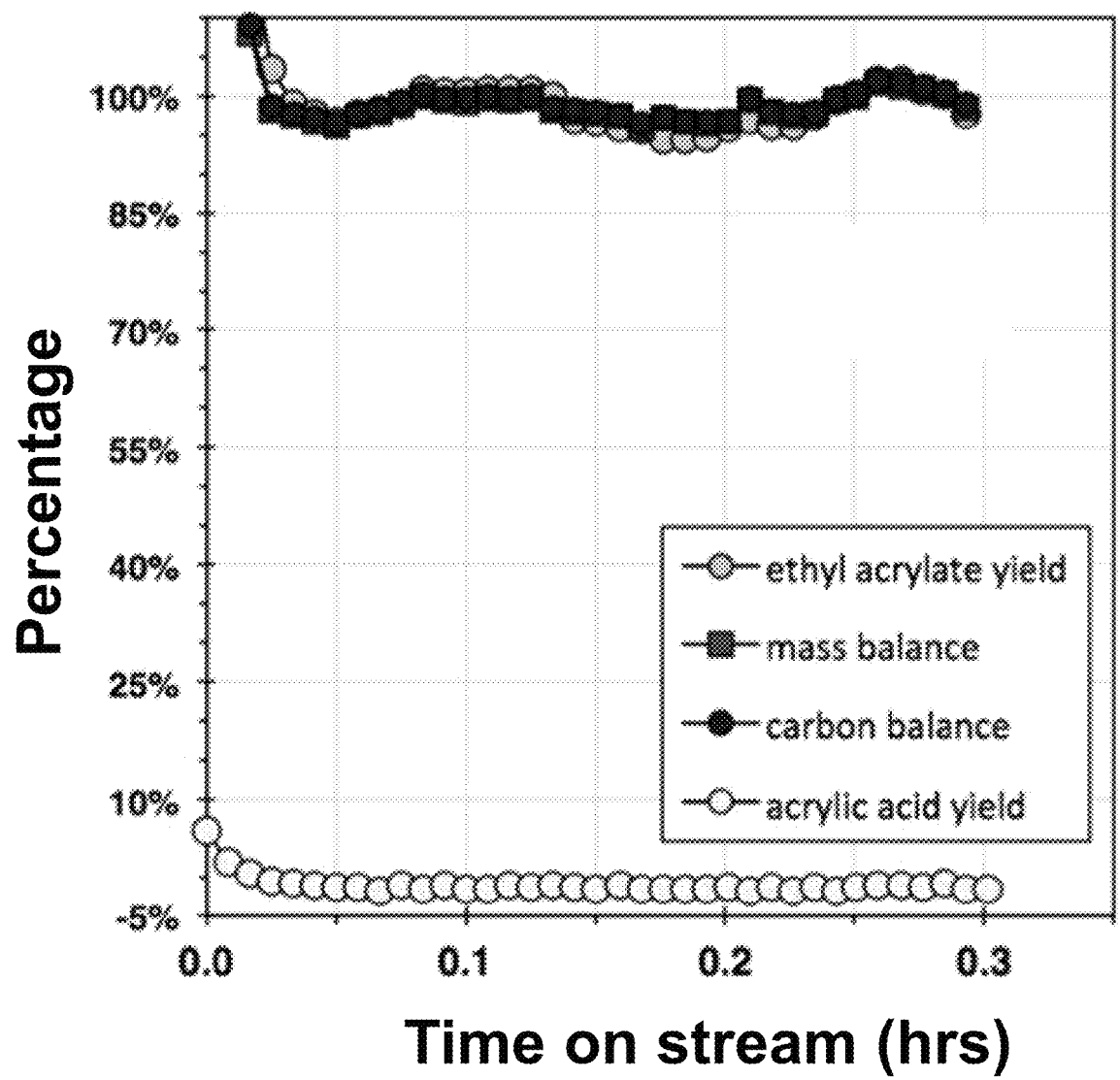
FIG. 13 illustrates results from total conversion experiments performed to maximize the yield of ethyl acrylate formed when dehydrating the 3-position —OH group on ethyl 3-HP, according to some embodiments of the present disclosure. Here ethyl 3-HP was passed over the $TiO_2$ catalyst at 250° C. with a 2:1 molar excess of ethanol. The excess ethanol was needed to suppress the equilibrium formation of acrylic acid. 100% yield of ethyl acrylate was obtained with 100% mass balance using the parameters listed in the grey box.
Figure 14:
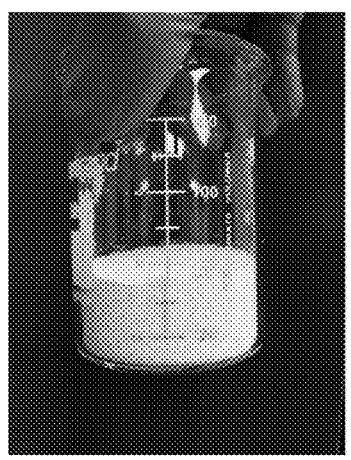
FIG. 14 illustrates fresh, spent and regenerated $TiO_2$ catalyst used for the experiments shown in FIGS. 11-13 according to some embodiments of the present disclosure.
Figure 14:
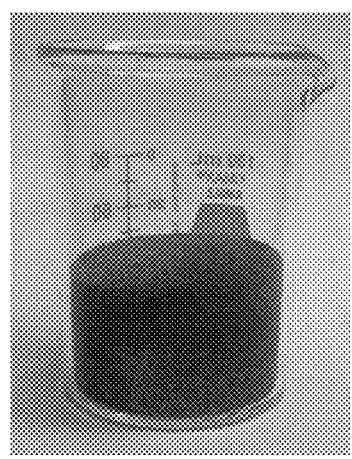
Figure 14:
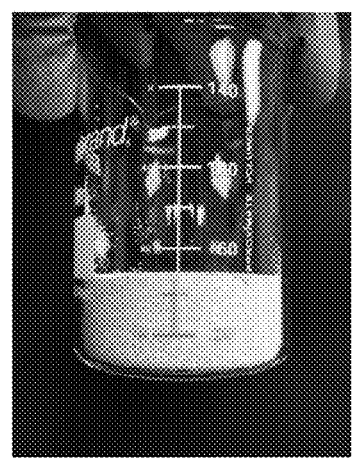
Figure 15:
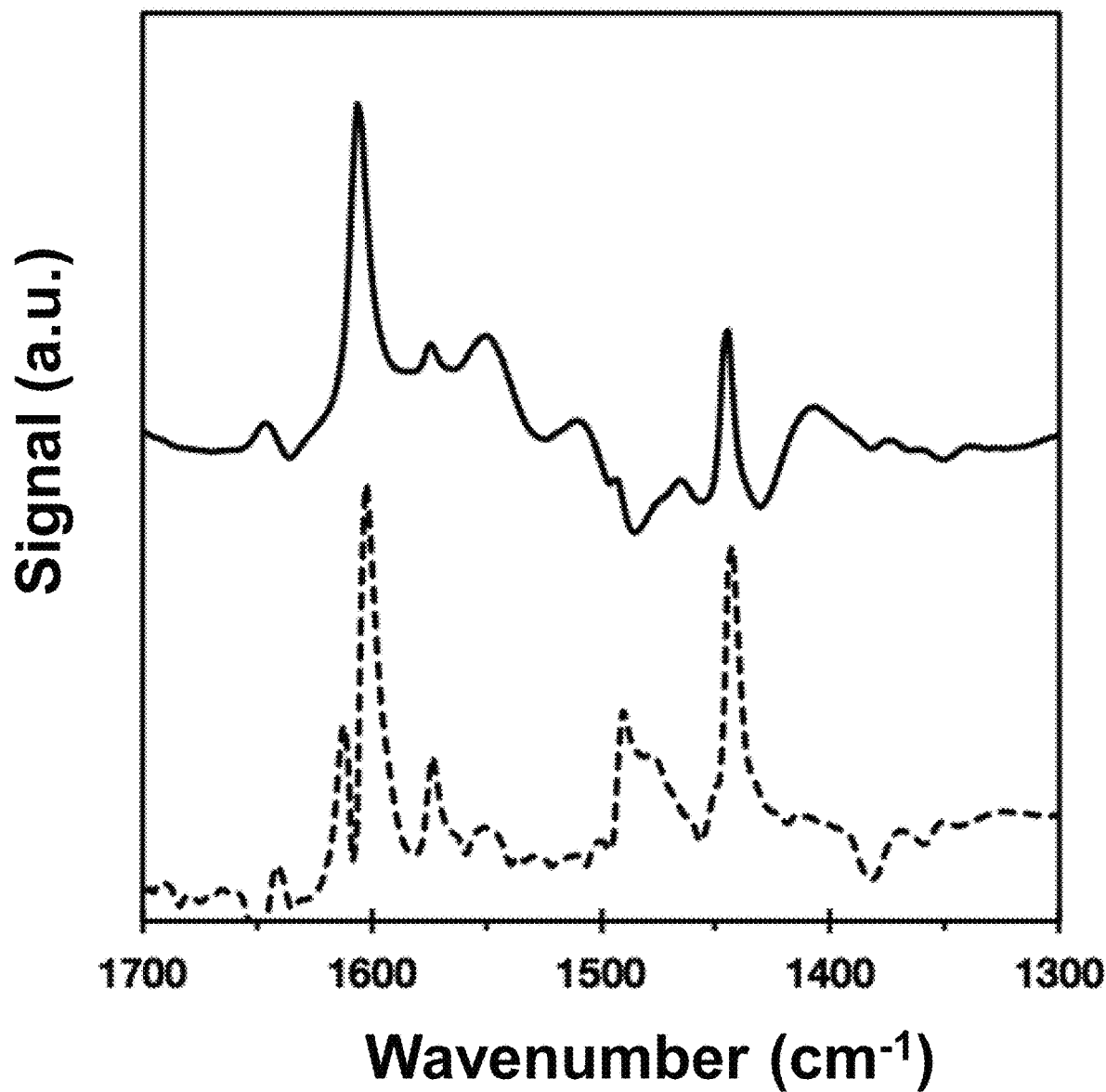
FIG. 15 illustrates diffuse reflectance infrared Fourier transform spectroscopy (DRIFTS) spectrum of pyridine on fresh (dashed) and regenerated (solid) $TiO_2$, according to some embodiments of the present disclosure.

High conversion experiments were conducted in a tandem bed reactor system where in a first reactor ethyl 3-HP was dehydrated over $TiO_2$, for example in a packed bed reactor, to form ethyl acrylate and water in quantitative yield. The product vapors from the first reactor were then mixed with ammonia and passed over a second reactor, a packed bed of $TiO_2$ at 315° C. to form ACN, ethanol, and water. The overall carbon balance and ACN yield for two runs, separated by a regeneration step as explained below, completed on this two-reactor system are summarized in FIG. 11. Note that a molar excess of 2:1 ethanol to ethyl 3-HP was used as the feed to the first reactor to suppress the equilibrium formation of acrylic acid and favor the ethyl ester product, ethyl acrylate, with the results summarized in FIG. 13. Using non-bioderived ethyl 3-HP, the reactor system operated in this fashion achieved ACN yields of 90-92% for the first ~12 hours on stream and then began to slowly deactivate but over 90% yield was still maintained at 12 hours time-on-stream. At the conclusion of the first 12 hour period, the catalyst was removed from the nitrilation reactor and regenerated by exposure to air for about an hour at 550° C. (indicated by arrow #1 in FIG. 11). This regenerated the catalyst to about the same activity so that a second run, also using non-bio-derived ethyl 3-HP, as shown in FIG. 11, also resulted in about the same carbon balance and ACN yield. Overall, each run produced approximately 25 g of ACN for a total of about 50 g for the two runs, and about 75 g when including the bio-derived starting materials. In addition, a third run to produce ACN was produced utilizing bio-derived ethyl 3-HP as described below, following a second regeneration (as indicated by arrow #2), resulting in similar high ACN yields and carbon balance as was achieved using the non-bio-derived ethyl 3-HP (as indicated by the asterisk). FIG. 12 summarizes the second reactor's species output as a function of time for the first run of the reaction summarized in FIG. 11.

FIGS. 14-17 illustrates fresh, spent, and regenerated catalyst side-by-side along with pyridine DRIFTS, BET, acid site density measurements (see Table 1) and XRD measurements, respectively, showing that the regeneration cycle restores these characteristics to that of the fresh sample. Additionally, TGA-FTIR measurements of the gas released during catalyst regeneration show $NO_x$ was not produced (see FIG. 18) abating the need for expensive exhaust cleanup during regeneration cycles.

|  | Fresh $TiO_2$ | Spent $TiO_2$ | Regenerated $TiO_2$ |
|---|---|---|---|
| Acid sites ($\mu mol\ g^{-1}$) | 160 | — | 200 |
| BET ($m^2\ g^{-1}$) | 49 | 27 | 50 |

Figure 19:
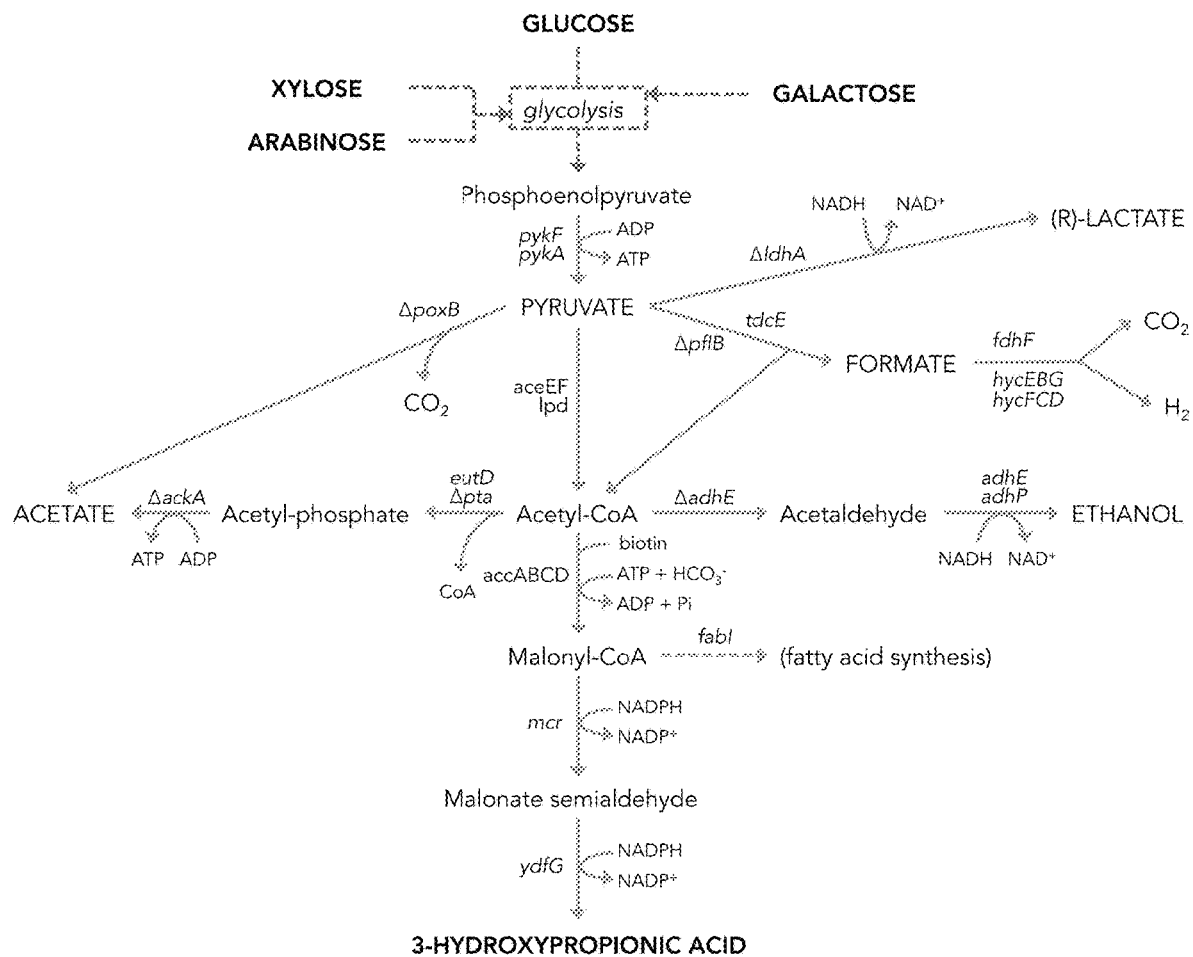
FIG. 19 illustrates the metabolic pathway for 3-HP production in recombinant *Escherichi Coli* (*E. coli*) BGHP strain.
Figure 20:
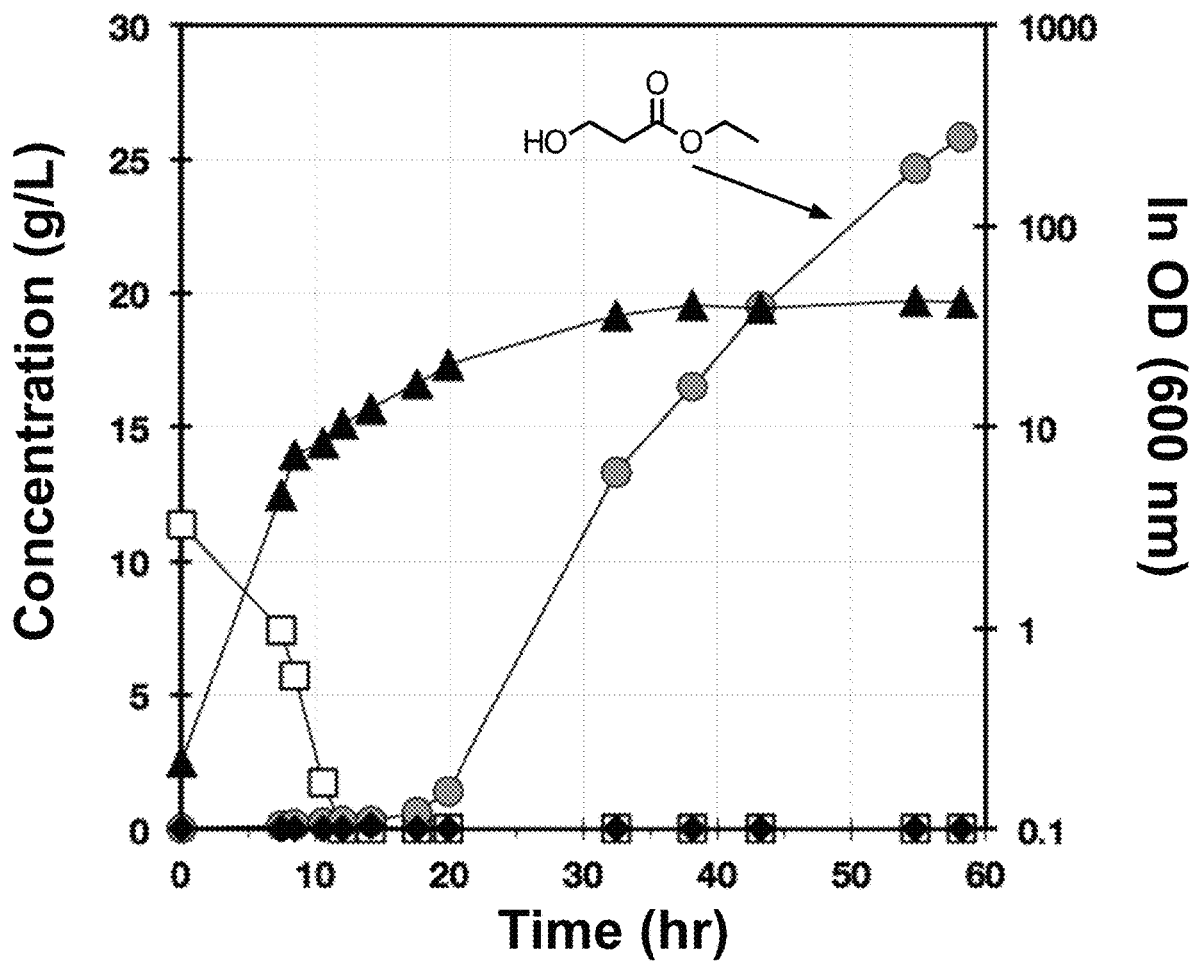
FIG. 20 illustrates fed-batch DO-stat (immediate dissolved oxygen) cultivation of a strain of *E. coli* using glucose as a carbon source, according to some embodiments of the present disclosure.
Figure 21:
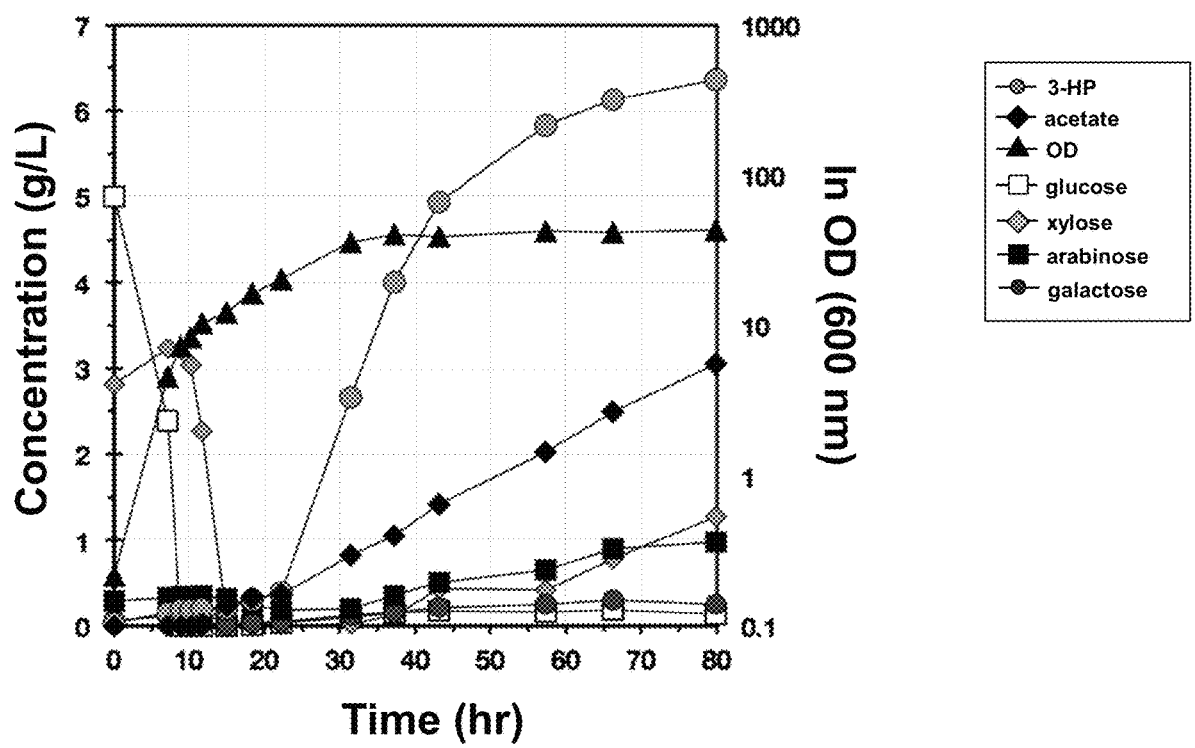
FIG. 21 illustrates fed-batch DO-stat cultivation of *E. coli* using de-acetylated, dilute-acid pretreated, enzymatically hydrolyzed (DDAP-EH) corn stover hydrolysate, according to some embodiments of the present disclosure.
Figure 22:
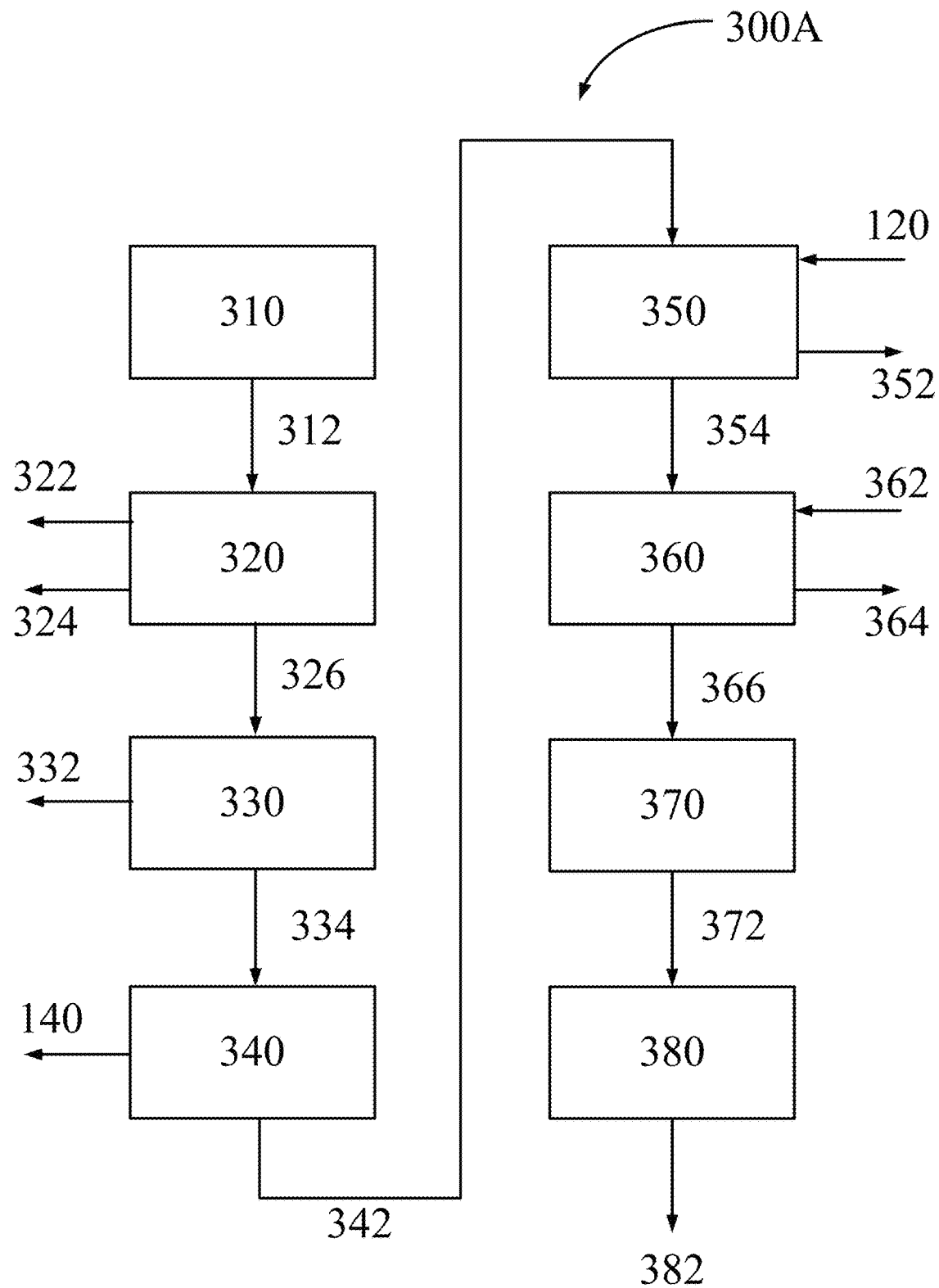
FIG. 22 illustrates a system for separating ethyl 3-HP from fermentation broth, according to some embodiments of the present disclosure. The recovered ethyl-3HP was converted to ACN as described herein.

As a demonstration of this chemistry, bio-derived 3-HPA was produced via glucose cultivation using an engineered *E. coli* strain with the malonyl-CoA pathway (see FIG. 19). The cultivation strategy employed fed-batch DO-stat control to feed glucose to the bioreactor, and resulted in a titer of 25.8 g/L (see FIG. 20 where triangles refer to the optical density, squares to glucose in g/L, and diamond/squares to acetate in g/L). In addition, production of 3-HPA from lignocellulosic hydrolysate is shown in FIG. 21. At the end of the glucose cultivation, ethyl 3-HP was separated and recovered from the broth. Briefly, the broth was first centrifuged and filtered to remove cells, debris, and protein. The broth was then treated with activated carbon and was dewatered through roto-evaporation to leave a resin of ammonium 3-hydroxy propionate salts. The salts were esterified in an ethanol solution under reflux with the addition of $H_2SO_4$, and then vacuum distilled to recover ethyl 3-HP at a final purity of 97% determined by gas chromatography. This lab-scale system 300A for producing ethyl 3-HP from a fermentation process is summarized in FIG. 22. Although this system 300A is proposed for ethyl 3-HP, it should be understood, that a similar process may be utilized for the production of other carboxylic acid esters. Thus, fermentation to produce carboxylic acids, including 3-HPA may begin in a fermenter 310 as described above. The fermenter 310 will produce a broth 312 that includes a variety of components including microorganism materials, metabolic products, etc. Thus, the broth 312 may be directed to a filter 320 (e.g. one or more filters) for the removal of cells and debris 322 and/or proteins 324 to produce a filtered broth 326. The cells and debris 322 and/or proteins 324 may be utilized in other potential applications. The filtered broth 326 may still contain color-forming contaminants and/or other undesirable contaminants, which may be subsequently removed in an adsorption unit 330 to produce a decolored broth 334. The adsorption unit 330 may utilize any suitable adsorbent (not shown) to selectively adsorb the contaminants, with an example adsorbent being activated carbon. Thus, the adsorption unit 330 may produce a spent carbon 332 stream, for situations where the adsorbent cannot be regenerated directly in the adsorption unit 330. The decolored broth 334 may then be directed to a dewatering unit 340 for removal of water 140 to reduce, for example, the mass rates and/or volumetric rates that need to be processed in downstream units and/or to affect the equilibrium reactions. The dewatering unit results in dewatered salts 342 having essentially zero water content. The dewatered salts 342 may then be directed to a salt-dissolving unit 350, which dissolves the salts contained in the dewatered salts 342 using alcohol 120, which is fed to the salt-dissolving unit 350. Any sugars contained entering the salt-dissolving unit 350 will be essentially in soluble in the alcohol 120 and will precipitate and removed as indicated by the sugars 352 stream, resulting in the formation of an alcohol mixture 354 containing the targeted metabolic products from the fermenter 310 (e.g. carboxylic acids) and dissolved salts. The alcohol 120 used in the liquid extraction unit 350 may be the same alcohol used downstream in an esterification unit 370 for converting the 3-HPA to ethyl 3-HP. The alcohol mixture 354 may then be directed to a salt-breaking unit 360 to remove salts 364 from the alcohol mixture 354, resulting in a 3-HPA/alcohol stream 366. The salts 364 may be removed by inducing precipitation of the salts 364, for example, by the addition of an acid (e.g. a mineral acid) to the reduced-sugar broth 354 in the salt-breaking unit 360. The 3-HPA/alcohol stream 366 may then be directed to the esterification unit 370, which converts the 3-HPA/alcohol stream 366, as described above, to an ethyl 3-HP/alcohol stream 372, which may then be directed to a distillation unit 380 for separating the ethyl 3-HP from the alcohol to produce a substantially pure ethyl 3-HP stream 382 suitable for nitrilation to produce ACN (not shown). Ethyl 3-HP recovered from a fermentation broth on the lab-scale as described above and illustrated in FIG. 22, and the recovered ethyl 3-HP was subsequently successfully converted to ACN as illustrated in FIG. 11, achieving identical performance to that of the synthetic ethyl 3-HP substrate. It should be noted, that although the system 300A illustrated in FIG. 22 is describe above for a lab-scale process, it should be understood that the same and/or a similar process having at least some of the same elements and features may be suitable for larger scale processes, including full-scale manufacturing plants.

Figure 23:
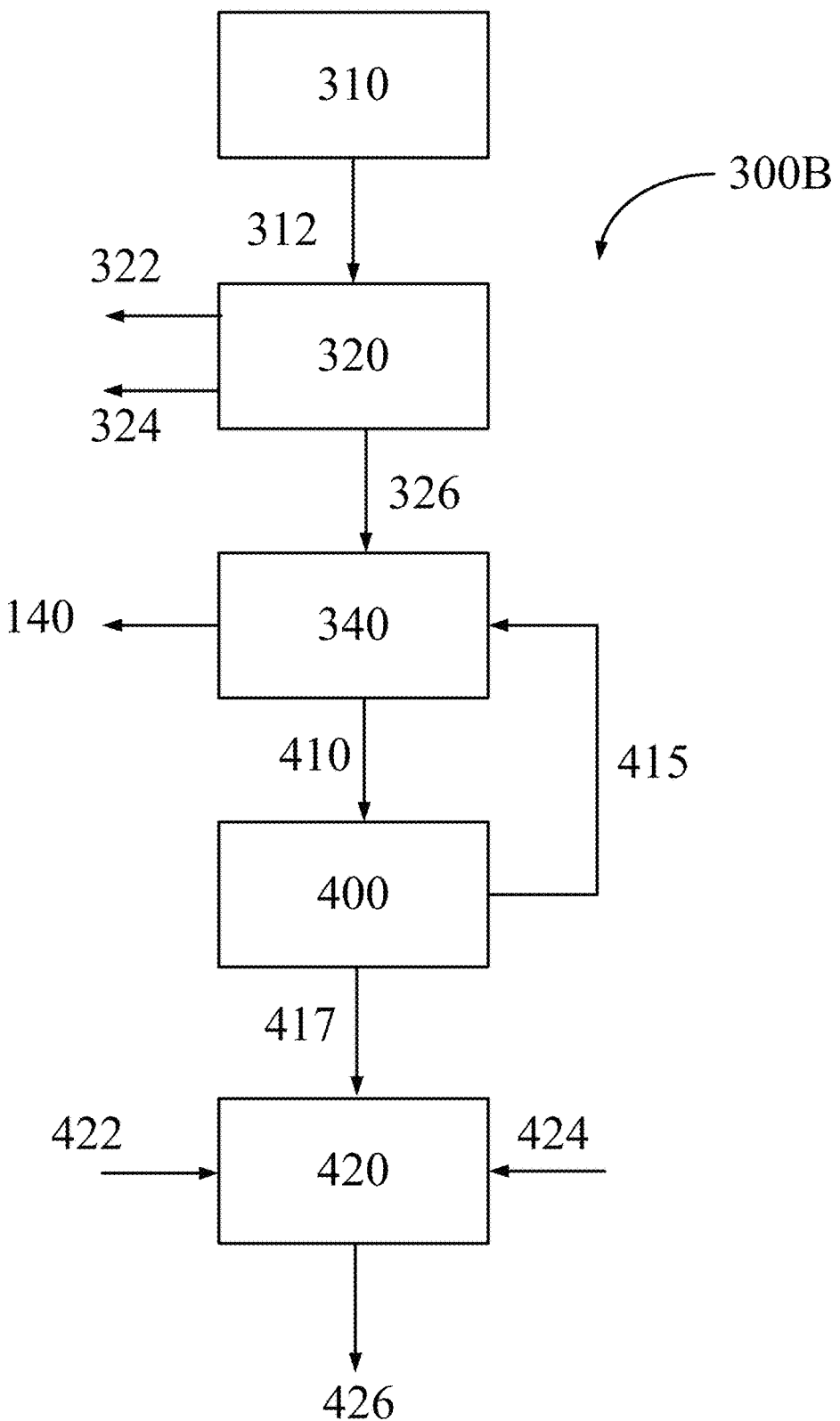
FIG. 23 illustrates a conceptual process diagram for a full-scale process/system for renewable ACN production from biomass sugars concluding with the nitrilation of ethyl acrylate, according to some embodiments of the present disclosure.
Figure 24:
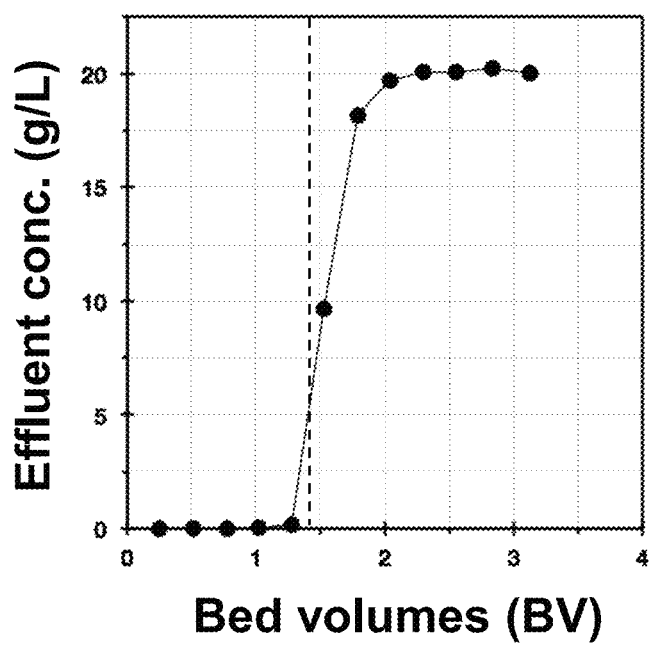
FIG. 24 illustrates (top) loading curve for acidified 3-HPA broth from glucose finding an adsorption loading capacity of 230 mg 3-HPA/g dry resin for the polybenzimidazole (PBI) resin, and (bottom) and a desorption curve of 3-HPA from the resin using ethanol as the eluent, according to some embodiments of the present disclosure.
Figure 24:
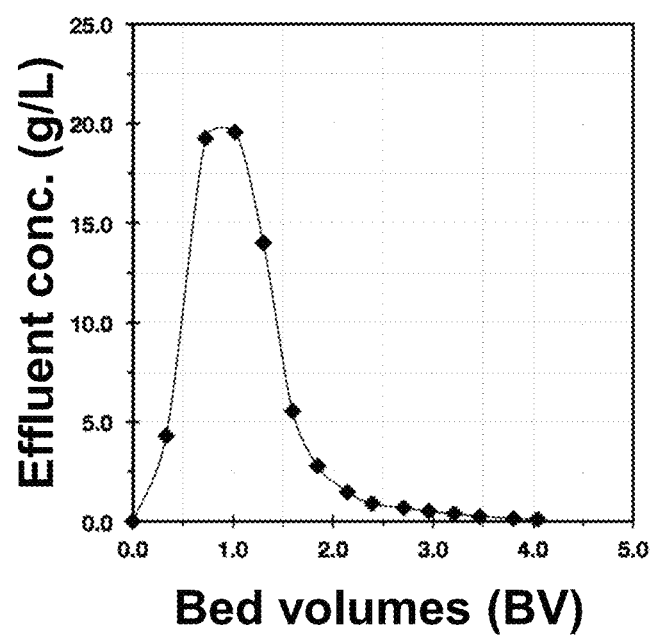

Referring again to FIG. 11, this figure demonstrates the success of the nitrilation chemistry to produce ≥90% yields of ACN from biologically derived ethyl 3-HP, according to embodiments of the present disclosure, potentially enabling a large-scale process for the hybrid biological and chemocatalytic transformation of lignocellulosic sugars to ACN. An embodiment of such a full-scale system, which concludes with the nitrilation of ethyl acrylate, is illustrated in FIG. 23. A full-scale process or system 300B, like a lab-scale process, will begin with a fermenter 310 to produce a broth 312, which as describe above, may be directed to a filter 320 for the removal of cells and debris 322 and/or proteins 324, resulting in a filtered broth 326. In a full-scale fermenter 310, fermentation may be conducted at pH 3, which is below the pKa of 3-HPA. The advantage gained from low pH fermentation is the acidification step is no longer needed during product separation. This markedly improves the process economics given that acidification is achieved industrially using ion exchange resins and this is the most costly operation in downstream bioprocesses. Low pH strains to produce 3-HPA at industrially relevant titers, rates, and yields may be developed based on previous engineering success with low-pH microbes. The filtered broth 326 containing 3-HPA, as in the lab-scale process, may then be directed to a dewatering unit 340. In the full-scale system 300B shown in the example of FIG. 23, the dewatering may be achieved by adsorption utilizing a resin where the dewatering unit 340 is operated as a simulated moving bed system, such that the resin selectively adsorbs the 3-HPA from the filtered broth 326 allowing the water 140 to pass out of the dewatering unit 340. To desorb the physically adsorbed 3-HPA from the resin of the dewatering unit 340, an alcohol 415 may be passed over the resin, resulting in the formation of a 3-HPA stream 382 in the alcohol. Results for such a dewatering adsorption unit are shown in FIG. 24 and indicate polybenzimidazole (PBI) works well and that 3-HPA may reversibly adsorbed onto PBI and desorbed from the PBI using ethanol with complete recovery. The dashed vertical line in the top diagram of FIG. 24 indicates the loading capacity of the PBI resin at approximately 230 mg of 3-HPA per gram of PBI resin.

Figure 25:
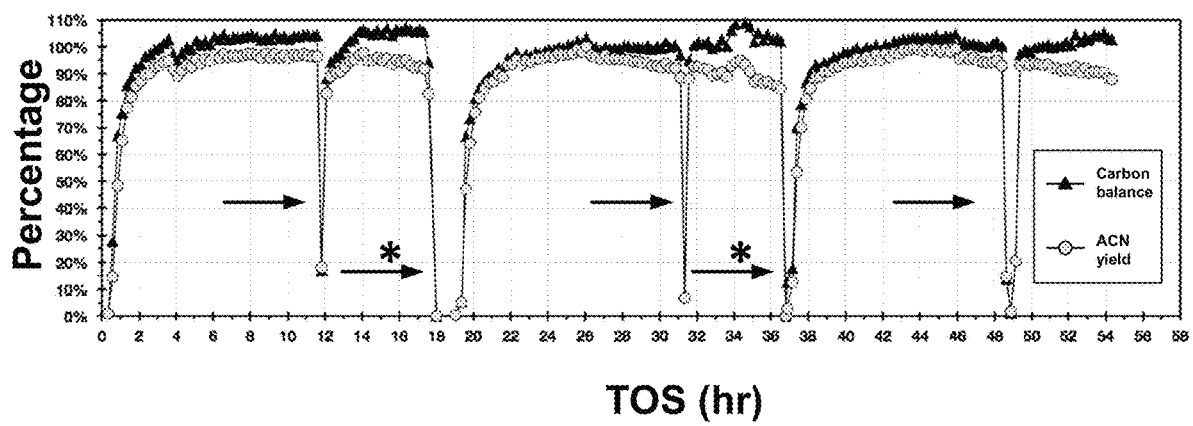
FIG. 25 illustrates a data set collected for the reaction of ethyl acrylate and ammonia demonstrating up to 100% quantitative yields of ACN was obtained for several hours on stream, according to some embodiments of the present disclosure. Three cycles of the catalyst are shown and break points (referring to the arrows) indicate syringe refill time points and catalyst regeneration cycles (arrows with asterisks). The overall heat of reaction was calculated to be endothermic by +81.2 kJ/mol.

Referring again to FIG. 23, in some embodiments of a full-scale system 300B, ethyl acrylate, instead of ethyl 3-HP, may be separated via a reactive distillation unit 400 resulting in an ethyl acrylate stream 417. Thus, for this example, the 3-HPA stream 410 in alcohol is directed to the reactive distillation unit 400, resulting in an ethyl acrylate stream 417 and an alcohol stream 415 that may be recirculated back to the adsorption dewatering unit 340. Thus, for this example, the reactive distillation unit 400 may simultaneously esterify and dehydrate the 3-HPA, converting it to ethyl acrylate. Reactive distillation provides a process simplification by combining the esterification (the —OH group dehydration reaction 1) of FIG. 3) and product separation into a single unit operation. This may be accomplished by distilling the ethanol/ethyl 3-HP solution in the presence of a mineral acid catalyst and/or by passing the vapors over a solid acid catalyst (e.g. Amberlyst® 15) placed in the reactive distillation unit 400. The resultant recovered ethyl acrylate stream 417 may then be fed to a nitrilation unit 420 for the production of ACN 426, for example two parallel packed bed reactors operated semi-continuously where nitrilation takes place in a first reactor (in the presence of ammonia 422), while catalyst regeneration occurs in a second reactor (not shown). An inert 425 (e.g. nitrogen) may be used as a carrier gas for the ethyl acrylate stream 417 to the nitrilation unit 420 for the production of ACN 426. The alcohol liberated during the nitrilation may be recovered downstream via condensation and recycled (not shown) to the reactive distillation unit 400. Experimental results for a system that nitrilates ethyl acrylate is shown in FIG. 25 and displays quantitative yields of ACN of up to 100% were obtained from the nitrilation of ethyl acrylate over $TiO_2$, highlighting that ethyl acrylate as a substrate achieves even higher yields than those shown in FIG. 11 for direct ethyl 3-HP processing. In some embodiments of the present disclosure, nitrilation of ethyl acrylate over $TiO_2$, may be accomplished at a WHSV of about 0.1 hr-1, at a temperature of about 310° C., and for a contact time of about 0.5 seconds.

Beyond ACN production, the nitrilation chemistry presented in this study has a much broader application in bioprocesses where its combination to any carboxylic acid or carboxylate ester production process may provide a facile route to convert acids to nitriles. Several biologically derived carboxylates may be produced at the industrial scale (e.g., succinic, lactic, itaconic, fumaric acid) and the nitrile or dinitrile derivatives of these acids may be obtained through the use of the chemistry described herein, which are valuable polymer precursors. A particular economic advantage also exists in coupling nitrilation to bioprocesses in that separation of the ester form of the carboxylic acids is generally more cost effective than separating the free acid. This is due to higher yields and purities of the ester that may be obtained through reactive distillation processes, whereas the free acids are usually separated through crystallization or chromatographically with simulated moving bed (SMB) technology, which are more expensive and exhibit lower yields than esterification operations. Note that the alcohol used in the esterification/separation is recovered and recycled from the nitrilation reaction.

The chemistry described herein provides multiple benefits in a green chemistry context over classical propylene ammoxidation, namely: (i) quantitative yields of ACN can be obtained from this reaction whereas state-of-the-art ammoxidation catalysts achieve ~80-83% yield of ACN (6); (ii) the reaction is endothermic by +81.2 kJ/mol (see Table 2 below) and does not require co-feeding $O_2$, enabling facile control in simple packed bed reactors. Comparatively, ammoxidation is a highly exothermic reaction requiring specialized reactors to avoid runaway reactions and explosions; (iii) no by-product hydrogen cyanide is produced during nitrilation, mitigating the toxicity and safe handling requirements of the product stream; (iv) the nitrilation reaction utilizes $TiO_2$ (or similar solid acid catalysts) as the catalyst, which is approximately 70% cheaper and much simpler in composition than the state-of-the-art ammoxidation catalysts that have undergone decades of development; and (v) the process provides a cost comparative, sustainable route to ACN from a renewable lignocellulosic feedstock whereas propylene is primarily a fossil derived resource.

| Species | $\Delta H_f^0$ | Units | B.P. |
|---|---|---|---|
| acrylamide | −130.2 | kJ/mol | polymerizes |
| acrylamide | +179.7 | kJ/mol | 77° C. |
| ammonia | −45.9 | kJ/mol | −33.3° C. |
| ethanol | −234.0 | kJ/mol | 78.37° C. |
| ethyl-3-HPA | N/A | kJ/mol | 187° C. |
| ethyl acrylate | −331.4 | kJ/mol | 99.4° C. |
| ethyl lactate | −695.1 | kJ/mol | 151-155° C. |
| water | −241.8 | kJ/mol | 100° C. |

Figure 26:
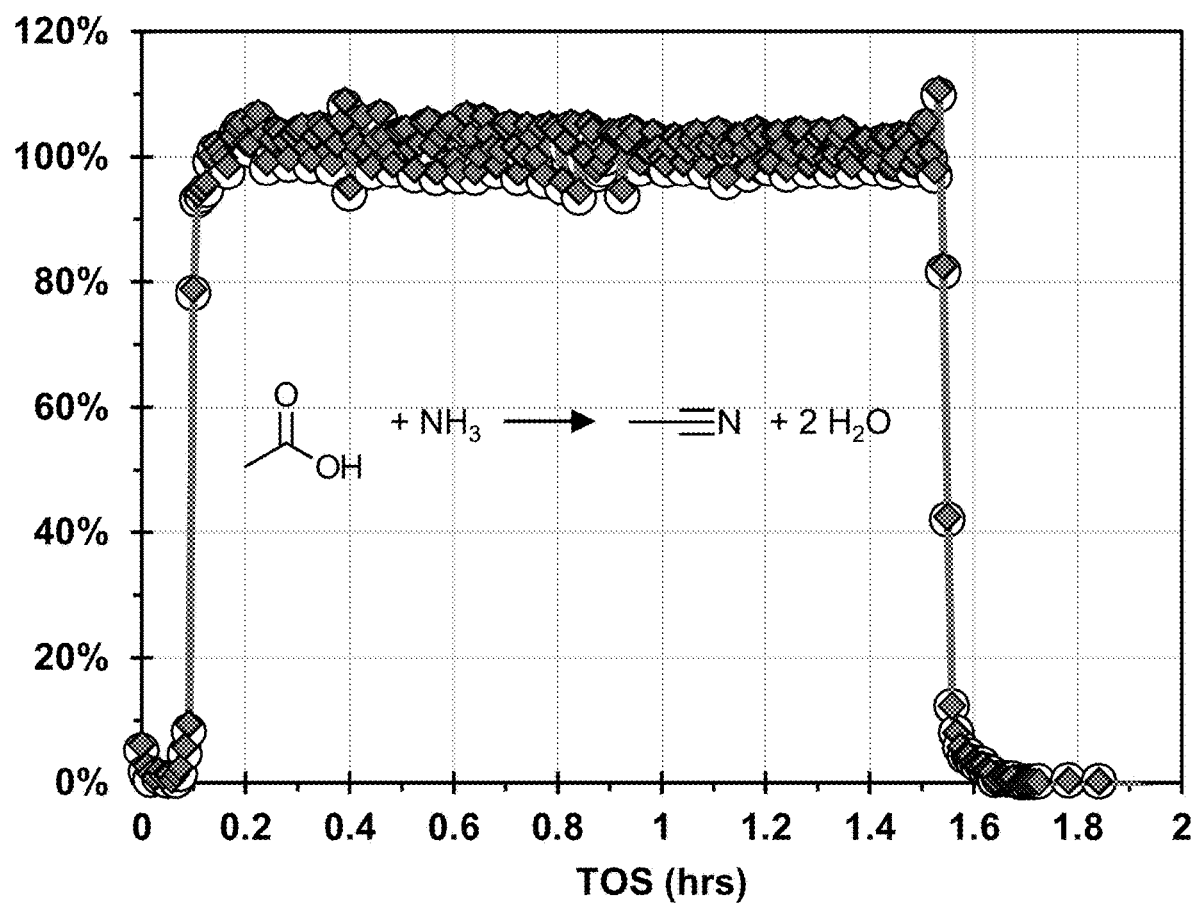
FIG. 26 illustrates experimental results for the nitrilation of ethyl acetate to produce acetonitrile, according some embodiments of the present disclosure. (Acetonitrile yield indicated by the diamonds and carbon balance indicated by the circles.)
Figure 27:
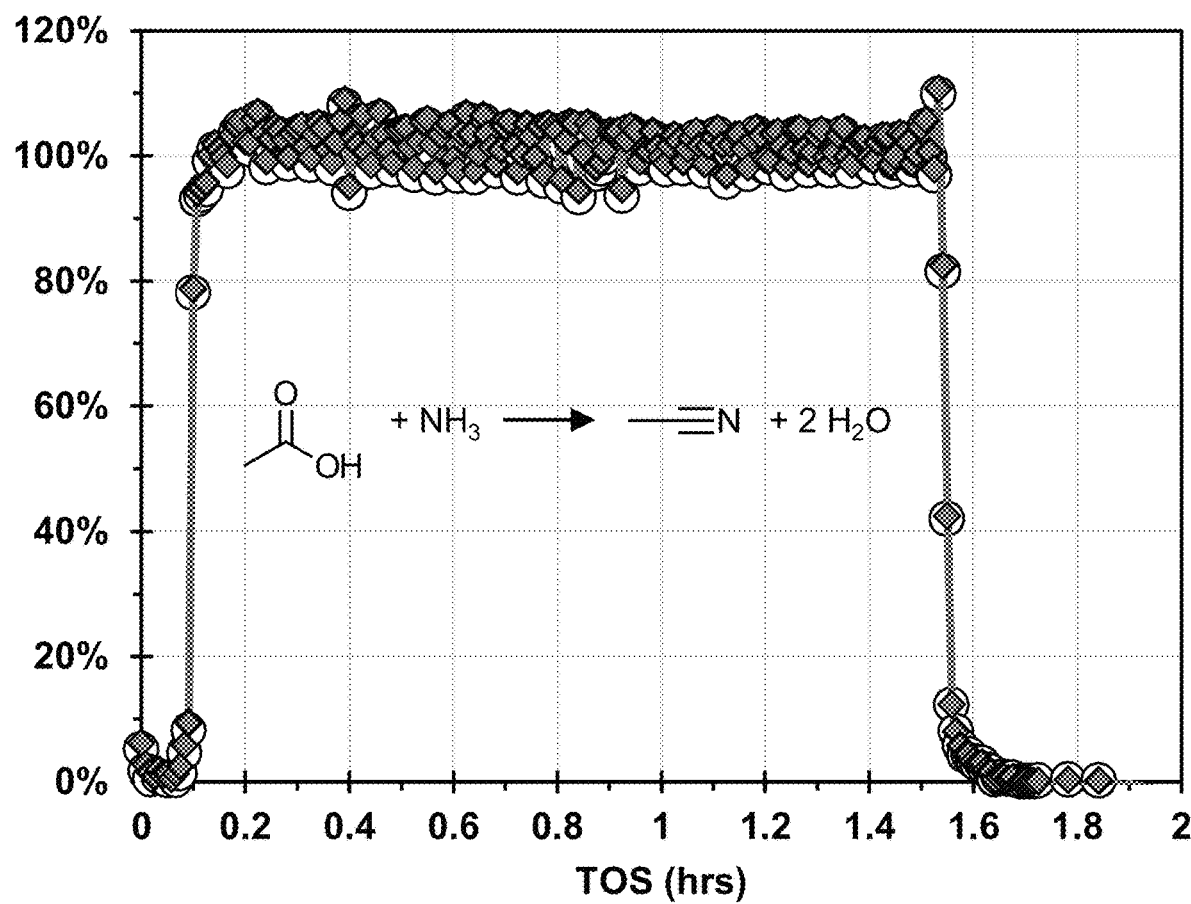
FIG. 27 illustrates experimental results for the direct nitrilation of acetic acid to produce acetonitrile, according some embodiments of the present disclosure. (Acetonitrile yield indicated by the diamonds and carbon balance indicated by the circles.)
Figure 28:
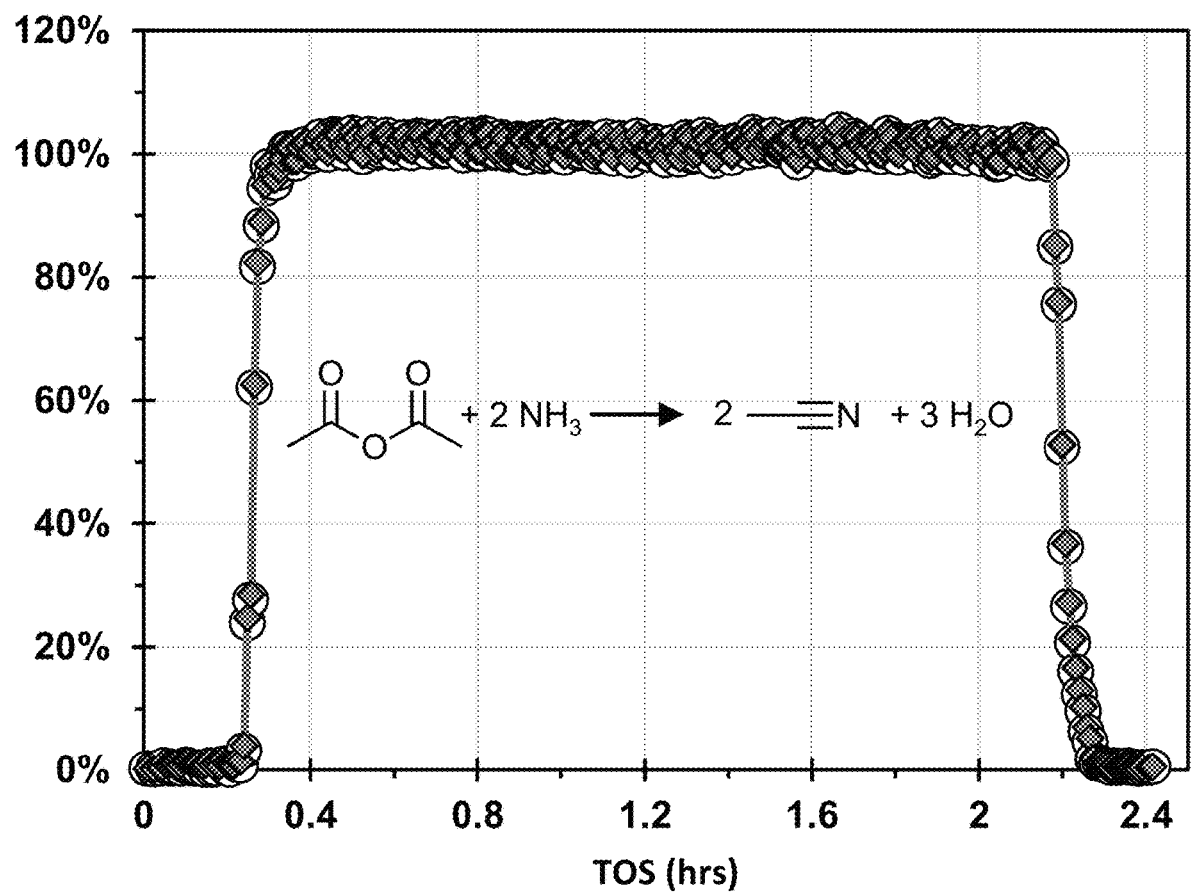
FIG. 28 illustrates experimental results for the direct nitrilation of acetic anhydride to produce acetonitrile, according some embodiments of the present disclosure. (Acetonitrile yield indicated by the diamonds and carbon balance indicated by the circles.)

FIGS. 26-28 provide experimental results for the conversion of methyl acetate, acetic acid, and acetic anhydride to acetonitrile, respectively. For the examples of acetic acid and acetic anhydride, the acetonitrile was produced in a single step by directly reacting these molecules with ammonia in the presence of a solid acid catalyst. For all three starting molecules, a gas feed to the reactor consisting of 1923 sccm $N_2$ carrier gas, 0.088 mL/min starting molecule (e.g. methyl acrylate, acetic acid, or acetic anhydride, all >95% pure) were added in the liquid phase and vaporized upon injection into the system, and ammonia fed to give a molar ratio of 4:1 $NH_3$:starting molecule (100 sccm $NH_3$ for ethyl acetate conversion, 140 sccm $NH_3$ for acetic acid conversion, and 85 sccm $NH_3$ for acetic anhydride conversion). The gas feed was passed over 43 g $TiO_2$ held at 315° C. Reaction products were detected with an MKS FTIR online gas analyzer that had been calibrated to measure methyl acetate, acetic acid, acetic anhydride, ammonia, acetonitrile, water, and methanol. Regardless of the starting molecule, yields of acetonitrile were >99% (as shown in FIGS. 26-28), indicating that esters, carboxylic acids, and anhydrides may be converted directly into nitriles by reaction with ammonia in the presence of an acid catalyst.

Material and Methods:

Catalysts.

$TiO_2$ was obtained from Johnson Matthey. The physical form of the $TiO_2$ catalyst was 0.5 mm diameter spheres, which were used as received without any further treatment.

Catalyst Characterization.

Catalyst characterization techniques were applied to both fresh and spent catalyst samples to determine physicochemical properties before and after reactions. In this section, "fresh" catalyst refers to a catalyst that was characterized as-received from the supplier, while "spent" catalyst refers to catalyst that was on stream for ethyl acrylate nitrilation for >12 hr.

The activation energy of ethyl 3-HP dehydration to ethyl acrylate (EA) was measured over $TiO_2$ both with and without ammonia present in the gas phase. The conditions for these measurements were: 2 to 5 g of $TiO_2$, 2000 sccm $N_2$, 0.077 mL/min ethyl 3-HP.

The total number of acids sites was measured with ammonia temperature programmed desorption (TPD) on an Altamira Instruments AMI-390 system. Catalyst samples (~100 to 200 mg) were packed into a quartz tube and heated to 600° C. at 10° C./min in 10% $O_2$/Ar flowing at 25 sccm and held for 1 hour to pre-treat the catalyst. The samples were then cooled to 120° C., flushed with 25 sccm He for 10 minutes, then saturated with ammonia by flowing 25 sccm of 10% $NH_3$/He over the samples for 30 minutes at 120° C. Excess ammonia was removed by flushing with 25 sccm He for 10 min. The samples were then heated to 600° C. in 25 sccm He at 30° C./min, holding at 600° C. for 30 min, and the desorbed ammonia was measured with a thermal conductivity detector (TCD) that monitored the catalyst bed effluent. The TCD was calibrated after each experiment by introducing 7 pulses of 10% $NH_3$/He from a 5 mL sample loop into a stream of 25 sccm He. Acid site quantification was performed assuming an adsorption stoichiometry of one ammonia molecule per site. This technique was applied to both fresh $TiO_2$ and spent $TiO_2$ to determine the change of acid site density before and after reaction. The acid site density for fresh $TiO_2$ was 160 µmol/g, while the acid site density for spent $TiO_2$ was 200 µmol/g.

The $NH_3$-TPD data was used to estimate the apparent activation energy of ammonia desorption on $TiO_2$ by leading edge analysis. For the leading-edge analysis, several Gaussian curves were fit to the TCD signal to remove noise, and the rate of ammonia desorption was calculated as a function of temperature using the TPD data, shown in FIG. 10. An Arrhenius plot of the ammonia desorption rate versus temperature was then made to estimate the apparent activation energy. The fitted model and averaged raw data were both plotted to estimate the apparent activation energy of ammonia desorption, giving an average value of 95 kJ/mol with a standard deviation of 8 kJ/mol.

The relative amount of Lewis to Brønsted acid sites was determined by pyridine adsorption diffuse-reflectance Fourier-transformed infrared spectroscopy (pyridine DRIFTS), using a Thermo Nicolet iS50 FT-IR spectrometer operating at 4 $cm^{-1}$ resolution equipped a Harrick Praying Mantis controlled-environment chamber and KBr windows. Fresh catalyst samples (~50 mg) were loaded into the chamber and pre-treated by heating in 100 sccm $N_2$ with a ramprate of 10° C./min to 300° C. and held at this temperature for 1 hour, then cooled to 150° C. A background spectrum was then collected of the clean catalyst surface before pyridine vapor was introduced by bubbling 100 sccm $N_2$ through liquid pyridine and through the catalyst bed for 10 minutes. The pyridine-saturated surface was then heated at 10° C./min and held at 300° C. for 30 min to remove pyridine that was not chemically bound to the surface, and then cooled to 150° C. A spectrum was then collected of the pyridine-modified catalyst and the absorption bands near 1445 $cm^{-1}$ (Lewis) and 1545 $cm^{-1}$ (Brønsted) and the relative absorption coefficients of these features ($\varepsilon_B/\varepsilon_L$=0.76), combined with total acid site density from ammonia TPD, were used to determine the number of Brønsted and Lewis acid sites. Pyridine DRIFTS of fresh and regenerated $TiO_2$ (see FIG. 15) showed that only Lewis acid sites were present, with adsorbed pyridine bands due to Lewis acid sites appearing at 1443, 1574, 1603, and 1612 $cm^{-1}$, and a band at 1490 $cm^{-1}$ attributed to physisorbed pyridine.

Figure 17:
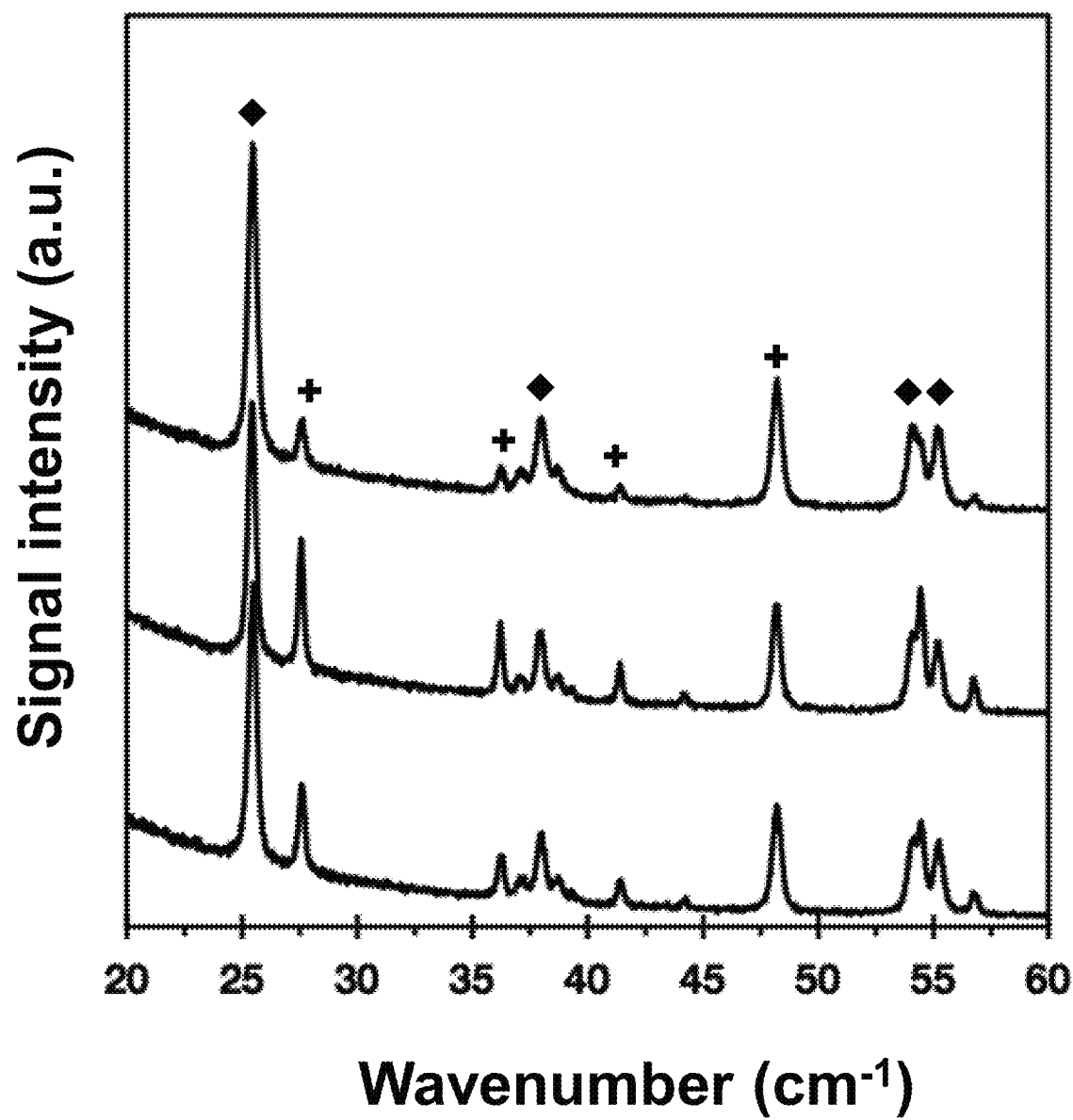
FIG. 17 illustrates x-ray diffractograms of fresh, spent, and regenerated $TiO_2$ (top, middle, and bottom data sets respectively), according to some embodiments of the present disclosure. (Diamonds indicate anatase reflections, pluses indicate rutile reflections.)
Figure 18:
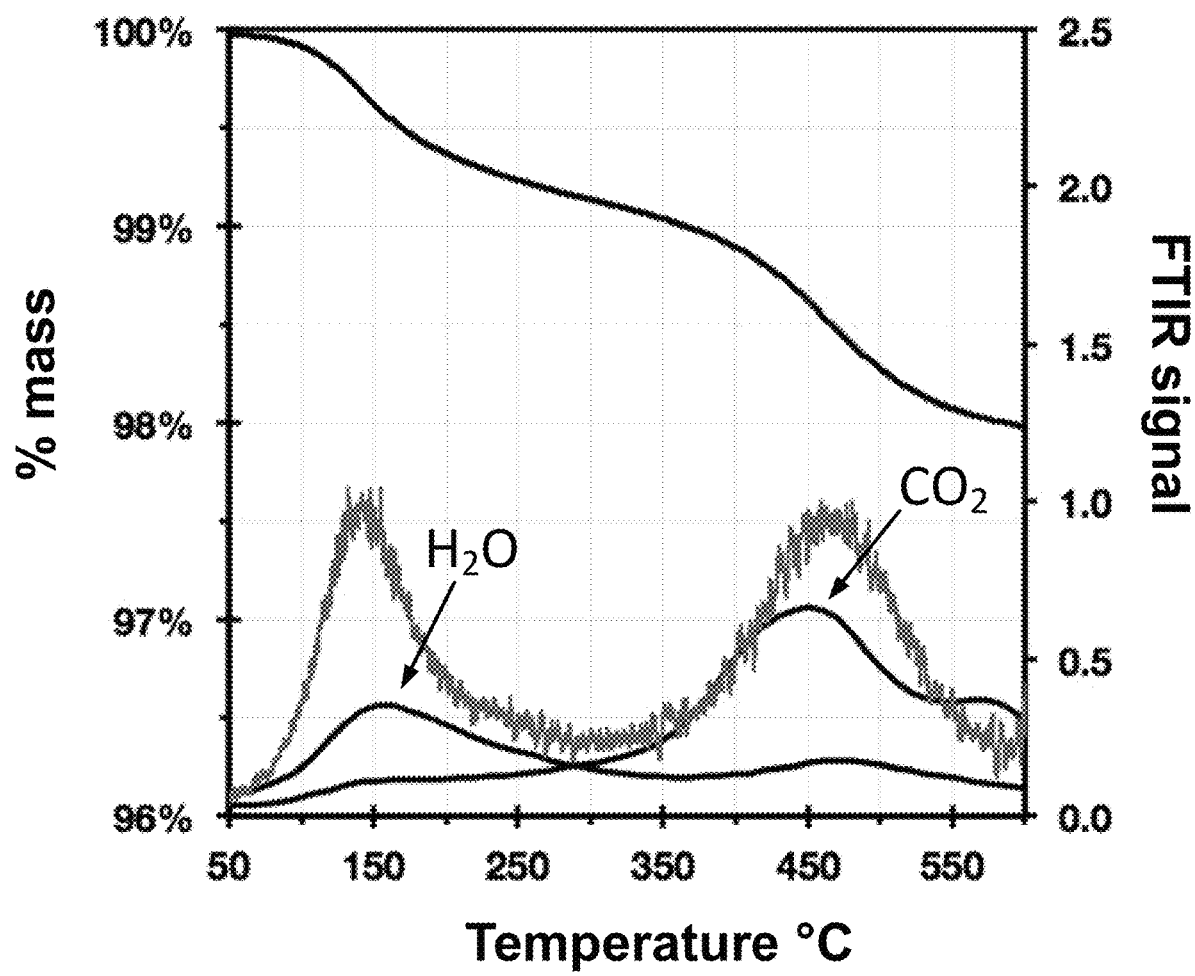
FIG. 18 illustrates thermogravimetric Fourier transform infrared spectroscopy (TGA-FTIR) results during coke burn-off of the spent catalyst shown in FIG. 14, according to some embodiments of the present disclosure. Note that no $NO_x$ was observed. Only carbon dioxide and water was observed. Mass loss is indicated by the top solid line. The mass loss derivative is indicated by irregular solid line below the mass loss line.

To quantify carbon laydown on spent $TiO_2$, and to identify the chemical identity of the carbon lay down, thermogravimetric analysis with fourier transformed infrared spectroscopy (TGA-FTIR) was performed on a ThermoScientific TGA-FTIR system, equipped with a Nicolet 6700 FTIR. Spent $TiO_2$ was loaded into the system and heated under flowing zero air (50 sccm) at a rate of 20° C./min to 600° C. Gas-phase combustion products from the catalyst surface were tracked with the FTIR. The major combustion products were carbon dioxide and water, while small amounts of carbon monoxide and methane were also detected. The catalyst mass loss and water and carbon dioxide signals are shown as a function of temperature in FIG. 18. No nitrogen-containing products were observed with the FTIR. X-ray diffraction was performed on fresh $TiO_2$ to determine the crystal phase, using a Rigaku Ultima IV diffractometer with Cu Kα radiation at a step size of 0.02°. Both anatase and rutile phases were observed in the $TiO_2$, as shown in FIG. 17.

Figure 16:
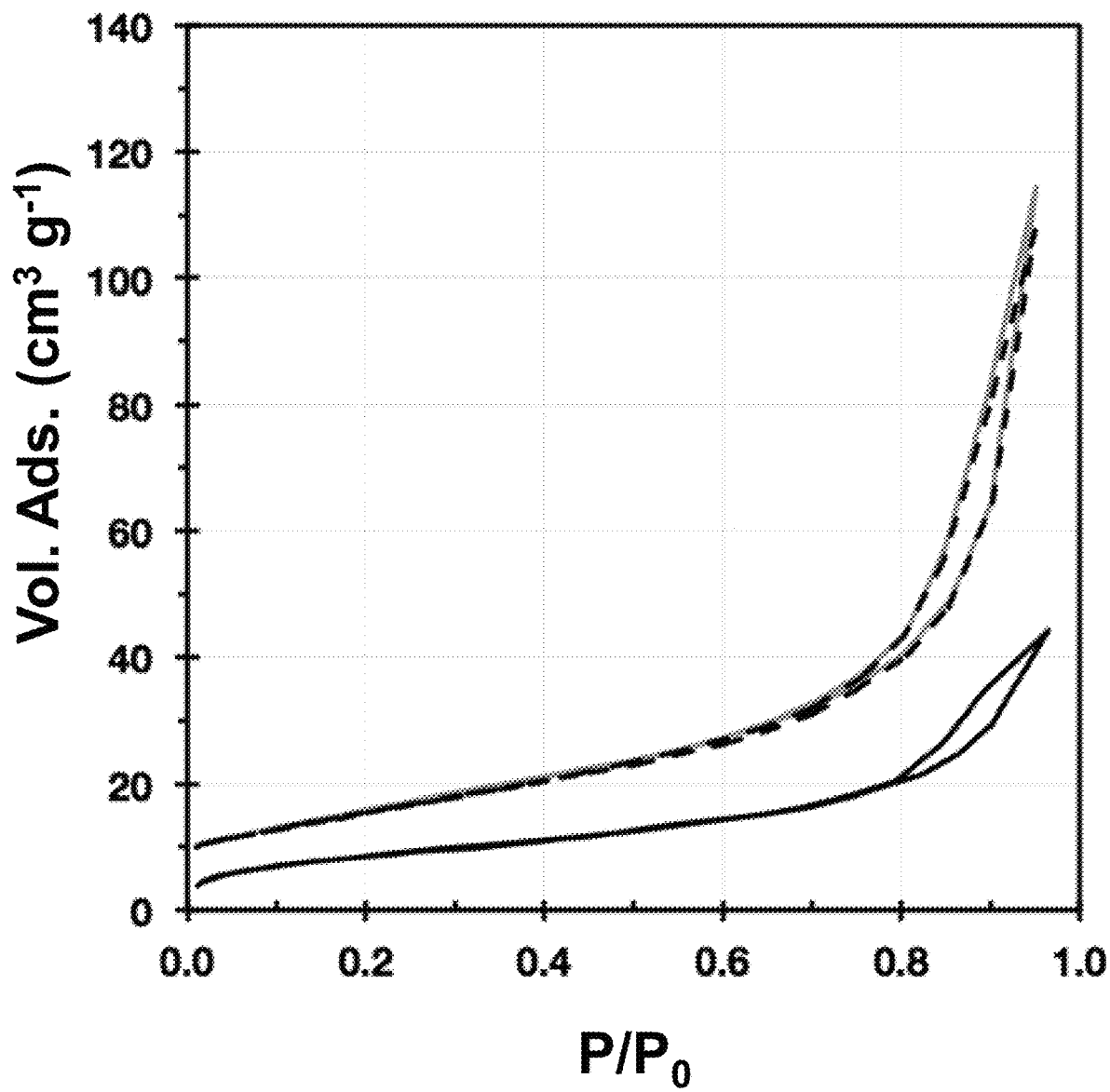
FIG. 16 illustrates nitrogen physisorption of fresh (dashed line), spent $TiO_2$ (lower solid line), and regenerated $TiO_2$ (upper solid line) with BET surface areas, according to some embodiments of the present disclosure. BET surface areas measured were 49 $m^2/g$, 27 $m^2/g$, and 50 $m^2/g$ respectively.

Nitrogen physisorption measurements to determine surface area were performed on a QuadraSorb SI instrument, using the BET method. Samples were dehydrated at 200° C. under vacuum prior to analysis. The isotherms are shown in FIG. 16 and show surface areas for fresh (49 $m^2$/g), spent (27 $m^2$/g), and regenerated (50 $m^2$/g) $TiO_2$.

Reagents for Nitrilation Experiments.

ethyl 3-HP (97%) (obtained from Combi-Blocks), ethanol (Pharmco-AAPER, 200 proof, lot # C16B08002), ethyl acrylate (Sigma-Aldrich lot # SHBC8912V), and ACN (Sigma-Aldrich, lot #SHBF8717V), were used to calibrate the online FTIR detector, described below. Ethyl acrylate (Sigma-Aldrich lot #SHBC8912V) was used as an inexpensive substrate to probe optimal reaction conditions given that ethyl-3-hydroxy propionate is much more costly and dehydrates rapidly to produce ethyl acrylate (see FIG. 6). Research grade purity of anhydrous ammonia gas (lot #900440732301) was obtained from Matheson TRIGAS and metered into the reactor system via a MKS mass flow controller.

Reactor System.

Reactions were performed in a custom-built flow reactor system with tandem catalytic beds. The substrate (ethyl 3-HP) was injected into a heated line at 150° C. and vaporized into an $N_2$ carrier gas. The flowrate of the $N_2$ gas was controlled with a MKS mass flow controller calibrated for $N_2$ and ranged from 0-2000 SCCM. Concentrations of the ester reagent were always <5% vol/vol of the gas entering into the reactor. Approximately 2.54 cm before the ester vapors entered the nitrilation reactor, ammonia gas was blended into the gas stream using an MKS mass flow controller calibrated for ammonia gas and ranged from 0-500 SCCM. Ammonia concentrations in the inlet gasses to the reactor were always <15% vol/vol. The reactors used were 50 mL in volume with an ID of 0.8" and 6" of length. A thermocouple was placed in the center of the bed to measure and control the temperature of the reactor. For high conversion studies the reactor was fully packed with catalyst, generally this was ~45 g of catalyst using the 0.5 mm diameter $TiO_2$ spheres from Johnson-Matthey. Exhaust gasses from the reactor bed were passed through the FTIR cell and then bubbled through chilled dimethylformamide (DMF) (4° C.), which contained ~100 ppm of 4-hydroxy-TEMPO as a polymerization inhibitor, held in a knockout pot. Two knockout pots are present on the system and a valve positioned downstream of the FTIR system allowed the exhaust gasses to be directed to the desired knockout pot. During an experiment the exhaust gasses were directed to one knockout pot until steady state was reached then the valve was switched to direct the exhaust gasses into the second knockout pot. This allowed collection of non-volatile components at steady state conditions. The DMF solution in the knockout pot collected ACN, ethyl acrylate, water and ethanol from the reaction. Excess ammonia was not absorbed into the DMF solution due to the aprotic nature of DMF.

Gas Phase FTIR System.

The reactor exhaust gas was monitored in real time using an MKS FTIR system (model 2030) with a 2 cm path length gas cell. The gas cell was heated and maintained at 19° C. Calibration curves for ammonia, ethanol, ethyl 3-hydroxy propionate, ethyl acrylate, ACN, and water were produced by metering in liquid compounds with a Series I HPLC pump (Scientific Systems Inc.) into nitrogen carrier gas in heated gas lines held at 150° C. Ammonia gas was blended into the $N_2$ carrier gas using a separate mass flow controller. Concentrations were varied between 1-18% vol/vol in $N_2$ to generate calibration curves. The spectra were appropriately fenced for quantification using the MKS software. Mass and carbon balances >90% were routinely achieved from the FTIR data for each reaction reported in this work when steady state was reached.

Synthesis of 3-HPA Standard.

3-hydroxy propionic acid can be purchased as a 30 wt. % solution in water from several chemical manufacturers. However, these products are not sufficiently pure to provide accurate calibration curves for analytical measurements. Therefore, a synthetic standard of sodium 3-hydroxy propionate was synthesized by adding 25 g beta-propiolactone to 500 ml of ultra pure water. That solution was stirred overnight to ensure complete ring opening of the lactone to form 3-hydroxy propionic acid in water. The solution was then titrated with a 1M solution of sodium hydroxide to its equivalency point (pH=9.33) forming sodium 3-hydroxy propionate. The solution was dried down using rotoevaporation and the recovered salt was dried in a 40° C. vacuum oven for 12 hours. The sodium salt of 3-HPA is stable, however the acid form is not stable above ~30 wt. % in water owing to its tendency to self-esterify. For calibration curves, the salt was used to produce calibration curves of known concentration and when contacted by the sulfuric acid mobile phase during HPLC analysis the salt form of 3-HPA was transformed to acid form before the detector observed it.

Genetic engineering of *Escherichia coli*.

*Escherichia coli* BG strain, kindly provided by Dr. Michael D. Lynch (Department of Biomedical Engineering & Chemistry. Duke University), was generated as follows: the genes ackA, pta, poxB, ldhA, adhE, and pflB (encoding acetate kinase, phosphate acetyltransferase, pyruvate oxidase, D-lactate dehydrogenase, aldehyde-alcohol dehydrogenase, and pyruvate formate-lyase, respectively) were deleted from strain BW25113 (*Coli* Genetic Stock Center, CGSC #: 7636 and a temperature sensitive fabI allele, inactive at 37° C., was used to decrease the metabolic flux into the fatty acid synthesis pathway and increase the accumulation of malonyl-coA. Genes of the 3-HPA pathway, mcr from *Chloroflexus aurantiacus* encoding a malonyl-CoA reductase (GenBank: AAS20429.1) and ydfG from *Escherichia coli* K12 (ecogene: EG12345), were cloned under the control of the constitutive J23119 promoter into a high copy vector pSMART (Lucigen Corporation, Middleton, Wis., USA). The resulting plasmid pSMART-HCkan-J23119-Camcr-ydfG was cloned into *Escherichia coli* BG following manufacturer's instructions (CloneSmart Cloning Kit, Lucigen Corporation) and the strain was named BGHP (see FIG. 19).

Media and Cultivation Conditions.

LB medium consisted of 10 g/L tryptone, 5 g/L yeast extract, 5 g/L NaCl. FM5 medium contained 2.63 g/L $K_2HPO_4$, 1.38 g/L $KHPO_4$, 3 g/L $(NH_4)_2SO_4$. 2.19 g/L citric acid×$H_2O$, 5 g/L yeast extract, 0.82 g/L $MgSO_4×7H_2O$, 20 mg/L $Fe_2(SO_4)_3×7H_2O$, 1.2 mg/L $CoSO_4×7H_2O$, 10 mg/L $CuSO_4×5H_2O$, 0.6 mg/L $ZnSO_4×7H_2O$, 0.4 mg/L $Na_2MoO_4×2H_2O$, and 0.2 mg/L $H_3BO_3$ (Sigma-Aldrich). Corn stover biomass, provided by Idaho National Laboratory, was hammer-milled and filtered through a rejection screen before de-acetylation with 0.4% (w/w) NaOH solution to achieve a 8% (w/w) total solids (TS) loading. After de-acetylation, pretreatment was carried out continuously using a horizontal screw fed reactor (Metso Inc, Norcross, Ga. USA) with dilute 1.0% $H_2SO_4$ (w/w) at 50% (w/w) TS. For the enzymatic hydrolysis, Novozymes Cellic® CTec2 was added after adjusting the post pretreatment slurry to 20% (w/w) TS with water and the pH to 5.2 using a 50% NaOH solution. Enzymatic hydrolysis was carried out with slight agitation at 48° C. for 168 h while maintaining a pH 5.2. The de-acetylated, dilute-acid pretreated, enzymatically hydrolyzed (DDAP-EH) hydrolysate was concentrated under vacuum at ~55° C. for 3 days and stored at 4° C. prior to use. The monomeric sugar composition of the resulting concentrated hydrolysate was: 240.0 g/L glucose, 137.5 g/L xylose, 4.5 g/L galactose, and 14.0 g/L arabinose. Feed for the glucose cultivation contained 500 g/L glucose supplemented with 25 g/L yeast extract. Concentrated DDAP-EH hydrolysate supplemented with 25 g/L yeast extract was used as feed in the hydrolysate cultivation. Cell concentrations were determined from absorbance measurements at 600 nm on sample diluted to give an optical density (OD) below 0.4 (Genesys™ 20, ThermoFisher Scientific, Walthman, Mass., USA). Seed cultures were generated by inoculation of 1 L baffled shake flasks containing 100 mL of LB with glycerol stock of *Escherichia coli* BGHP strain. Cells were aerobically grown in an orbital incubator (Innova 4330, New Brunswick, Eppendorf, Hauppauge, N.Y., USA) at 30° C., and 225 rpm for 16 h. Cells were harvested by centrifugation and resuspended with 0.9% NaCl solution. The seed culture was used to inoculate the bioreactors (Bioflo 310, New Brunswick) at initial OD of 0.1.

DO-Stat Fed-Batch Production of 3-HPA.

Fermentations were carried out in a DO-stat fed-batch mode. Aerobic conditions were obtained by continuously sparging air at 1 vvm and pH was kept constant at 7.0 by addition of 15% $(NH_4)OH$. During the batch phase, the DO level was maintained above 25% by increasing the agitation speed. In the glucose cultivation, medium FM5 supplemented with 10 g/L glucose was used for the batch phase. When glucose was depleted, pulses of glucose feed corresponding to 1 mM glucose were added to the bioreactor via a DO-stat control mode, where a DO level of 65% was set as a trigger. In the hydrolysate cultivation, concentrated DDAP-EH hydrolysate diluted to a final monomeric sugar concentration of 5 g/L glucose, 3.0 g/L xylose, 0.1 g/L galactose, and 0.3 g L arabinose, and supplemented with 5 g/L yeast extract was used for the batch phase. When sugars were depleted (confirmed by a sharp increase of DO level), pulses of hydrolysate feed corresponding to 0.45 mM monomeric sugars were added to the bioreactor via DO-stat control mode, where a DO level of 65% was set as a trigger. Every 24 hours, biotin and $NaHCO_3$ were added to the bioreactor at a final concentration of 40 µg/L and 20 mM, respectively. In all fermentations, temperature was switched from 30° C. to 37° C. once the culture reached an OD of 20. Antifoam 204 (Sigma-Aldrich) was added in the feed at a final concentration of 3 mL/L. Every 24 h, antibiotics Kanamycin (Sigma-Aldrich) and Gentamicin (Sigma-Aldrich) were added to a final concentration of 50 µg/L and 20 µg/L, respectively.

Metabolite Analysis.

Cells were quickly separated by centrifugation the supernant was filtered through 0.20 µm nylon membrane filter (Whatman, GE Healthcare Life Science, Pittsburgh. Pa., USA) and stored at 4° C. until analysis. 3-HPA, lactic acid, formic acid, acetic acid, and ethanol analysis was performed on an Agilent 1100 LC system equipped with a G1362A refractive index detector (Agilent Technologies, Palo Alto, Calif.). Each sample was injected at a volume of 20 µL onto an Aminex HPX-87H 7.8×300 mm i.d., 9 µm column (BioRad, Hercules, Calif.) at an oven temperature of 55° C. with an isocratic flow of 0.01 N $H_2SO_4$ at 0.6 mL/min. Analysis of glucose, galactose, xylose, and arabinose was performed using an ICS-5000+ system consisting of an AS-AP autosampler, and a pulsed electrochemical detector with a gold electrode and an Ag/AgCl reference electrode (Dionex Corporation, Sunnyvale, Calif., USA). Samples were diluted to a quantifiable range and 10 µL was injected on to a CarboPac SA-10 Dionex carbohydrates column (4×250 mm) paired with a CarboPac SA-10 guard column (4×50 mm). Sugars were separated with an isocratic flow of 1 mM potassium hydroxide at 1.5 mL min-1 prior to 5 min at 45° C. Following the sugar separation a ramp program was used with increasing potassium hydroxide concentration and then an equilibrium for a total run time of 15 min. Sugar standards of glucose (99.5% purity), galactose (≥99% purity), xylose (≥99% purity), and arabinose (≥98% purity) used to construct calibration curves between the range of 0.5-60 mg/L were purchased from Absolute Standards Inc (Hamden, Conn., USA).

Separation/Recovery of Ethyl 3-Hydroxy Propionate from Fermentation Broth.

Separation and recovery of ethyl 3-HP was achieved through the procedure/system outlined in FIG. 22. Here fermentation was conducted, as described above, with the pH maintained through the addition of ammonium hydroxide producing the ammonium 3-hydroxy propanoate salt. The broth was first treated by removing cells and debris through centrifugation and filtration through a 0.2 µm polyethersulfone filter (ThemoFisher Scientific). Then protein was removed from the cell free broth by filtration through a 10 kDa filter (GE Part # UFP-10-C-3X2MA). Activated carbon (3 w/v % for 4 hours) was then used to remove color bodies from the broth. The spent carbon was filtered off from the broth and the clarified broth dewatered by rotoevaporation leaving a crust of ammonium 3 hydroxy propanoate and sugar syrup. Next, the ammonium 3 hydroxy propanoate salt was dissolved into ~1 L of ethanol through gentle heating (~50° C.) of the dried material in ethanol. Note that the ammonium 3-HP salt is soluble in ethanol, as is ammonium lactate the structural isomer of ammonium 3-HP, and the sugar syrup was insoluble in ethanol. This dissolution process allowed the separation of the sugar syrup from the ammonium 3-HP salt. Next, the ethanol solution containing dissolved ammonium 3-HP salt was acidified with the addition of a stoichiometric amount of $H_2SO_4$. This produced ammonium sulfate, which is precipitated out of the ethanol solution and was filtered off, and left 3-HPA dissolved in ethanol. A catalytic amount of $H_2SO_4$ (0.025 mol $H_2SO_4$/mol 3-HPA) was added to the 3-HPA/ethanol solution and esterified under reflux for 100 minutes. After 100 minutes of refluxing the esterification solution was neutralized with the addition of 30 mL of ultra high purity water saturated with sodium bicarbonate. Salts produced from neutralization were filtered off and the ethyl-3HP product was isolated by vacuum distillation.

PBI Resin Testing.

Polybenzimidazole (PBI) was obtained from PBI performance products Inc. The loading capacity of 3-HPA on the resin was determined through measuring the loading curve shown in FIG. 24. For these experiments, 0.8 g (~8 mL wetted volume) of dry PBI resin was stirred in 200-proof ethanol for 20 minutes. The ethanol was vacuum filtered off and the resin slurried into a 25 mL burette in UHP water with a quartz wool plug at the base of the column. The column was allowed to settle and then rinsed with 10 BV of UHP water. 5-6 BV of cation exchanged and activated carbon (3 w/v %) treated 3-HPA broth was added on top of the resin and drained through at a rate of 3 BV/hr (0.4 ml/min). Effluent samples were taken at intervals between 0.3-0.6 BV and analyzed for acid concentrations as described in the analytical methods above. The breakthrough point was determined as the point when the effluent concentration reached 0.1 wt. % of the target acid. Using the breakthrough point the loading capacity of the resin was determined, in mg of the target acid/g dry resin using the equation (1) below.

$$\text{loading capacity} = \frac{V_{effluent} \times C_{acid}}{m_{pbi\ resin}}$$

In equation (1) above $V_{effluent}$ is the total volume in ml of effluent that was collect up to the breakthrough point, $C_{acid}$ is the concentration of 3-HPA in the broth in mg/ml, and $m_{PBI\ resin}$ is the dry mass of the PBI resin present in the column.

Elution profiles in FIG. 24 were constructed to determine the minimum volume of ethanol required to completely remove 3-HPA from the column. Here 0.8 g of PBI resin was columned in a 25 mL burette as described above. The resin was loaded with acid by passing cation exchanged and activated carbon (3 w/v %) treated 3-HPA broth through the column in order to load the resin with acid at the capacity determined from equation (1) of 230 mg 3-HPA/g dry PBI resin. 4-5 BV of ethanol elution solvent were passed through the column at a rate of 3 BV/hr. Effluent samples were taken at intervals between 0.3-0.6 BV and analyzed for 3-HPA concentrations as described in the analytical methods above. The minimum volume of eluent necessary to elute the target acid was determined by the first elution fraction to yield a concentration of 3-HPA below 0.2 wt %.

Beyond ACN production, the nitrilation chemistry presented here has a much broader application, for example in bioprocesses, where it may be utilized with a carboxylic acid and/or carboxylate ester production process to convert acids to nitriles. For example, several biologically derived carboxylates can be produced at the industrial scale such as succinic, lactic, itaconic, and fumaric acid and the nitrile or dinitrile derivatives of these acids may be obtained through the use of at least some of reactions presented herein, which are valuable polymer precursors. Shown below, are three example reaction schemes for producing succinonitrile from the reaction of succinic acid and/or the ester derivative of succinic acid with ammonia, adiponitrile from the reaction of adipic acid and/or the ester of adipic acid with ammonia, and fumaronitrile from the reaction of fumaric acid and/or the ester of fumaric acid with ammonia are shown respectively.

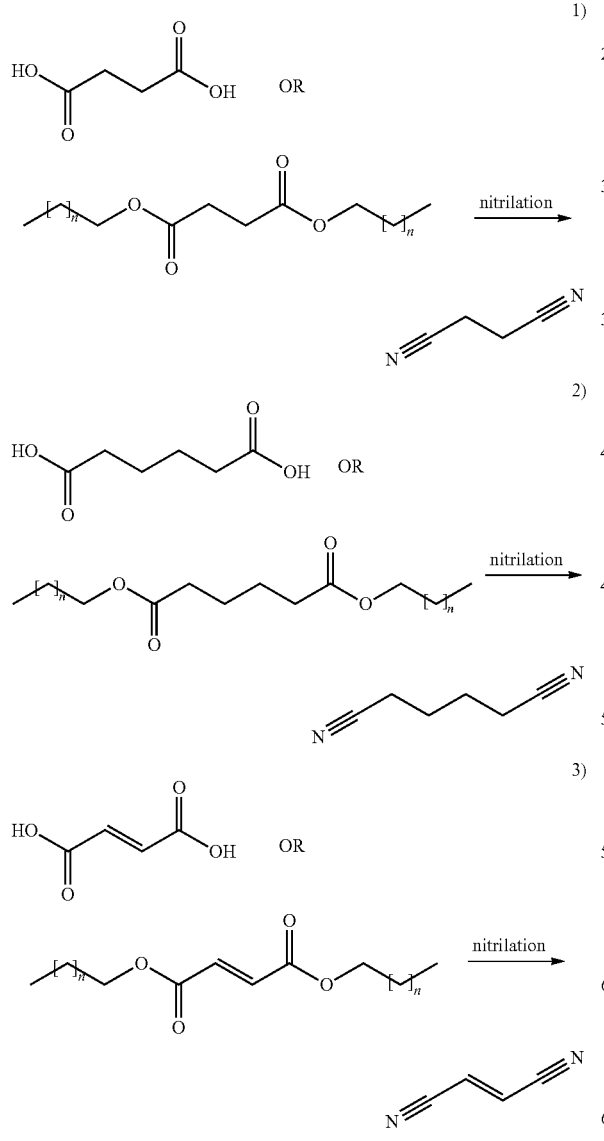

EXAMPLES

Example 1

A method comprising a first reacting of a molecule comprising at least one of a carboxylic acid, an ester of a carboxylic acid, or an anhydride with ammonia to form a nitrile, wherein the first reacting is catalyzed using an acid catalyst.

Example 2

The method of Example 1, wherein the molecule comprises at least one of a C2 carboxylic acid or a C3 carboxylic acid.

Example 3

The method of either Example 1 or 2, wherein the molecule comprises at least one of acetic acid, lactic acid, or 3-hydroxyproprionic acid (3-HPA).

Example 4

The method of either Example 1 or 2, wherein the molecule comprises at least one of an alkyl acetate, an alkyl lactate, or an alkyl 3-hydroxypropanoate.

Example 5

The method of either Example 1 or 2, wherein the molecule comprises at least one of methyl acetate, ethyl lactate, or ethyl 3-hydroxypropanoate (ethyl 3-HP).

Example 6

The method of Example 1, wherein the anhydride is acetic anhydride.

Example 7

The method of any one of Examples 1-6, wherein the nitrile comprises

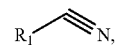

and $R_1$ comprises at least one of an alkyl group, an alkenyl group, an alkynyl group, a phenyl group, a carbonyl group, an aldehyde group, a carbonate group, a carboxylic acid group, and/or an ester group.

Example 8

The method of Example 7, wherein $R_1$ is a vinyl group and the nitrile is acrylonitrile (ACN).

Example 9

The method of Example 7, wherein $R_1$ is a methyl group and the nitrile is acetonitrile.

Example 10

The method of Example 1, wherein the nitrile comprises

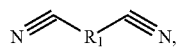

and $R_1$ comprises at least one an alkane linking group or an alkene linking group.

Example 11

The method of Example 10, wherein $R_1$ comprises at least one of —$CH_2$— or —$CH_2CH_2$—.

Example 12

The method of any one of Examples 1-11, wherein the acid catalyst is a solid acid catalyst.

Example 13

The method of any one of Examples 1-12, wherein the solid acid catalyst comprises at least one of a clay mineral, a metal oxide, a metal sulfide, a metal salt, a mixed oxide, a sulfate-promoted metal oxide, a mounted acid, a cation exchange resin, a perfluorinated polymeric sulphuric acid, or a heteropolyacid.

Example 14

The method of Example 13, wherein the metal oxide comprises at least one of $TiO_2$ or $ZrO_2$.

Example 15

The method of either Example 13 or 14, wherein the metal oxide has an acid density between 160 μmol/g and 200 μmol/g.

Example 16

The method of any one of Examples 1-15, wherein the first reacting is performed with both the molecule and the ammonia in the gas phase.

Example 17

The method of any one of Examples 1-16, wherein the first reacting is performed using a mixture of the molecule and the ammonia in an inert carrier gas.

Example 18

The method of Example 17, wherein the inert carrier gas is nitrogen.

Example 19

The method of any one of Examples 1-18, wherein the first reacting forms at least one of an alcohol or water.

Example 20

The method of Example 19, wherein the alcohol comprises at least one of methanol, ethanol, or propanol.

Example 21

The method of any one of Examples 1-20, wherein the first reacting is performed at a first temperature between 200° C. and about 500° C.

Example 22

The method of any one of Examples 1-21, wherein: the molecule is the ester of a carboxylic acid, prior to the first reacting, a second reacting of the carboxvlic acid with an alcohol to produce the molecule and water, and the second reacting regenerates the alcohol.

Example 23

The method of Example 22, further comprising recycling the regenerated alcohol to the first reacting.

Example 24

A method comprising esterifying a carboxylic acid with an alcohol to produce an ester and water; and nitrilating the ester to produce a nitrile, the alcohol, and water, wherein: the nitrilating is performed by reacting the ester with ammonia over a first acid catalyst.

Example 25

The method of Example 24, wherein the carboxylic acid comprises at least one of a C2 carboxylic acid or a C3 carboxylic acid.

Example 26

The method of either Example 24 or 25, wherein the carboxylic acid comprises at least one of acetic acid, lactic acid, or 3-hydroxyproprionic acid (3-HPA).

Example 27

The method of any one of Examples 24-26, wherein the ester comprises at least one of an alkyl acetate, an alkyl lactate, or an alkyl 3-hydroxypropanoate.

Example 28

The method of any one of Examples 24-27, wherein the ester comprises at least one of methyl acetate, ethyl lactate, or ethyl 3-hydroxypropanoate (ethyl 3-HP).

Example 29

The method of any one of Examples 24-29, wherein: the nitrile comprises

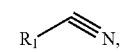

and R₁ comprises at least one of an alkyl group, an alkenyl group, an alkynyl group, a phenyl group, a carbonyl group, an aldehyde group, a carbonate group, a carboxylic acid group, and/or an ester group.

Example 30

The method of Example 29, wherein $R_1$ is a vinyl group and the nitrile is acrylonitrile (ACN).

Example 31

The method of Example 29, wherein $R_1$ is a methyl group and the nitrile is acetonitrile.

Example 32

The method of any one of Examples 24-31, wherein the first acid catalyst is a first solid acid catalyst.

Example 33

The method of Example 32, wherein the first solid acid catalyst comprises at least one of a clay mineral, a metal oxide, a metal sulfide, a metal salt, a mixed oxide, a sulfate-promoted metal oxide, a mounted acid, a cation exchange resin, a perfluorinated polymeric sulphuric acid, or a heteropolyacid.

Example 34

The method of Example 33, wherein the metal oxide comprises at least one of $TiO_2$ or $ZrO_2$.

Example 35

The method of Example 34, wherein the metal oxide has an acid density between 160 µmol/g and 200 µmol/g.

Example 36

The method of any one of Examples 24-35, wherein the nitrilating is performed with both the ester and the ammonia in the gas phase.

Example 37

The method of any one of Examples 24-36, wherein the nitrilating is performed using a mixture of the ester and the ammonia in an inert carrier gas.

Example 38

The method of Example 37, wherein the inert carrier gas is nitrogen.

Example 39

The method of any one of Examples 24-38, wherein the nitrilating forms the alcohol and water.

Example 40

The method of any one of Examples 24-39, wherein the alcohol comprises a primary alcohol.

Example 41

The method of Example 40, wherein the primary alcohol comprises at least one of methanol, ethanol, or propanol.

Example 42

The method of any one of Example 24-41, wherein the nitrilating is performed at a first temperature between 200° C. and about 500° C.

Example 43

The method of any one of Examples 24-42, further comprising removing the alcohol as it is formed during the nitrilating.

Example 44

The method of Example 24, further comprising recycling the alcohol from the removing to the esterifying.

Example 45

The method of any one of Examples 42-24, wherein the esterifying is performed at a second temperature that is less than the first temperature.

Example 46

The method of Example 45, wherein the second temperature is between 50° C. and about 450° C.

Example 47

The method of any one of Examples 24-46, wherein the esterifying is performed by contacting the carboxylic acid and the alcohol with a mineral acid.

Example 48

The method of Example 47, wherein the mineral acid is sulfuric acid.

Example 49

The method of any one of Examples 24-48, wherein the esterifying is performed with both the carboxylic acid and the alcohol in the liquid state.

Example 50

The method of any one of Examples 24-49, wherein the nitrilating is performed at an ester to ammonia molar ratio between 1:1 and 10:1.

Example 51

The method of any one of Examples 24-50, further comprising: after the esterifying, dehydrating a hydroxylated ester to produce an unsaturated ester, wherein: the carboxylic acid is hydroxylated, the ester is the hydroxylated ester, and the nitrile comprises an alkenyl group.

Example 52

The method of Example 51, wherein the alkenyl group is a vinyl group and the nitrile is acrylonitrile.

Example 53

The method of either Example 51 or 52, wherein the dehydrating is performed by contacting the hydroxylated ester with a second acid catalyst.

Example 54

The method of Example 53, wherein the second acid catalyst is a second solid acid catalyst.

Example 55

The method of either Example 53 or 54, wherein the second solid acid catalyst comprises at least one of a clay mineral, a metal oxide, a metal sulfide, a metal salt, a mixed oxide, a sulfate-promoted metal oxide, a mounted acid, a cation exchange resin, a perfluorinated polymeric sulphuric acid, or a heteropolyacid.

Example 56

The method of Example 55, wherein the metal oxide comprises at least one of $TiO_2$ or $ZrO_2$.

Example 57

The method of Example 56, wherein the metal oxide has an acid density between 160 µmol/g and 200 µmol/g.

Example 58

The method of any one of Examples 54-57, wherein the first acid catalyst and the second acid catalyst are the same.

Example 59

The method of any one of Examples 51-58, wherein the dehydrating and the nitrilating are performed at substantially the same time.

Example 60

A system comprising a nitrilation unit containing a first acid catalyst, a feed stream, an ammonia stream, and a product stream, wherein: the feed stream comprises at least one of a carboxylic acid, an ester of a carboxylic acid, or an anhydride, the product stream comprises

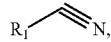

where $R_1$ comprises at least one of an alkyl group, an alkenyl group, an alkynyl group, a phenyl group, a carbonyl group, an aldehyde group, a carbonate group, a carboxylic acid group, and/or an ester group, and the product stream is formed by passing the feed stream over the first acid catalyst.

Example 61

The system of Example 60, wherein the first acid catalyst comprises at least one of a clay mineral, a metal oxide, a metal sulfide, a metal salt, a mixed oxide, a sulfate-promoted metal oxide, a mounted acid, a cation exchange resin, a perfluorinated polymeric sulphuric acid, or a heteropolyacid.

Example 62

The system of either Example 60 or 61, wherein the metal oxide comprises at least one of $TiO_2$ or $ZrO_2$.

Example 63

The system of Example 62, wherein the metal oxide has an acid density between 160 µmol/g and 200 µmol/g.

Example 64

The system of any one of Examples 60-63, wherein the feed stream is in the vapor phase.

Example 65

The system of any one of Examples 60-64, wherein the feed stream further comprises an inert carrier.

Example 66

The system of any one of Example 65, wherein the inert carrier is nitrogen.

Example 67

The system of any one of Examples 60-66, further comprising a distillation unit, a carboxylic acid stream comprising the carboxylic acid, and an alcohol stream, wherein: the carboxylic acid stream and the alcohol stream are fed to the distillation unit, and the carboxylic acid stream and alcohol stream react in the distillation unit to form the feed stream comprising the ester of the carboxylic acid.

Example 68

The system of Example 67, wherein the distillation unit contains a second acid catalyst.

Example 69

The system of either Example 67 or 68, wherein the second acid catalyst comprises at least one of a liquid mineral acid or a solid ion-exchange resin.

Example 70

The system of any one of Examples 67-69, further comprising a dewatering unit and a filtered broth stream comprising water and the dicarboxylic acid, wherein: the filtered broth stream is fed to the dewatering unit, and the dewatering unit removes at least a portion of the water from the filtered broth stream to form the carboxylic acid stream.

Example 71

The system of any one of Examples 67-70, wherein the dewatering unit comprises an adsorption column containing an adsorbent that selectively adsorbs at least a portion of the carboxylic acid.

Example 72

The system of any one of Examples 67-71, wherein at least a portion of the alcohol stream does not react in the distillation unit and the portion of the alcohol stream is recycled to the dewatering unit to remove the portion of the carboxylic acid to form the carboxylic acid stream.

Example 73

The system of any one of Examples 67-72, wherein the carboxylic acid stream and the alcohol stream are a single stream.

Example 74

The system of Example 71, wherein the adsorbent is polybenzimidazole.

Example 75

The system of any one of Examples 70-74, further comprising a filter unit and a broth stream comprising at least one of cells, debris, proteins, and the carboxylic acid, wherein: the broth stream is fed to the filter unit, the filter unit removes at least one of the cells, the debris, or the proteins to form the filtered broth stream, and the filter unit forms a by-product stream comprising at least one of the cells, the debris, or the proteins.

Example 76

The system of Example 75, further comprising a fermenter, wherein the fermenter produces the carboxylic acid, resulting in the broth.

Example 77

The system of Example 76, wherein the carboxylic acid is produced by *Escherichi Coli* metabolizing a sugar.

The foregoing discussion and examples have been presented for purposes of illustration and description. The foregoing is not intended to limit the aspects, embodiments, or configurations to the form or forms disclosed herein. In the foregoing Detailed Description or example, various features of the aspects, embodiments, or configurations are grouped together in one or more embodiments, configurations, or aspects for the purpose of streamlining the disclosure. The features of the aspects, embodiments, or configurations, may be combined in alternate aspects, embodiments, or configurations other than those discussed above. This method of disclosure is not to be interpreted as reflecting an intention that the aspects, embodiments, or configurations require more features than are expressly recited in each claim. Rather, as the following claims reflect, inventive aspects lie in less than all features of a single foregoing disclosed embodiment, configuration, or aspect. While certain aspects of conventional technology have been discussed to facilitate disclosure of some embodiments of the present invention, the Applicant in no way disclaims these technical aspects, and it is contemplated that the claimed invention may encompass one or more of the conventional technical aspects discussed herein. Thus, the following claims are hereby incorporated into this Detailed Description, with each claim standing on its own as a separate aspect, embodiment, or configuration.

What is claimed is:

1. A method comprising:
    a first reacting of a molecule consisting of at least one of lactic acid, 3-hydroxypropionic acid, ethyl lactate, ethyl 3-hydroxypropanoate, or acetic anhydride with ammonia to form a nitrile, wherein:
    the first reacting is catalyzed using a catalyst comprising $TiO_2$.

2. The method of claim 1, further comprising:
    prior to the first reacting, an initial reacting of at least one of lactic acid or 3-hydroxypropionic acid with an alcohol to produce at least one of ethyl lactate or ethyl 3-hydroxypropanoate and water, wherein:
    the first reacting regenerates the alcohol.

3. The method of claim 1, wherein the first reacting is performed with both the molecule and the ammonia in a gas phase.

4. The method of claim 2, wherein the initial reacting is performed by contacting the at least one of lactic acid or 3-hydroxypropionic acid and the alcohol with a mineral acid.

5. The method of claim 1, wherein the first reacting is performed at a molar ratio of the molecule to the ammonia between 1:1 and 10:1.

6. A method comprising:
    reacting an anhydride with ammonia to form a nitrile, wherein:
    the reacting is catalyzed using a catalyst comprising $TiO_2$, the nitrile consists of

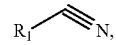

and
    $R_1$ consists of at least one of an alkyl group, an alkenyl group, an alkynyl group, a phenyl group, a carbonyl group, an aldehyde group, a carbonate group, a carboxylic acid group, or an ester group.

7. The method of claim 6, wherein the nitrile is acrylonitrile.

8. The method of claim 6, wherein the nitrile is acetonitrile.

* * * * *